US007910354B2

(12) United States Patent
Drmanac et al.

(10) Patent No.: US 7,910,354 B2
(45) Date of Patent: Mar. 22, 2011

(54) EFFICIENT ARRAYS OF AMPLIFIED POLYNUCLEOTIDES

(75) Inventors: Radoje T. Drmanac, Los Altos Hills, CA (US); Matthew Callow, Redwood City, CA (US)

(73) Assignee: Complete Genomics, Inc., Mountain View, CA (US)

(*) Notice: Subject to any disclaimer, the term of this patent is extended or adjusted under 35 U.S.C. 154(b) by 314 days.

(21) Appl. No.: 11/927,356

(22) Filed: Oct. 29, 2007

(65) Prior Publication Data
US 2008/0318796 A1    Dec. 25, 2008

Related U.S. Application Data

(60) Provisional application No. 60/863,157, filed on Oct. 27, 2006.

(51) Int. Cl.
C12M 1/34 (2006.01)
(52) U.S. Cl. .................................................. 435/287.2
(58) Field of Classification Search .................. None
See application file for complete search history.

(56) References Cited

U.S. PATENT DOCUMENTS

| | | | |
|---|---|---|---|
| 4,318,846 A | 3/1982 | Khanna | 260/999.999 |
| 4,469,863 A | 9/1984 | Ts'o et al. | 536/27 |
| 4,719,179 A | 1/1988 | Barany | 435/172.1 |
| 4,757,141 A | 7/1988 | Fung | 536/27 |
| 4,849,336 A | 7/1989 | Miyoshi | 435/6 |
| 4,883,750 A | 11/1989 | Whiteley | 435/6 |
| 4,886,741 A | 12/1989 | Schwartz | 435/5 |
| 5,034,506 A | 7/1991 | Summerton | 528/391 |
| 5,066,580 A | 11/1991 | Lee | 435/7.21 |
| 5,091,302 A | 2/1992 | Newman | 435/6 |
| 5,091,519 A | 2/1992 | Cruickshank | 536/29 |
| 5,124,246 A | 6/1992 | Urdea | 435/6 |
| 5,143,854 A | 9/1992 | Pirrung | 436/518 |
| 5,151,507 A | 9/1992 | Hobbs | 536/23 |
| 5,188,934 A | 2/1993 | Menchen | 435/6 |
| 5,198,537 A | 3/1993 | Huber | 530/406 |
| 5,216,141 A | 6/1993 | Benner | 536/23 |
| 5,235,033 A | 8/1993 | Summerton | 528/391 |
| 5,344,757 A | 9/1994 | Holtke | 435/66 |
| 5,354,657 A | 10/1994 | Holtke | 435/66 |
| 5,354,668 A | 10/1994 | Auerbach | 435/91.1 |
| 5,366,860 A | 11/1994 | Bergot | 435/66 |
| 5,386,023 A | 1/1995 | Sanghvi | 536/25.3 |
| 5,403,708 A | 4/1995 | Brennan | 435/6 |
| 5,426,180 A | 6/1995 | Kool | 536/25.3 |
| 5,427,930 A | 6/1995 | Birkenmeyer | 435/91.52 |
| 5,473,060 A | 12/1995 | Gryaznov | 536/24.3 |
| 5,474,796 A | 12/1995 | Brennan | 427/2.13 |
| 5,508,169 A | 4/1996 | Deugau | 435/6 |
| 5,571,677 A | 11/1996 | Gryaznov | 435/6 |
| 5,602,240 A | 2/1997 | Mesmaeker | 536/22.1 |
| 5,632,957 A | 5/1997 | Heller | 422/68.1 |
| 5,637,684 A | 6/1997 | Cook | 536/23.1 |
| 5,641,658 A | 6/1997 | Adams | 435/91.2 |
| 5,644,048 A | 7/1997 | Yau | 536/25.3 |
| 5,648,245 A | 7/1997 | Fire | 435/91.1 |
| 5,688,648 A | 11/1997 | Mathies | 435/6 |
| 5,702,888 A | 12/1997 | Holtke | 435/6 |
| 5,710,000 A | 1/1998 | Sapolsky | 435/6 |
| 5,714,320 A | 2/1998 | Kool | 435/6 |
| 5,728,524 A | 3/1998 | Sibson | 435/6 |
| 5,744,305 A | 4/1998 | Fodor | 435/6 |
| 5,800,992 A | 9/1998 | Fodor | 435/6 |
| 5,800,996 A | 9/1998 | Lee | 435/6 |
| 5,847,162 A | 12/1998 | Lee | 549/227 |
| 5,854,033 A | 12/1998 | Lizardi | 435/91.2 |
| 5,866,337 A | 2/1999 | Schon | 435/6 |
| 5,869,245 A | 2/1999 | Yeung | 435/6 |
| 5,871,921 A | 2/1999 | Landegren | 435/66 |
| 5,888,737 A | 3/1999 | DuBridge | 435/6 |
| 5,916,750 A | 6/1999 | Iyer | 435/6 |
| 5,990,479 A | 11/1999 | Weiss | 250/307 |
| 5,994,068 A | 11/1999 | Guilfoyle | 435/6 |
| 6,004,755 A | 12/1999 | Wang | 435/6 |
| 6,013,445 A | 1/2000 | Albrecht | 435/6 |
| 6,045,994 A | 4/2000 | Zabeau | 435/6 |
| 6,077,668 A | 6/2000 | Kool | 435/6 |
| 6,096,880 A | 8/2000 | Kool | 536/25.3 |
| 6,136,537 A | 10/2000 | Macevicz | 435/6 |
| 6,143,495 A | 11/2000 | Lizardi | 435/6 |

(Continued)

FOREIGN PATENT DOCUMENTS

| | | |
|---|---|---|
| JP | 4-262799 | 9/1992 |
| JP | 4-304900 | 10/1992 |
| WO | WO 91/17169 | 11/1991 |
| WO | WO 95/09248 | 4/1995 |
| WO | WO 01/62982 | 8/2001 |
| WO | WO 02/074988 | 9/2002 |
| WO | WO 02/077287 | 10/2002 |
| WO | WO 03/012119 | 2/2003 |
| WO | WO 03/106678 | 12/2003 |
| WO | WO 2004/072294 | 8/2004 |

(Continued)

OTHER PUBLICATIONS

Bankier, "Shotgun DNA Sequencing," Methods in Mol. Biol., v. 167, p. 89-100, (2001).

Beattie et al., "Hybridization of DNA targets to glass-tethered oligonucleotide probes," Molecular Biotechnology, v. 4, issue 3, p. 213-225 (1995).

Blanco et al., "Highly efficient DNA synthesis by the phage phi 29 DNA polymerase," J. Biol. Chem., v. 264, issue 15, p. 8935-8940 (1989).

(Continued)

*Primary Examiner* — Kenneth R. Horlick
*Assistant Examiner* — David C Thomas
(74) *Attorney, Agent, or Firm* — Robin M. Silva; Gargi Talukder; Morgan, Lewis & Bockius LLP

(57) ABSTRACT

The present invention is related generally to analysis of polynucleotides, particularly polynucleotides derived from genomic DNA. The invention provides methods, compositions and systems for such analysis. Encompassed by the invention are arrays of polynucleotides in which the polynucleotides have undergone multiple rounds of amplification in order to increase the strength of signals associated with single polynucleotide molecules.

8 Claims, 13 Drawing Sheets

U.S. PATENT DOCUMENTS

| | | | |
|---|---|---|---|
| 6,143,527 A | 11/2000 | Pachuk | 435/91.1 |
| 6,207,392 B1 | 3/2001 | Weiss | 435/7.1 |
| 6,210,891 B1 | 4/2001 | Nyren | 435/6 |
| 6,210,894 B1 | 4/2001 | Brennan | 435/6 |
| 6,218,152 B1 | 4/2001 | Auerbach | 435/91.2 |
| 6,221,603 B1 | 4/2001 | Mahtani | 435/6 |
| 6,251,303 B1 | 6/2001 | Bawendi | 252/301.4 |
| 6,255,469 B1 | 7/2001 | Seeman | 536/23.1 |
| 6,258,539 B1 | 7/2001 | Hunkapiller | 435/6 |
| 6,261,808 B1 | 7/2001 | Auerbach | 435/91.1 |
| 6,270,961 B1 | 8/2001 | Drmanac | 435/6 |
| 6,274,320 B1 | 8/2001 | Rothberg | 435/6 |
| 6,274,323 B1 | 8/2001 | Bruchez | 435/6 |
| 6,274,351 B1 | 8/2001 | Peponnet | 435/91.1 |
| 6,284,497 B1 | 9/2001 | Sabanayagam | 435/91.2 |
| 6,287,824 B1 | 9/2001 | Lizardi | 435/91.2 |
| 6,289,144 B1 | 9/2001 | Neuschafer | 385/12 |
| 6,291,183 B1 | 9/2001 | Pirrung | 435/6 |
| 6,297,006 B1 | 10/2001 | Drmanac | 435/6 |
| 6,297,016 B1 | 10/2001 | Egholm | 435/6 |
| 6,306,597 B1 | 10/2001 | Macevicz | 435/6 |
| 6,309,824 B1 | 10/2001 | Drmanac | 435/6 |
| 6,316,229 B1 | 11/2001 | Lizardi | 435/91.1 |
| 6,319,426 B1 | 11/2001 | Bawendi | 252/301.4 |
| 6,322,901 B1 | 11/2001 | Bawendi | 428/548 |
| 6,326,144 B1 | 12/2001 | Bawendi | 435/6 |
| 6,329,150 B1 | 12/2001 | Lizardi | 435/6 |
| 6,344,329 B1 | 2/2002 | Lizardi | 435/6 |
| 6,346,413 B1 | 2/2002 | Fodor | 435/287.2 |
| 6,355,432 B1 | 3/2002 | Fodor | 435/6 |
| 6,401,267 B1 | 6/2002 | Drmanac | 435/6 |
| 6,403,320 B1 | 6/2002 | Read | 435/6 |
| 6,413,722 B1 | 7/2002 | Arnold | 435/6 |
| 6,423,551 B1 | 7/2002 | Weiss | 436/518 |
| 6,426,513 B1 | 7/2002 | Bawendi | 257/13 |
| 6,432,360 B1 | 8/2002 | Church | 422/68.1 |
| 6,444,143 B2 | 9/2002 | Bawendi | 252/301.6 |
| 6,472,156 B1 | 10/2002 | Wittwer | 435/6 |
| 6,489,103 B1 | 12/2002 | Griffiths | 435/6 |
| 6,491,871 B1 | 12/2002 | Fodor | 422/63 |
| 6,500,620 B2 | 12/2002 | Yu | 435/6 |
| 6,514,768 B1 | 2/2003 | Guire | 436/518 |
| 6,534,293 B1 | 3/2003 | Barany | 435/91.2 |
| 6,558,928 B1 | 5/2003 | Landegren | 435/91.1 |
| 6,573,369 B2 | 6/2003 | Henderson | 536/23.1 |
| 6,576,291 B2 | 6/2003 | Bawendi | 428/215 |
| 6,576,448 B2 | 6/2003 | Weissman | 435/91.5 |
| 6,589,726 B1 | 7/2003 | Butler | 435/4 |
| 6,610,481 B2 | 8/2003 | Koch | 435/6 |
| 6,620,584 B1 | 9/2003 | Chee | 435/6 |
| 6,632,609 B2 | 10/2003 | Lizardi | 435/6 |
| 6,649,138 B2 | 11/2003 | Adams | 423/403 |
| 6,653,077 B1 | 11/2003 | Brenner | 435/6 |
| 6,654,505 B2 | 11/2003 | Bridgham | 382/278 |
| 6,783,943 B2 | 8/2004 | Christian | 435/6 |
| 6,787,308 B2 | 9/2004 | Balasubramanian | |
| 6,812,005 B2 | 11/2004 | Fan | 435/91.2 |
| 6,815,064 B2 | 11/2004 | Treadway | 428/403 |
| 6,828,100 B1 | 12/2004 | Ronaghi | 435/6 |
| 6,833,246 B2 | 12/2004 | Balasubramanian | 435/6 |
| 6,864,052 B1 | 3/2005 | Drmanac | 435/6 |
| 6,890,741 B2 | 5/2005 | Fan | 435/91.2 |
| 6,911,345 B2 | 6/2005 | Quake | 422/99 |
| 6,913,884 B2 | 7/2005 | Stuelpnagel | 435/6 |
| 6,977,153 B2 | 12/2005 | Kumar | 435/6 |
| 6,998,228 B2 | 2/2006 | Henderson | 435/4 |
| 7,011,945 B2 | 3/2006 | Qiao | 435/6 |
| 7,064,197 B1 | 6/2006 | Rabbani | 536/24.3 |
| 7,244,559 B2 | 7/2007 | Rothberg | 435/6 |
| 7,264,929 B2 | 9/2007 | Rothberg | 435/6 |
| 7,276,720 B2 | 10/2007 | Ulmer | 356/246 |
| 7,297,778 B2 | 11/2007 | Matsuzaki | 536/22.1 |
| 7,335,762 B2 | 2/2008 | Rothberg | 436/24.3 |
| 7,384,737 B2 | 6/2008 | Barnes | 435/6 |
| 7,544,473 B2 | 6/2009 | Brenner | 435/6 |
| 2001/0041340 A1 | 11/2001 | Kingsmore | 435/6 |
| 2002/0004204 A1 | 1/2002 | O'Keefe | 435/6 |
| 2002/0055100 A1 | 5/2002 | Kawashima | 435/6 |
| 2002/0076716 A1 | 6/2002 | Sabanayagam | 435/6 |
| 2003/0068629 A1 | 4/2003 | Rothberg | 435/6 |
| 2003/0143542 A1 | 7/2003 | Qiao | 435/6 |
| 2004/0002090 A1 | 1/2004 | Mayer | 435/6 |
| 2004/0224325 A1 | 11/2004 | Knapp | 435/6 |
| 2004/0229221 A1 | 11/2004 | Schon | 435/6 |
| 2004/0248144 A1 | 12/2004 | Mir | 435/6 |
| 2004/0248161 A1 | 12/2004 | Rothberg | 435/6 |
| 2005/0019776 A1 | 1/2005 | Callow | 435/6 |
| 2005/0037356 A1 | 2/2005 | Gullberg | 435/6 |
| 2005/0042649 A1 | 2/2005 | Balasubramanian | 435/6 |
| 2005/0079510 A1 | 4/2005 | Berka | 435/6 |
| 2005/0100939 A1 | 5/2005 | Namsaraev | 435/6 |
| 2005/0136414 A1 | 6/2005 | Gunderson | 435/6 |
| 2005/0142577 A1 | 6/2005 | Jones | 435/6 |
| 2005/0191656 A1 | 9/2005 | Drmanac | 435/6 |
| 2005/0214840 A1 | 9/2005 | Chen | 435/6 |
| 2005/0227264 A1 | 10/2005 | Nobile | 435/6 |
| 2005/0244863 A1 | 11/2005 | Mir | 435/6 |
| 2006/0012793 A1 | 1/2006 | Harris | 356/436 |
| 2006/0024681 A1 | 2/2006 | Smith | 435/6 |
| 2006/0024711 A1 | 2/2006 | Lapidus | 435/6 |
| 2007/0015182 A1 | 1/2007 | Abarzua | 435/6 |
| 2007/0037152 A1 | 2/2007 | Drmanac | 435/6 |
| 2007/0037197 A1 | 2/2007 | Young | 435/6 |
| 2007/0072208 A1 | 3/2007 | Drmanac | 435/6 |
| 2007/0092872 A1 | 4/2007 | Rothberg | 435/6 |
| 2007/0099208 A1 | 5/2007 | Drmanac | 435/6 |
| 2008/0234136 A1 | 9/2008 | Drmanac | 506/3 |
| 2009/0005252 A1 | 1/2009 | Drmanac | 506/3 |
| 2009/0005259 A1 | 1/2009 | Drmanac | 506/9 |
| 2009/0011416 A1 | 1/2009 | Drmanac | 435/6 |
| 2009/0011943 A1 | 1/2009 | Drmanac | 506/4 |
| 2009/0036316 A1 | 2/2009 | Drmanac | 506/4 |
| 2009/0099041 A1* | 4/2009 | Church et al. | 506/26 |
| 2009/0118488 A1 | 5/2009 | Drmanac | 536/24.2 |
| 2009/0137404 A1 | 5/2009 | Drmanac | 506/3 |
| 2009/0137414 A1 | 5/2009 | Drmanac | 506/9 |
| 2009/0155781 A1 | 6/2009 | Drmanac | 435/6 |
| 2009/0264299 A1 | 10/2009 | Drmanac | 506/3 |

FOREIGN PATENT DOCUMENTS

| | | |
|---|---|---|
| WO | WO 2004/076683 | 9/2004 |
| WO | WO 2005/040425 | 5/2005 |
| WO | WO 2005/042763 | 5/2005 |
| WO | WO 2005/047523 | 5/2005 |
| WO | WO 2005/078130 | 8/2005 |
| WO | WO 2005/080605 | 9/2005 |
| WO | WO 2005/082098 | 9/2005 |
| WO | WO 2005/093094 | 10/2005 |
| WO | WO 2005/116262 | 12/2005 |
| WO | WO 2006/007207 | 1/2006 |
| WO | WO 2006/040549 | 4/2006 |
| WO | WO 2006/055521 | 5/2006 |
| WO | WO 2006/073504 | 7/2006 |
| WO | WO 2006/074351 | 7/2006 |
| WO | WO 2006/084132 | 8/2006 |
| WO | WO 2006/138257 | 12/2006 |
| WO | WO 2007/014397 | 2/2007 |
| WO | WO 2007/025124 | 3/2007 |
| WO | WO 2007/061425 | 5/2007 |
| WO | WO 2007/062160 | 5/2007 |
| WO | WO 2007/106509 | 9/2007 |
| WO | WO 2007/121489 | 10/2007 |

OTHER PUBLICATIONS

Brenner et al, "Gene Expression Analysis by Massivly Parallel Signature Sequencing (MPSS) on Microbead Arrays," Nature Biotechnology, v. 18, p. 630-634 (2000).

Collins et al, "Directional cloning of DNA fragments at a large distance from an initial probe: A circularization method," Proc. Natl. Acad. Sci., 81: 6812-6816 (1984).

Dempcy et al., "Synthesis of a thymidyl pentamer of deoxyribonucleic guanidine and binding studies with DNA homopolynucleotides," Proc. Natl. Acad. Sci. USA 92: 6097-6101 (1995).

Dressman et al., "Transforming single DNA molecules into fluorescent magnetic particles for detection and enumeration of genetic variations," Proc. Natl. Acad. Sci., 100: 8817-8822 (2003).
Hirschhorn et al, "Genome-wide association studies for common diseases and complex traits," Nature Reviews Genetics, vol. 6, 95-108 (2005).
Jablonski et al., "Preparation of oligodeoxynucleotide-alkaline phosphatase conjugates and their use as hybridization probes," Nucleic Acids Research, vol. 14, p. 6115-6128 (1986).
Kojima et al., "PCR amplification from single DNA molecules on magnetic beads in emulsion: application for high-throughput screening of transcription factor targets," Nucleic Acids Research, 33 (17): e150 (2005).
Koshkin et al., "LNA (Locked Nucleic Acid): an RNA Mimic Forming Exceedingly Stable LNA Duplexes," J. Am. Chem. Soc. 120: 13252 3 (1998).
Kricka, "Stains, labels and detection strategies for nucleic acids assays," Ann. Clin. Biochem., vol. 39(2): 114-129 (2002).
Li et al., "A photocleavable fluorescent nucleotide for DNA sequencing and analysis," Proc. Natl. Acad. Sci., 100, 414-419 (2003).
Li et al., "BEAMing up for detection and quantification of rare wequence variants," Nature Methods, vol. 3, pp. 95-97 (2006).
Lieber, "The FEN-1 family of structure-specific nucleases in eukaryotic DNA replication, recombination and repair," BioEssays, vol. 19, pp. 233-340 (1997).
Margulies et al, "Genome sequencing in microfabricated high-density picolitre reactors," Nature, vol. 437, pp. 376-380 (2005).
Matthews et al., Analytical strategies for the use of DNA probes, Anal. Biochem., vol. 169, pp. 1-25 (1988).
Metzker, "Emerging Technologies in DNA Sequencing," Genome Research, 15: 1767-1776 (2005).
Mitra et al., "Fluorescent in situ sequencing on polymerase colonies," Anal. Biochem., vol. 320, pp. 55-65 (2003).
National Cancer Institute, Report of Working Group on Biomedical Technology, "Recommendation for a Human Cancer Genome Project, " (Feb. 2005).
Nie et al., "Quantitative Detection of Individual Cleaved DNA Molecules on Surfaces Using Gold Nanoparticles and Scanning Electron Microscope Imaging," Anal. Chem., vol. 78 (5), pp. 1528-1534 (2006).
Roe, "Shotgun Library Consturction for DNA Sequencing," Methods Mol. Biol., vol. 255, pp. 171-185 (2004).
Ronaghi et al., "A Sequencing Method Based on Real-Time Pyrophosphate," Science, vol. 281, pp. 363-365 (1998).
Service, Science, 311: 1544-1546 (2006).
Shendure et al, "Advanced Sequencing Technologies: Methods and Goals," Nature Reviews Genetics, vol. 5, pp. 335-344 (2004).
Tringe et al, "Metagenomics: DNA Sequencing of Environmental Samples," Nature Reviews Genetics, vol. 6, pp. 805-814 (2005).
Vingron et al., "Sequence Alignment and Penalty Choice Review of Concepts, Case Studies and Implications," J. Mol. Biol, vol. 235, issue 1, pp. 1-12 (1994).
Wetmur, et al. "DNA Probes: Applications of the Principles of Nucleic Acid Hybridization," Critical Reviews in Biochemistry and Molecular Biology, vol. 26, pp. 227-259 (1991).
Batzoglou et al, "ARACHNE: A whole-genome shotgun assembler," Genome Research, 12: 177-189 (2002).
Callow, Matthew J., et al. "Selective DNA amplification from complex genomes using universal double-sided adapters," Nucleic Acids Research, vol. 32, No. 2, e21, p. 1-6, (Jan. 2004).
Chen et al., "A Homogeneous, Ligase-Mediated DNA Diagnostic Test", Genome Research, vol. 8, No. 5, May 1998, pp. 549-556.
Cowie et al, "Identification of APC gene mutations in colorectal cancer using universal microarray-based combinatorial sequencing-by-hybridization," Human Mutation, 24:261-271 (2004).
Dahl et al, "Multiplex amplification enabled by selective circularization of large sets of genomic DNA fragments," Nucleic Acids Research, 33(8): e71 (2005).
Ladner, D.P. et al., "Multiplex detection of hotspot mutations by rolling circl-enabled universal microarrays," Laboratory Investigation, US and CA Academy of Pa;thology, vol. 81, No. 8, p. 1079-1086 (Aug. 1, 2001).

* cited by examiner

EFFICIENT ARRAYS OF AMPLIFIED POLYNUCLEOTIDES

CROSS-REFERENCE TO RELATED APPLICATIONS

This application claims priority to U.S. Provisional Application Ser. No. 60/863,157, filed on Oct. 27, 2006, which is hereby incorporated by reference in its entirety.

BACKGROUND OF THE INVENTION

Large-scale sequence analysis of genomic DNA is central to understanding a wide range of biological phenomena related to states of health and disease both in humans and in many economically important plants and animals, e.g., Collins et al (2003), Nature, 422: 835-847; Service, Science, 311: 1544-1546 (2006); Hirschhorn et al (2005), Nature Reviews Genetics, 6: 95-108; National Cancer Institute, Report of Working Group on Biomedical Technology, "Recommendation for a Human Cancer Genome Project," (February, 2005); Tringe et al (2005), Nature Reviews Genetics, 6: 805-814. The need for low-cost high-throughput sequencing and re-sequencing has led to the development of several new approaches that employ parallel analysis of many target DNA fragments simultaneously, e.g., Use of water/buffer-in-oil emulsions to carry out enzymatic reactions is well known in the art, particularly carrying out PCRs, e.g., as disclosed by Drmanac et al., Scienta Yugoslavica, 16(1-2): 97-107 (1990), Margulies et al, Nature, 437: 376-380 (2005); Margulies et al, Nature, 437: 376-380 (2005); Shendure et al (2005), Science, 309: 1728-1732; Metzker (2005), Genome Research, 15: 1767-1776; Shendure et al (2004), Nature Reviews Genetics, 5: 335-344; Lapidus et al, U.S. patent publication US 2006/0024711; Drmanac et al, U.S. patent publication US 2005/0191656; Brenner et al, Nature Biotechnology, 18: 630-634 (2000); and the like.

Such approaches reflect a variety of solutions for increasing target polynucleotide density in planar arrays and for obtaining increasing amounts of sequence information within each cycle of a particular sequence detection chemistry. Most of these new approaches are restricted to determining a few tens of nucleotides before signals become significantly degraded, thereby placing a limit on overall sequencing efficiency.

Another limitation of traditional high-throughput sequencing techniques is that arrays with a high density of single molecules often suffer from a poor signal to noise ratio, due to overlap of signals between different molecules. Most traditional sequencing techniques are not effective in the analysis of arrays of single molecules, because the signal associated with single molecules are often not intense enough to overcome noise inherent in such systems.

In view of such limitations, it would be advantageous for the field if arrays could be designed to strengthen the signals associated with single polynucleotide molecules disposed on such arrays.

SUMMARY OF THE INVENTION

In one aspect, the invention provides a method of making a random array of amplified polynucleotides. Such a method includes the step of providing: (i) a surface that includes capture probes, which have free 3' ends; (ii) a plurality of target polynucleotide concatemers disposed on the surface. In a particularly preferred aspect, each concatemer is bound to capture probes at a specific position on the surface. In this aspect of the invention, the method further includes the step of extending the capture probes such that the concatemers disposed on the surface are amplified. In this aspect, the amplification products of the concatemers are attached to the surface at or near the specific position of the concatemer that is amplified, thus making the random array of amplified polynucleotides.

In another aspect, the invention provides a method of making a random array of target polynucleotides which includes the steps of: (i) providing a plurality of concatemers on a surface, where the surface includes capture probes; (ii) cleaving at least a portion of the plurality of concatemers with a nicking endonuclease to form cleavage products; (iii) circularizing the cleavage products on the capture probes; and (iv) extending the capture probes by rolling circle replication to create at least one copy of each circularized cleavage product; thus making the random array of target polynucleotides. In one preferred aspect of this method, the plurality of concatemers includes multiple copies of the target polynucleotide and an adaptor. In a further preferred aspect of this method, the cleavage products formed in step (ii) remain attached to said capture probes. In another aspect of this method, each concatemer is attached to a specific position on the surface through duplexes formed between the capture probes and the adaptors in the concatemers, and these duplexes include a recognition site for the nicking endonuclease.

In still another aspect, the invention provides a method of making a random array of amplified target polynucleotides. This method includes the steps of: (i) providing a plurality of tailed concatemers; (ii) extending the tailed concatemers with a strand-displacing polymerase to form concatemer-extension product complexes; and (iii) disposing the concatemer-extension product complexes on a surface, thus forming a random array of target polynucleotides. In a preferred aspect of this method, the surface includes capture probes and a majority of the concatemer-extension product complexes from a single concatemer occupy a single region of the surface. In a particularly preferred aspect of this method, the majority of the concatemer-extension product complexes is attached to the surface by one or more duplexes formed between the capture probes and said the tail portions of the tailed concatemers.

In yet another aspect, the invention provides a method of making a random array of target polynucleotides. This method includes the step of combining under annealing conditions a plurality of dendrimers and a plurality of single stranded DNA circles, where the single stranded DNA circles include a target polynucleotide and an adaptor, and each of the plurality of dendrimers includes a primer capable of annealing to the adaptors of the plurality of single stranded DNA circles. This method also includes the steps of annealing the adaptors of the single stranded DNA circles to the primers of the plurality of dendrimers; extending the primers annealed with the adaptors with a strand-displacing polymerase to form a plurality of dendrimer-extension product complexes; and disposing the dendrimer-extension product complexes on a surface such that each of at least a majority of the plurality of dendrimer-extension product complexes occupies a separate region on the surface, thus forming the random array of target polynucleotides.

In one aspect, the invention provides a method of forming a spatially-compact single stranded amplicon. This method includes the step of combining under annealing conditions a dendrimer and a single stranded DNA circle, where the single stranded DNA circle includes a target polynucleotide and an adaptor, and the dendrimer includes a primer capable of annealing to the adaptor and at least one capture sequence identical to a portion of the single stranded DNA circle. This method also includes the steps of: extending the primer annealed to the adaptor with a strand-displacing polymerase to form a single-stranded amplicon, where at least one of the capture sequences forms a duplex with a complementary portion of the single stranded amplicon, thus forming the spatially-compact single stranded amplicon.

In still another aspect the invention provides a method of forming a single-stranded amplicon, where the amplicon includes multiple target polynucleotide sequences. This method includes the step of combining under annealing conditions a dendrimer and a plurality of single stranded DNA circles, where each single stranded DNA circle includes a target polynucleotide and an adaptor, and the dendrimer includes multiple sites complementary to adaptors on different DNA circles. This method further includes the steps of: extending the primer annealed to the adaptor with a strand-displacing polymerase to form a single stranded amplicon, where portions of each amplicon are complementary to target polynucleotides of different DNA circles, thus forming spatially compact single stranded amplicons which include multiple target polynucleotide sequences.

In one aspect, the invention provides a method of forming a double stranded amplicon. This method includes the steps of: (i) providing a single stranded amplicon which includes a concatemer having multiple copies of a target polynucleotide and an adaptor; annealing primers to the adaptors of the single stranded amplicon; and (ii) extending the primers with a non-strand displacing polymerase so that substantially every annealed primer is extended to form an extension product that abuts the next annealed primer, thus forming a double stranded amplicon.

In one aspect the invention provides a method of making a random array of target polynucleotides. This method includes the steps of: (i) providing a support having a surface; (ii) combining in a reaction mixture first primer probes, beads comprising second primer probes on their surfaces, and a plurality of concatemers each comprising multiple copies of a target polynucleotide and an adaptor, the first primer and second primer probes being capable of amplifying in a polymerase chain reaction a portion of said concatemers; (iii) forming an emulsion with the reaction mixture so that aqueous compartments are formed that contain second primers, and no more than one bead and no more than one concatemer; (iv) conducting a polymerase chain reaction in the aqueous compartments so that portions of the concatemer are amplified on the beads; and (v) disposing the beads from the emulsion onto the surface such that substantially every bead occupies a separate region of the surface, thus forming the random array of target polynucleotides.

In one aspect, the invention provides a method of identifying a nucleotide sequence of a target polynucleotide. In this method, a random array is provided, and this random array includes a plurality of concatemers disposed on a surface, where the concatemers include at least one fragment of the target polynucleotide, and where the concatemers have undergone at least one round of in situ amplification. The method further includes the steps of hybridizing one or more probes from a first set of probes to the random array under conditions that permit formation of perfectly matched duplexes between the one or more probes from the first set of probes and complementary sequences on said concatemers; and hybridizing one or more probes from a second set of probes to the random array under conditions that permit the formation of perfectly matched duplexes between the one or more probes from the second set of probes and complementary sequences on the concatemers. In a preferred aspect, probes the first and second sets of probes which are hybridized to contiguous sites of the target concatemers are ligated. In this aspect, the sequences of the ligated probes are identified to generate a sequence read. The steps of hybridizing probes from the first and second set, ligating probes hybridized to contiguous sites and identifying the ligated probes are repeated a number of times to generate multiple sequence reads. The multiple sequence reads are then assembled, thus identifying the nucleotide sequence of the target polynucleotide.

In another aspect, the invention provides a method of identifying a nucleotide sequence of a target polynucleotide. In this aspect, a random array including a plurality of concatemers disposed on a surface is provided. The concatemers disposed on the surface include at least one fragment of the target polynucleotide, at least one interspersed adaptor, and have undergone at least one round of in situ amplification. The at least one interspersed adaptor is adjacent to at least one fragment. This method further includes the step of identifying a sequence of at least a portion of the at least one fragment adjacent to the at least one interspersed adaptor, thus identifying the nucleotide sequence of the target polynucleotide.

In still another aspect, the invention provides a method of identifying a first nucleotide at a detection position of a target sequence, where the target sequence includes a plurality of detection positions. In this method, a plurality of concatemers is provided, where each of the concatemers includes a plurality of monomers and each monomer includes: a first target domain of the target sequence including a first set of target detection positions; a first adaptor including a Type IIs endonuclease restriction site; a second target domain of the target sequence including a second set of target detection positions; and an interspersed adaptor including a Type IIs endonuclease restriction site. In this aspect, the invention includes the steps of amplifying the plurality of concatemers and identifying the first nucleotide at a detection position of the target sequence.

In one aspect, the invention provides a random array of target polynucleotides of unknown sequence. This random array includes a substrate having a surface and a plurality of concatemer extension products disposed on the surface. In this aspect, the plurality of concatemer extension products is formed from in situ amplification of immobilized concatemers, and each of the plurality of concatemer extension products includes at least two copies of a single-stranded concatemer, where the single-stranded concatemer includes multiple copies of an identical target polynucleotide of unknown sequence.

In one aspect, the invention provides a kit for in situ amplification. Such a kit includes a support having a surface which includes first stage amplicons; adaptors; at least one ligase; at least one nicking endonuclease and reactants for a reaction using the at least one nicking endonuclease; and at least one polymerase and reactants for a synthesis reaction using the at least one said polymerase.

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

DETAILED DESCRIPTION OF THE INVENTION

Figure 1:
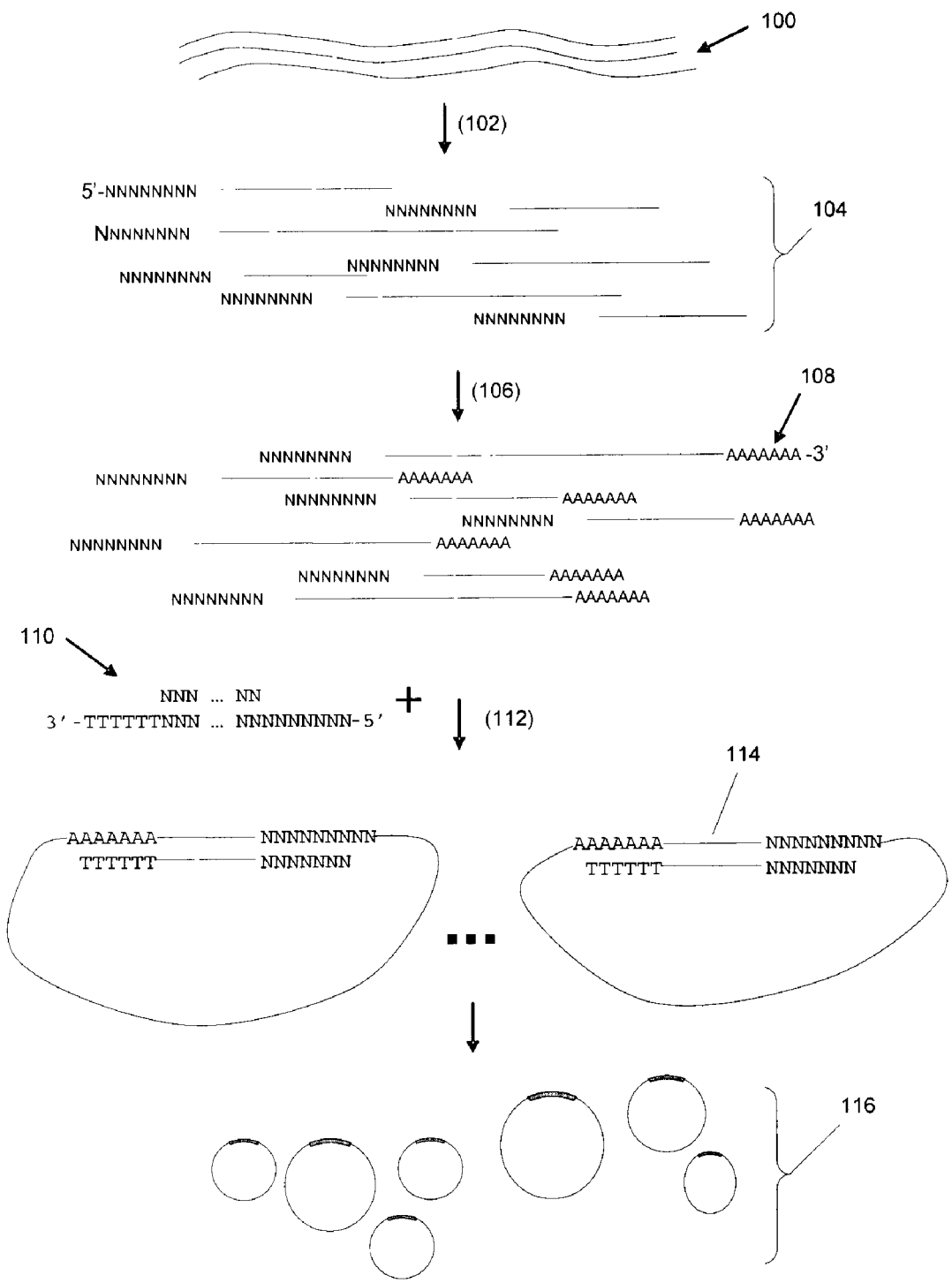
FIG. 1 illustrates an aspect of the preparation of circular polynucleotides for use the in the various embodiments of the invention.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells. A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis. A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Overview

The invention provides random arrays and methods for creating and using random arrays for large-scale parallel analyses of populations of target polynucleotides, such as RNAs, genomic DNA fragments, or the like. In one aspect, each element of an array of the invention comprises copies of a single target polynucleotide where such copies are made in at least two stages of amplification. In one aspect, a first stage of amplification is carried out in solution by circularizing target polynucleotides and replicating them by rolling circle replication to create concatemers, after which a second stage of amplification is carried out either in solution or in situ after deposition of the concatemers (also referred to herein as "first stage amplicons") on a surface. In another aspect, second stage is performed partially in solution and partially in situ. In another aspect, each amplicon of an array comprises copies of a plurality of target polynucleotides wherein the copies of each member of the plurality are made in solution and subsequently attached to the array surface. Preferably, such pluralities are in the range of from about 2 to about 50 and may be the same or different for different elements of an array.

Generally, amplicons of target polynucleotides are attached to a compact or restricted area on a surface, thereby intensifying signals that result from sequencing and other reactions conducted upon the attached amplicons. Amplicons of target polynucleotides may be bound to a surface in a variety of ways. Usually, attachment is by several bonds and may be covalent or non-covalent. Non-covalent bonds include formation of duplexes between capture oligonucleotides on the surface and complementary sequences in the target polynucleotide and/or its amplicon, and adsorption to a surface by attractive noncovalent interactions, such as Van der Waal forces, hydrogen bonding, ionic and hydrophobic interactions, and the like. As used herein, "duplex" generally means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that a pair of nucleotides in the duplex fails to undergo Watson-Crick bonding.

Multi-valent covalent bonding may be accomplished, as described more fully below, by providing reactive functionalities on the surface that can reactive with a plurality of complementary functionalities in the amplicon of the target polynucleotides.

As mentioned above, in one aspect, target polynucleotides of the invention undergo a first stage of amplification in solution and then are disposed randomly on a surface of a support material, after which the disposed first stage amplicons undergo a second stage of in situ amplification. Thus, in one aspect, target polynucleotides are distributed on a surface in close approximation to a Poisson distribution for individually detectable target polynucleotides. In a preferred aspect, the target polynucleotides are distributed in a format that provides for optical resolvability of at least 30%, more preferably at least 50%, even more preferably at least 70% of the individual target polynucleotides. In another aspect, amplicons of target polynucleotides are disposed on a surface that contains discrete regions within which amplicons are attached. Preferably, amplicons, preparation methods, and areas of such discrete regions are selected so that substantially all such regions contain at most only a single kind of target polynucleotide.

Compositions/Structures of Target Polynucleotides

The present invention provides compositions and methods that are derived from and/or utilize target polynucleotides from samples. As will be appreciated by those in the art, the sample solution may comprise any number of things, including, but not limited to, bodily fluids (including, but not limited to, blood, urine, serum, lymph, saliva, anal and vaginal secretions, perspiration and semen) and cells of virtually any organism, with mammalian samples being preferred and human samples being particularly preferred; environmental samples (including, but not limited to, air, agricultural, water and soil samples); biological warfare agent samples; research samples (i.e. in the case of nucleic acids, the sample may be the products of an amplification reaction, including both target and signal amplification, such as PCR amplification reactions; purified samples, such as purified genomic DNA, RNA preparations, raw samples (bacteria, virus, genomic DNA, etc.). In accordance with the present invention, samples may be subjected to virtually any experimental manipulation.

In general, cells from a target organism (animal, avian, mammalian, etc.) are used. When genomic DNA is used, the amount of genomic DNA required for constructing arrays and substrates of the invention can vary widely. In one aspect, for mammalian-sized genomes, fragments are generated from at least about 1 genome-equivalent of DNA; and in another aspect, fragments are generated from at least about 10 genome-equivalents of DNA; and in another aspect, fragments are generated from at least about 30 genome-equivalents of DNA. Target polynucleotides of the invention are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below (for example in the construction of primers and probes such as label probes), nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with bicyclic structures including locked nucleic acids, Koshkin et al., J. Am. Chem. Soc. 120:13252 3 (1998); positive backbones (Denpcy et al., Proc. Natl. Acad. Sci. USA 92:6097 (1995); non-ionic backbones (U.S. Pat. Nos. 5,386, 023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. All of these references are hereby expressly incorporated by reference. Modifications of the ribose-phosphate backbone may be made to increase the stability and half-life of such molecules in physiological environments. For example, PNA:DNA hybrids can exhibit higher stability and thus may be used in some embodiments.

The nucleic acids may be single stranded or double stranded, as specified, or contain portions of both double stranded or single stranded sequence. The nucleic acids may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine, hypoxathanine, isocytosine, isoguanine, etc.

"Target polynucleotides" and "target nucleic acids" comprise "target sequences". As used herein, "target sequence" refers generally to a nucleic acid sequence on a single strand of nucleic acid. The target sequence may be a portion of a gene, a regulatory sequence, genomic DNA, cDNA, RNA including mRNA and rRNA, or others. As is outlined herein, the target sequence may be a target sequence from a sample, or a secondary target such as a product of an amplification reaction, a fragmentation reaction, and the like. A target sequence may be of any length. A target sequence often comprises a fragment of a target polynucleotide, and the length of that fragment may comprise some or all of the target polynucleotide from which it is derived. For a target sequence or a polynucleotide fragment to be "derived" from a target polynucleotide (or any polynucleotide) can mean that the target sequence/polynucleotide fragment is formed by physically, chemically, and/or enzymatically fragmenting a target polynucleotide (or any other polynucleotide). To be "derived" from a polynucleotide may also mean that the fragment is the result of a replication or amplification of a particular subset of the nucleotide sequence of the target polynucleotide.

The target sequence may also include a number of target domains, and these target domains may include the same or different sequences. For example, a first target domain of the sample target sequence may hybridize to a capture probe and a second target domain may hybridize to a label probe, etc. The target domains may be adjacent or separated as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In one embodiment, methods and compositions of the invention use genomic DNA, particular human genomic DNA. Genomic DNA is obtained using conventional techniques, for example, as disclosed in Sambrook et al., supra, 1999; Current Protocols in Molecular Biology, Ausubel et al., eds. (John Wiley and Sons, Inc., NY, 1999), or the like. In a preferred embodiment, isolated genomic DNA is free of DNA processing enzymes and contaminating salts, represents the entire genome equally, and comprises DNA fragments with lengths from about 1,000 to about 100,000 base pairs in length.

Adaptors

The invention preferably includes adaptors at spaced locations within a target polynucleotide or a fragment of a polynucleotide. Such adaptors may serve as platforms for interrogating adjacent sequences using various sequencing chemistries, such as those that identify nucleotides by primer extension, probe ligation, and the like. That is, one unique component of some embodiments of the invention is the insertion of known adaptor sequences into target polynucleotides, such that there is an interruption of contiguous target sequences with the adaptors. By sequencing both "upstream" and "downstream" of the adaptor, sequence information of entire target sequences may be accomplished. Adaptors can also be used in accordance with the invention to circularize polynucleotides.

Adaptors can be added to the ends of polynucleotide molecules—such adaptors are also referred to herein as "end adaptors". Adaptors can also be "interspersed adaptors", meaning that these adaptors are inserted into the "interior" of a polynucleotide molecule—i.e., interspersed adaptors separate two regions of a polynucleotide molecule, as described in U.S. application Ser. No. 11/679,124, which is hereby incorporated by reference. The adaptor may separate regions that are contiguous in the original polynucleotide or in the original genomic sequence from which the polynucleotide is derived. In another aspect, the adaptor may separate target sequence regions with known approximate or exact distance, including distance information for variations including bases deleted, repeated, etc.

In accordance with the invention, adaptors can include multiple features. Such features can include without limitation restriction endonuclease recognition sites, anchor probe hybridization sites (for use in analysis), sequencing probe hybridization sites, capture probe hybridization sites, and polymerase recognition sequences. Polynucleotide molecules that include adaptors with capture probe hybridization sites can be immobilized on a surface that contains capture probes through hybridization of the capture probes with the adaptors containing complementary capture probe hybridization sites.

In a preferred embodiment, adaptors include recognition sites for type IIs restriction endonucleases. Exemplary type IIs restriction endonucleases include, but are not limited to, Eco57M I, Mme I, Acu I, Bpm I, BceA I, Bbv I, BciV I, BpuE I, BseM II, BseR I, Bsg I, BsmF I, BtgZ I, Eci I, EcoP15 I, Eco57M I, Fok I, Hga I, Hph I, Mbo II, Mnl I, SfaN I, TspDT I, TspDW I, Taq II, and the like.

In some embodiments, each adaptor comprises the same Type IIs restriction endonuclease site. In alternative embodiments, different adaptors comprise different sites. In specific embodiments, one or more of the adaptors comprises two or more Type IIs restriction endonuclease sites, for use in bi-directional cutting or to provide additional specificity when introducing multiple adaptors.

In one embodiment of the invention, an adaptor can comprise a primer binding sequence. This primer binding sequence may be used, for example, to bind a primer for a polymerase. As is known in the art, in order to replicate a template, polymerases generally require a single stranded template (concatemers of the invention, for example), wherein the single stranded template includes a portion of double stranded nucleic acid. Essentially, any sequence can serve as a primer binding sequence to bind a primer, because any double stranded sequence will be recognized by the polymerase. In general, the primer binding sequence is from about 3 to about 60 nucleotides in length, with from about 15 to about 25 being preferred. Primer oligonucleotides are usually 6 to 25 bases in length. As will be appreciated by those in the art, the primer binding sequence can be contained within any other part of adaptor sequences. The primer binding sequence will hybridize to a complementary sequence on a primer, thus forming the requisite double stranded region for a polymerase to recognize and then replicate the remainder of the single stranded template.

In accordance with the invention, an adaptor can also comprise a capture probe recognition sequence. As is more fully outlined below, one embodiment of the invention utilizes capture probes on the surface of a substrate to immobilize polynucleotide molecules. The term "polynucleotide molecules" includes polynucleotides, target polynucleotides, target sequences and can also include other components such as adaptors. In one embodiment, the polynucleotide molecules include adaptors which comprise a domain sufficiently complementary to one or more capture probes to allow hybridization of the domain and the capture probe, resulting in immobilization of the polynucleotide molecule on the surface.

In one aspect, an adaptor comprises a secondary structure sequence. In a preferred aspect, adaptors include palindromic sequences or sequences complementary between adaptors, which foster intramolecular interactions within the target polynucleotide. For example, palindromic or complementary sequences in a plurality of adaptors within the concatemer can result in hybridization between adaptors (e.g., intramolecular interactions between copies in the concatemer) or within the adaptor itself e.g., resulting in hairpins. These structures can serve to "tighten" the three dimensional structure of the polynucleotide. In the case of concatemers formed from polynucleotides comprising adaptors, which are described in further detail below, palindromic or complementary sequences within the adaptors can provide a secondary structure that results in a more compact spheroid shape. These palindromic and/or complementary sequence units can be 5, 6, 7, 8, 9, 10 or more nucleotides in length and can be designed using a variety of different sequences. In one embodiment, palindromic sequences can be chosen to provide a specific melting temperature. In one exemplary embodiment, a palindrome AAAAAAATTTTTTT (SEQ ID NO: 8) will form a 14 base dsDNA hybrid with a neighboring unit that includes the complementary palindrome TTTTTTTAAAAAAA (SEQ ID NO: 9), resulting in a "local" region of double stranded DNA within the secondary structure of a single stranded polynucleotide molecules, such as a concatemer.

In one embodiment, an adaptor can comprise one or more binding sequences for a detectable tag, such as a label probe. In some embodiments, label probes can be added to the concatemers to detect particular sequences. Label probes will hybridize to the label probe binding sequence and comprise at least one detectable label. Such labels include without limitation the direct or indirect attachment of radioactive moieties, fluorescent moieties, calorimetric moieties, chemiluminescent moieties, and the like. Many comprehensive reviews of methodologies for labeling DNA and constructing DNA adaptors provide guidance applicable to constructing oligonucleotide probes of the present invention. Such reviews include Kricka, Ann, Clin. Biochem., 39: 114-129 (2002); Schaferling et al, Anal. Bioanal. Chem., (Apr. 12, 2006); Matthews et al, *Anal. Biochem.*, Vol 169, pgs. 1-25 (1988); Haugland, Handbook of Fluorescent Probes and Research Chemicals, Tenth Edition (Invitrogen/Molecular Probes, Inc., Eugene, 2006); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227-259 (1991); Hermanson, Bioconjugate Techniques (Academic Press, New York, 1996); and the like. Many more particular methodologies applicable to the invention are disclosed in the following sample of references: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115-6128 (1986)(enzyme-oligonucleotide conjugates); Ju et al, Nature Medicine, 2: 246-249 (1996); Bawendi et al, U.S. Pat. No. 6,326,144 (derivatized fluorescent nanocrystals); Bruchez et al, U.S. Pat. No. 6,274,323 (derivatized fluorescent nanocrystals); and the like.

In one embodiment, an adaptor can comprise one or more tagging sequences. In this embodiment, tagging sequences may be used to isolate and/or purify circularized target polynucleotides and concatemers from a mixture. In some embodiments, tagging sequences may include unique nucleic acid sequences that can be utilized to identify the origin of target sequences in mixtures of tagged samples, or can include components of ligand binding pairs, such as biotin/streptavidin, etc.

In one aspect, multiple adaptors are included within a target polynucleotide or any other polynucleotide molecule. In one aspect, interspersed adaptors each have a length in the range of from about 4 to about 4000 nucleotides. In one embodiment, the interspersed adaptors have a length of from about 8 to about 60 nucleotides; in another embodiment, they have a length in the range of from 8 to 32 nucleotides; in embodiment aspect, they have a length in a range selected from about 4 to about 400 nucleotides; from about 10 to about 100 nucleotides, from about 400 to about 4000 nucleotides, from about 10 to about 80 nucleotides, from about 20 to about 70 nucleotides, from about 30 to about 60 nucleotides, and from about 4 to about 10 nucleotides. In a particularly preferred embodiment, interspersed adaptors with length from about 20 to about 30 bases are used in accordance with the invention.

The number of interspersed adaptors inserted into target polynucleotides may vary widely and depends on a number of factors, including the sequencing/genotyping chemistry being used (and its read-length capacity), the particular length of the cleavage site of a particular Type IIs site, the number of nucleotides desired to be identified within each target polynucleotide, whether amplification steps are employed between insertions, and the like.

In one aspect, a plurality of interspersed adaptors is inserted at separate sites of a target polynucleotide; this may include two, three, four or more interspersed adaptors that are inserted within the target polynucleotide. Alternatively, the number of interspersed adaptors inserted into a target polynucleotide ranges from 2 to 10; from 2 to 4; from 3 to 6; from 3 to 4; and from 4 to 6. In another aspect, interspersed adaptors may be inserted in one or both polynucleotide segments of a longer polynucleotide, e.g., 0.4-4 Kb in length, that have been ligated together directly or indirectly in a circularization operation (referred to herein as a "mate-pair"). In one aspect, such polynucleotide segments may be 4-400 (preferably 10-100) bases long.

It should also be noted that in general, the first adaptor attached to a target sequence is not "interspersed" or "inserted". That is, the first adaptor is generally attached to one terminus of the fragmented target sequence, and the subsequent adaptors are interspersed within a contiguous target sequence.

Interspersed adaptors may in accordance with the invention be single or double stranded.

In some embodiments, adaptors can be used to create "classes" of polynucleotides. By "classes" is meant groups of polynucleotides that share a common feature—for example, such features can include source/sample of origin, length, amount of processing (including circularization, deletion, further fragmentation), as well as any other feature by which a particular group of polynucleotides can be differentiated from another group of polynucleotides. In one aspect, each member of a group of target polynucleotides has an adaptor with an identical anchor probe binding site and type IIs recognition site attached to a DNA fragment from source nucleic acid. In another embodiment, classes of polynucleotides may be created by providing adaptors having different anchor probe binding sites. Such classes may be created by providing adaptors having distinct sequences or features to differentiate among polynucleotides from different classes. For example, adaptors can comprise different anchor probe binding sites. This type of "clustering" can increase the efficiency of identifying and analyzing sequence information of the target polynucleotides.

In one embodiment, if a polynucleotide is "associated with" an adaptor, this can mean that the target polynucleotide is identified as being part of a "class" as discussed above. To be associated with an adaptor also generally refers to aspects of the invention in which an adaptor can be used to identify or tag a polynucleotide.

Interspersed adaptors are nucleic acid sequences that are inserted at spaced locations within the interior region of a target polynucleotide. In one aspect, "interior" in reference to a target polynucleotide means a site internal to a target polynucleotide prior to processing, such as circularization and cleavage, that may introduce sequence inversions, or like transformations, which disrupt the ordering of nucleotides within a target polynucleotide. In one very specific aspect, interspersed adaptors are inserted at intervals within a contiguous region of a target polynucleotide. In some cases, such intervals have predetermined lengths, which may or may not be equal. In other cases, the spacing between interspersed adaptors may be known only to an accuracy of from one to a few nucleotides (e.g., from 1 to 15), or from one to a few tens of nucleotides (e.g., from 10 to 40), or from one to a few hundreds of nucleotides (e.g., from 100 to 200). In some cases about 1 to 4 bases of target polynucleotide may be deleted or duplicated in the process of adapter insertion. Preferably, the ordering and number of interspersed adaptors within each target polynucleotide is known. In some aspects of the invention, interspersed adaptors are used together with adaptors that are attached to the ends of target polynucleotides.

Circularizing Polynucleotide Molecules

In a preferred aspect, polynucleotides and portions of polynucleotides are ligated to adaptors and then circularized as preparation for use in other aspects of the invention described herein. Although many of the embodiments described herein refer to "polynucleotides" and "polynucleotide molecules", these descriptions also apply to all other polynucleotide molecules described herein, including "target polynucleotides", "target sequences", "concatemers", "target nucleic acids", "nucleic acids", "DNA nanoballs" and the like.

In one aspect, circularization of polynucleotide molecules can generally be described as follows (it should be noted that genomic DNA is used as an example herein, but is not meant to be limiting). Genomic DNA from any organism is isolated and fragmented into target polynucleotides using standard techniques. A first adaptor is ligated to one terminus of the target polynucleotide. The adaptor preferably comprises a Type IIs restriction endonuclease site, which cuts outside of the recognition sequence. If the enzyme results in a "sticky" end, the overhang portion can either be filled in or removed.

In one embodiment, an enzyme is used to ligate the two ends of the linear strand comprising the adaptor and the target polynucleotide to form a circularized nucleic acid. This may be done using a single step. Alternatively, a second adaptor can be added to the other terminus of the target polynucleotide (for example, a polyA tail), and then a bridging sequence can be hybridized to the two adaptors, followed by ligation. In either embodiment, a circular sequence is formed.

The circular sequence is then cut with the Type IIs endonuclease, resulting in a linear strand, and the process is repeated. This results in a circular polynucleotide with adaptors interspersed at well defined locations within previously contiguous target sequences.

If double stranded DNA is used, then the ends of the fragments may be prepared for circularization by "polishing" and optional ligation of adaptors using conventional techniques, such as employed in conventional shotgun sequencing, e.g., Bankier, Methods Mol. Biol., 167: 89-100 (2001); Roe, Methods Mol. Biol., 255: 171-185 (2004), which is hereby incorporated by reference.

In a preferred embodiment, target polynucleotide fragments of about 0.2 to about 2 kb in size are used in a circularization reaction. In a more preferred embodiment, the fragments are from about 0.3 to about 0.6 kb in size.

In one embodiment, "adaptor segments" are used to circularize polynucleotides. In this embodiment, one portion of an adaptor is ligated to one end of a polynucleotide molecule and the remaining portion is ligated to the other end. The polynucleotide molecule is then circularized by ligating the two portions of the adaptor (the "adaptor segments") to form a whole adaptor.

In one aspect, the invention utilizes a method of circularization as illustrated in FIG. 1. After genomic DNA (100) is fragmented and denatured (102), single stranded DNA fragments (104) are first treated with a terminal transferase (106) to attach a poly dA tails (108) to 3-prime ends. This is then followed by ligation (112) of the free ends intra-molecularly with the aid of a bridging oligonucleotide (110) that is complementary to the poly dA tail at one end and complementary to any sequence at the other end by virtue of a segment of degenerate nucleotides. A duplex region (114) of the bridging oligonucleotide (110) contains at least a primer binding site for RCR and, in some embodiments, comprises sequences that provide complements to a capture probe, which may be the same or different from the primer binding site sequence, or which may overlap with the primer binding site sequence. The length of capture probe may vary widely, In one aspect, capture probes and their complements in a bridging oligonucleotide have lengths in the range of from 10 to 100 nucleotides; and more preferably, in the range of from 10 to 40 nucleotides. Circular products (116) may be conveniently isolated by a conventional purification column, digestion of non-circular DNA by one or more appropriate exonucleases, or both.

In some aspects, the duplex region (114) may contain additional elements, such as an oligonucleotide tag, for example, for identifying the source nucleic acid from which its associated DNA fragment came. That is, in specific methods, circles or adaptor ligation or concatemers from different source nucleic acids may be prepared separately during which a bridging adaptor containing a unique tag is used, after which they are mixed for concatemer preparation or application to a surface to produce a random array. The associated fragments may be identified on such a random array by hybridizing a labeled tag complement to its corresponding tag sequences in the concatemers, or by sequencing the entire adaptor or the tag region of the adaptor.

In certain aspects of the embodiments, DNA circles prepared from source nucleic acid need not include an adaptor oligonucleotide. These circularized products can be used directly in the preparation of concatemers, as described in more detail herein.

Polynucleotide fragments can also be circularized using circularizing enzymes, such as CircLigase, a single stranded DNA ligase that circularizes single stranded DNA without the need of a template. CircLigase is used in accordance with the manufacturer's instructions (Epicentre, Madison, Wis.). In a preferred embodiment, single stranded polynucleotide circles comprising a DNA fragment and one or more adaptors are formed by using a standard ligase (such as T4 ligase) to ligate an adaptor to one end of DNA fragment. CircLigase is then used to close the circle.

Concatemers

In one aspect, the invention provides target polynucleotides in the form of concatemers which contain multiple copies of a target polynucleotide or a fragment of a target polynucleotide. DNA concatemers under conventional conditions (a conventional DNA buffer, e.g., TE, SSC, SSPE, or the like, at room temperature) form random coils that roughly fill a spherical volume in solution having a diameter of from about 100 to 300 nm, which depends on the size of the DNA and buffer conditions, in a manner well known in the art, e.g., Drmanac et al., U.S. patent application Ser. No. 11/451,691; Drmanac et al., U.S. patent application Ser. No. 11,451,692; Edvinsson, "On the size and shape of polymers and polymer complexes," Dissertation 696 (University of Uppsala, 2002). Concatemers, particularly concatemers with a secondary structure such as a random coil, are also referred to herein as "DNA nanoballs" ("DNBs").

Target polynucleotides may be generated from a source nucleic acid, such as genomic DNA, cDNA (including cDNA libraries), cRNA (including cRNA libraries), siRNA (and siRNA libraries) and mRNA (as well as products of transcription and reverse to transcription). In a preferred embodiment, target polynucleotides are generated from source nucleic acid by fragmentation to produce fragments of one or more specific sizes. This fragmentation may be accomplished by methods known in the art, including chemical, enzymatic and mechanical fragmentation. In one embodiment, the fragments are from about 50 to about 2000 nucleotides in length. In another embodiment, the fragments are from 50 to 600 nucleotides in length. In another embodiment, the fragments are 300 to 600 or 200 to 2000 nucleotides in length. In yet another embodiment, the fragments are 10-100, 50-100, 50-300, 100-200, 200-300, 50-400, 100-400, 200-400, 400-500, 400-600, 500-600, 50-1000, 100-1000, 200-1000, 300-1000, 400-1000, 500-1000, 600-1000, 700-1000, 700-900, 700-800, 800-1000, 900-1000, 1500-2000, and 1750-2000 nucleotides in length. These fragments may in turn be circularized for use in an RCR reaction or in other biochemical processes, such as the insertion of additional adaptors.

Although many of the following descriptions focuses on DNA molecules, the invention is not limited to DNA polynucleotide molecules, and the following methods apply to other types of polynucleotides, including without limitation mRNA, siRNA, and cRNA.

In many cases, enzymatic digestion of the source nucleic acid, particularly genomic DNA, is not required because shear forces created during lysis and extraction will generate fragments in the desired range. In another embodiment, shorter fragments (1-5 kb) can be generated by enzymatic fragmentation using restriction endonucleases. In one embodiment, 10-100 genome-equivalents of DNA ensure that the population of fragments covers the entire genome. In some cases, it is advantageous to provide carrier DNA, e.g., unrelated circular synthetic double-stranded DNA, to be mixed and used with the sample DNA whenever only small amounts of sample DNA are available and there is danger of losses through nonspecific binding, e.g., to container walls and the like. In one embodiment, the DNA is denatured after fragmentation to produce single stranded fragments.

In addition to target polynucleotides or portions of target polynucleotides, concatemers of the invention in a preferred embodiment also include interspersed adaptors that permit acquisition of sequence information from multiple sites, either consecutively or simultaneously. In this embodiment, interspersed adaptors comprise hybridization sites for sequencing probes, allowing for detection and identification of nucleotides in adjacent detection positions at numerous points along the target polynucleotide molecule. Since interspersed adaptors are interspersed throughout the polynucleotide molecule, a long target polynucleotide can be sequenced using short sequence reads, because the sequencing reactions have multiple "starting points" in the multiple interspersed adaptors.

Figure 2:
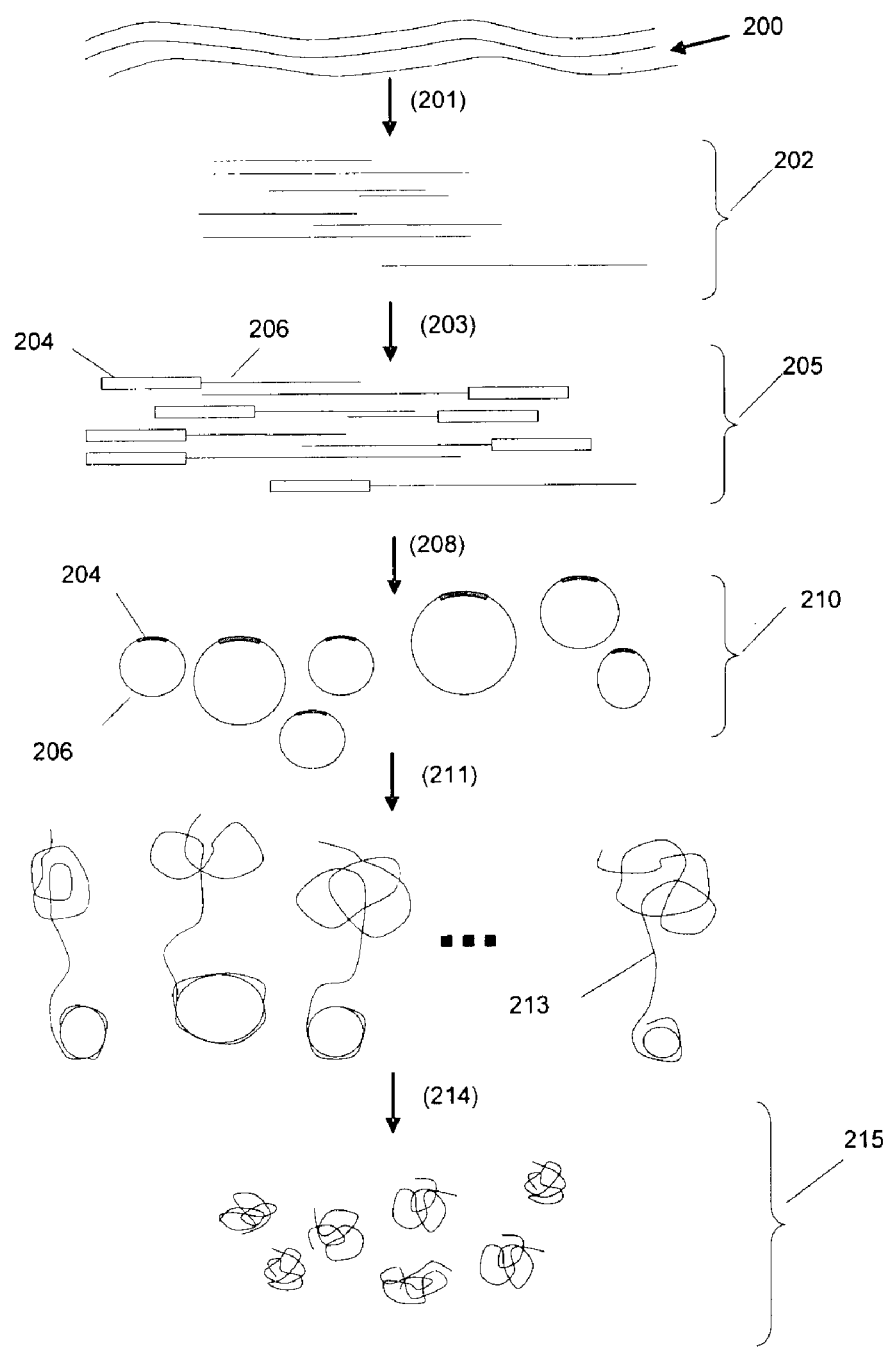
FIGS. 2 and 3 illustrate methods for generating concatemers.
Figure 3:
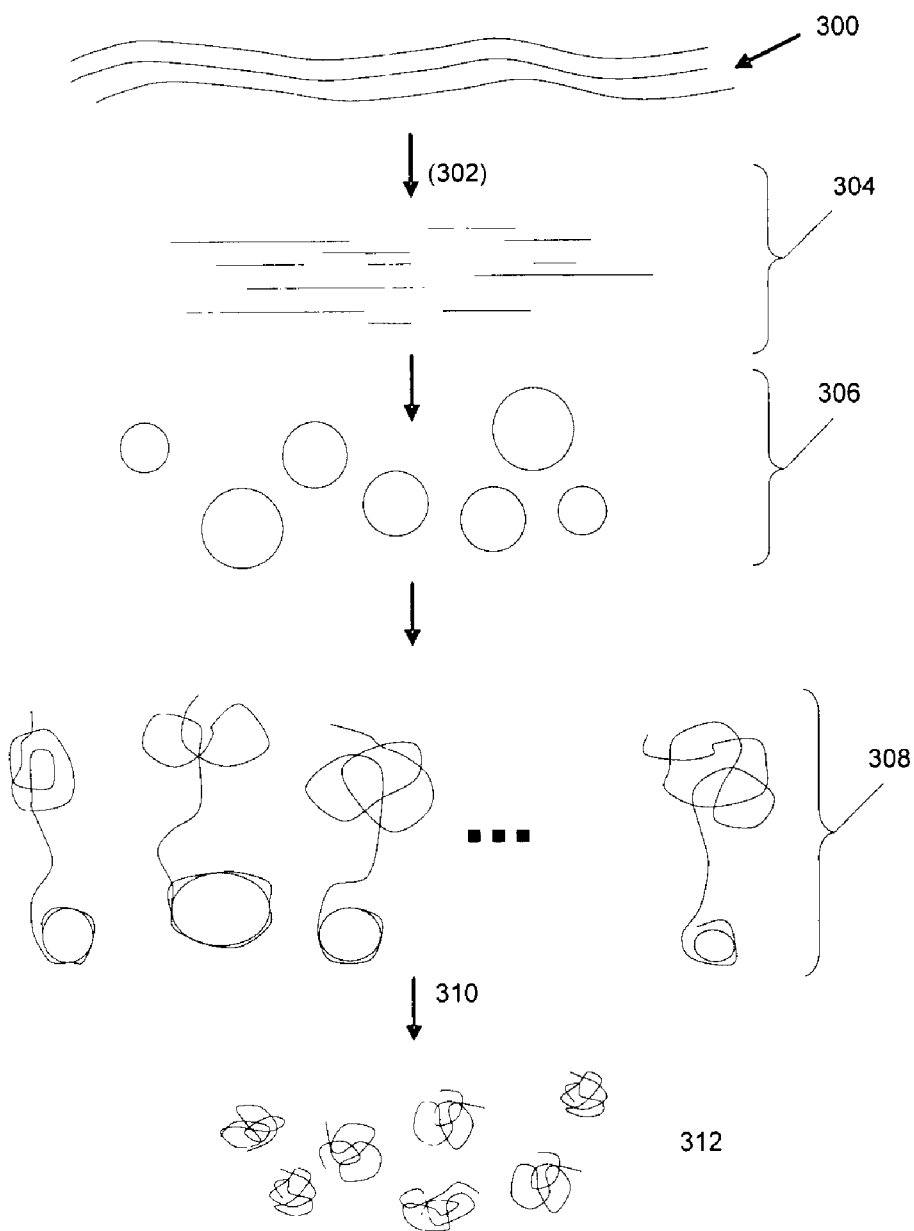

In a preferred aspect, rolling circle replication (RCR) is used to create concatemers of the invention. The RCR process has been shown to generate multiple continuous copies of the M13 genome. (Blanco, et al., (1989) *J Biol Chem* 264:8935-8940). In this system, as illustrated in FIGS. 2 and 3, the desired polynucleotide fragment is replicated by linear concatemerization. Guidance for selecting conditions and reagents for RCR reactions is available in many references available to those of ordinary skill, as evidence by the following, which are each incorporated by reference: Kool, U.S. Pat. No. 5,426,180; Lizardi, U.S. Pat. Nos. 5,854,033 and 6,143,495; Landegren, U.S. Pat. No. 5,871,921; and the like.

Generally, RCR reaction components include single stranded DNA circles, one or more primers that anneal to DNA circles, a DNA polymerase having strand displacement activity to extend the 3' ends of primers annealed to DNA circles, nucleoside triphosphates, and a conventional polymerase reaction buffer. Such components are combined under conditions that permit primers to anneal to DNA circle. Extension of these primers by the DNA polymerase forms concatemers of DNA circle complements.

Preferably, concatemers produced by RCR are approximately uniform in size; accordingly, in some embodiments, methods of making arrays of the invention may include a step of size-selecting concatemers. For example, in one aspect, concatemers are selected that as a population have a coefficient of variation in molecular weight of less than about 30%; and in another embodiment, less than about 20%. In one aspect, size uniformity is further improved by adding low concentrations of chain terminators, such ddNTPs, to the RCR reaction mixture to reduce the presence of very large concatemers, e.g., produced by DNA circles that are synthesized at a higher rate by polymerases. In one embodiment, concentrations of ddNTPs are used that result in an expected concatemer size in the range of from 50-250 Kb, or in the range of from 50-100 Kb. In another aspect, concatemers may be enriched for a particular size range using a conventional separation techniques, e.g., size-exclusion chromatography, membrane filtration, or the like.

The RCR process relies upon the desired target molecule first being formed into a circular substrate. This linear amplification uses the original DNA molecule, not copies of a copy, thus ensuring fidelity of sequence. As a circular entity, the molecule acts as an endless template for a strand displacing polymerase that extends a primer complementary to a portion of the circle. The continuous strand extension creates long, single-stranded DNA consisting of hundreds of concatemers comprising multiple copies of sequences complementary to the circle.

FIG. 2 illustrates one aspect of the embodiments for creating concatemers for use in the invention. In this embodiment, source nucleic acid (200) is treated (201) to form single stranded fragments (202), preferably in the range of from 50 to 600 nucleotides, and more preferably in the range of from 300 to 600 nucleotides. Individual fragments of source nucleic acid 206 are then ligated (203) to adaptors (204) to form a population of adaptor-fragment conjugates (205). Source nucleic acid (200) may be genomic DNA extracted from a sample using conventional techniques, or a cDNA or genomic library produced by conventional techniques, or synthetic DNA, or the like. Treatment (201) usually entails fragmentation by a conventional technique, such as chemical fragmentation, enzymatic fragmentation, or mechanical fragmentation, followed by denaturation to produce single stranded DNA fragments.

Adaptors (204), in this example, are used to form (208) a population (210) of DNA circles by the method illustrated in FIG. 2. In one aspect each member of population (210) has an adaptor with an identical primer binding site and a DNA fragment (206) from source nucleic acid (200). As discussed above, the adaptor also may have other functional elements including, but not limited to, tagging sequences, attachment sequences, palindromic sequences, restriction sites, functionalization sequences, and the like. In other embodiments, classes of DNA circles may be created by providing adaptors having different primer binding sites.

After DNA circles (210) are formed, a primer and rolling circle replication (RCR) reagents may be added to generate (211) in a conventional RCR reaction (212) concatemers (213) of the complements of the adaptor oligonucleotide and DNA fragments, which population can then be isolated using conventional separation techniques. Performing this for multiple circles (214) results in a population of concatemers (215) for further amplification in the construction of arrays of the invention, either in solution prior to the attachment to arrays or in situ following attachment of the concatemers to the arrays.

In a specific aspect, primers used for RCR may be selected to match target sequences within the DNA fragments rather than in the adaptor. In such an embodiment, the concatemers produced will produce a set of DNA circles which preferentially include these target sequences.

Alternatively, amplification of the circular nucleic acids may be implemented by successive ligation of short oligonucleotides, e.g., 6-mers, from a mixture containing all possible sequences, or if circles are synthetic, a limited mixture of these short oligonucleotides having selected sequences for circle replication, a process known as "rolling circle amplification" (RCA). Concatemers may also be generated by ligation of target DNA in the presence of a bridging template DNA complementary to both beginning and end of the target molecule. A population of different target DNA may be converted in concatemers by a mixture of corresponding bridging templates.

In a preferred embodiment, a subset of a population of DNA circles may be isolated based on a particular feature, such as a desired number or type of adaptor. This population can be isolated or otherwise processed (e.g., size selected) using conventional techniques, e.g., a conventional spin column, or the like, to form a population from which a population of concatemers can be created using techniques such as RCR.

As illustrated in FIG. 3, in certain embodiments, DNA circles prepared from source nucleic acid (300) need not include an adaptor oligonucleotide. As before, source nucleic acid (300) is fragmented and denatured (302) to form a population of single-stranded fragments (304), preferably in the size range of from about 50 to 600 nucleotides, and more preferably in the size range of from about 300 to 600 nucleotides, after which they are circularized in a non-template driven reaction with circularizing ligase, such as CircLigase (Epicentre Biotechnologies, Madison, Wis.), or the like. After formation of DNA circles (306), concatemers are generated by providing a mixture of primers that bind to selected sequences. The mixture of primers may be selected so that only a subset of the total number of DNA circles (306) generates concatemers. For example, primers can be selected to target certain exon sequences, thus enriching the population of DNA circles with these exon sequences. Primers used in this aspect may, as described herein, include a tail sequence. In one embodiment, the primers all share an identical tail sequence (also referred to herein as a "tail oligonucleotide"). In another embodiment, a group of tailed primers will include multiple different tail sequences. Generating concatemers for multiple circles results in a population of concatemers, and the desired concatemers isolated (310), resulting in a population of concatemers (312) for further amplification, either in solution prior to the attachment to arrays or in situ following attachment of the concatemers to the arrays.

In one aspect, once concatemers are immobilized to a surface, the primers can be extended using a non-strand displacing polymerase to form sets of copies of the concatemers that are individually attached to the surface, and the concatemer template can be removed to obtain single stranded DNA using hybridization methods known in the art. For example, removal can comprise without limitation, methods including: nicking the concatemer, cutting the concatemer using ssDNA nuclease or other enzyme at the gaps between two monomers of the concatemer, or, selective degradation of a single-stranded template. For example, if uracils are used in preparation of the concatemer, these uracils can be degraded to form the single stranded DNA. Any of these methods of removing the concatemer can be combined with DNA digestion by a 5' exonuclease, with denaturing agents, or with some combination thereof. Removing the concatemer after creating multiple copies of complementary sequences is particularly useful in aspects of the invention for target sequence analyses and other assays where multiple individually attached copies of the target polynucleotide are desirable.

Figure 4:
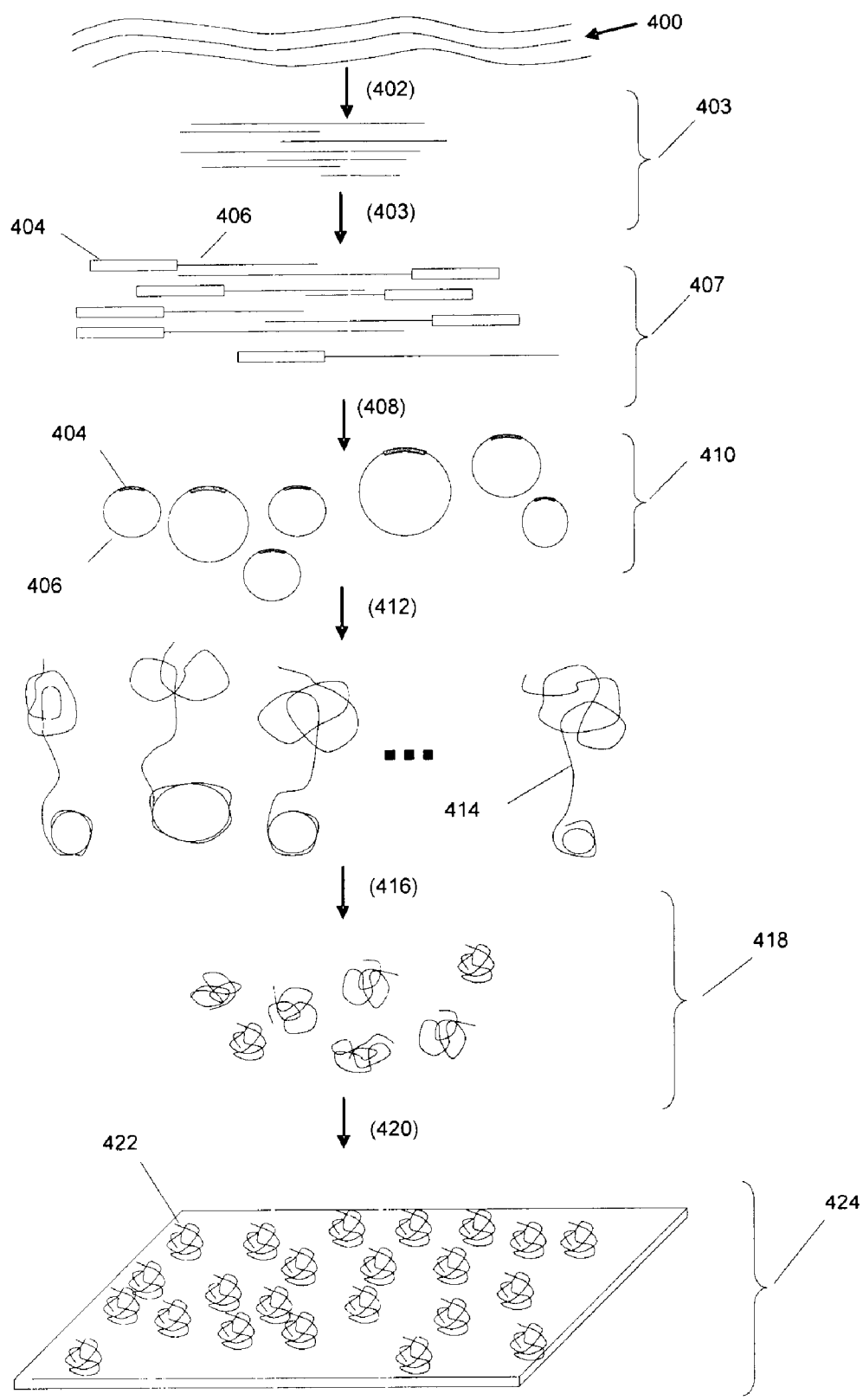
FIG. 4 illustrates a method for creating an array comprising first stage amplicons.

After concatemers are generated, e.g., using the above-described methods, they can be isolated and applied to surface for the formation of a random array of the invention. FIG. 4 illustrates the creation of concatemers and disposition of these concatemers onto arrays, where they can subsequently be amplified using the methods of the invention to create arrays of the invention. Source nucleic acids (400) are fragmented (403) and the individual fragments (406) are ligated (405) to adaptors (404) for circularization (408), after which the population of circularized nucleic acids (410) are formed (412) into concatemers (414) by RCR. The population of desired concatemers (418) are then isolated (416) and applied (420) to a surface (422) for creation of an array of first stage amplicons (424).

Methods of Amplification

Any polynucleotide molecules of the invention, including polynucleotides, target polynucleotides, target sequences, and concatemers, can be amplified using methods known in the art and described herein. Such methods of amplification can generally be accomplished in solution or in situ (i.e., on a surface).

Suitable amplification methods include both target amplification and signal amplification and include, but are not limited to, polymerase chain reaction (PCR), ligation chain reaction (sometimes referred to as oligonucleotide ligase amplification OLA), cycling probe technology (CPT), strand displacement assay (SDA), transcription mediated amplification (TMA), nucleic acid sequence based amplification (NASBA), rolling circle amplification (RCA), and invasive cleavage technology. All of these methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a target nucleic acid is added to a reaction mixture that comprises the necessary amplification components, and a modified primer is formed. Methods of amplification and detecting the products of amplification are discussed at length in U.S. Patent Publication No. 2006/0275782, which is hereby incorporated in its entirety for all purposes.

The methods of amplification described in this and following sections are often preludes to sequencing reactions, and often sequencing reactions incorporate an amplification step, as is also described further herein.

Strand Displacement Amplification

Strand displacement amplification (SDA) is generally described in Walker et al., in Molecular Methods for Virus Detection, Academic Press, Inc., 1995, and U.S. Pat. Nos. 5,455,166 and 5,130,238, all of which are hereby incorporated by reference.

In general, SDA may be described as follows. A single stranded target nucleic acid, usually a DNA target sequence, is contacted with an SDA primer. An "SDA primer" generally has a length of 25-100 nucleotides, with SDA primers of approximately 35 nucleotides being preferred. An SDA primer is substantially complementary to a region at the 3' end of the target sequence, and the primer has a sequence at its 5' end (outside of the region that is complementary to the target) that is a recognition sequence for a restriction endonuclease, sometimes referred to herein as a "nicking enzyme" or a "nicking endonuclease. The SDA primer then hybridizes with the target sequence. The SDA reaction mixture also contains a polymerase (an "SDA polymerase) and a mixture of all four deoxynucleoside-triphosphates (also called deoxynucleotides or dNTPs, i.e. dATP, dTTP, dCTP and dGTP), at least one species of which is a substituted or modified dNTP; thus, the SDA primer is modified, i.e. extended, to form a modified primer, sometimes referred to herein as a "newly synthesized strand". The substituted dNTP is modified such that it will inhibit cleavage in the strand containing the substituted dNTP but will not inhibit cleavage on the other strand. Examples of suitable substituted dNTPs include, but are not limited, 2'-deoxyadenosine 5'-O-(1-thiotriphosphate), 5-methyldeoxycytidine 5'-triphosphate, 2'-deoxyuridine 5'-triphosphate, and 7-deaza-2'-deoxyguanosine 5-triphosphate. In addition, the substitution of the dNTP may occur after incorporation into a newly synthesized strand; for example, a methylase may be used to add methyl groups to the synthesized strand. In addition, if all the nucleotides are substituted, the polymerase may have 5'-3' exonuclease activity. However, if less than all the nucleotides are substituted, the polymerase preferably lacks 5'-3' exonuclease activity.

As will be appreciated by those in the art, the recognition site/endonuclease pair can be any of a wide variety of known combinations. The endonuclease is chosen to cleave a strand either at the recognition site, or either 3' or 5' to it, without cleaving the complementary sequence, either because the enzyme only cleaves one strand or because of the incorporation of the substituted nucleotides. Suitable recognition site/endonuclease pairs are well known in the art; suitable endonucleases include, but are not limited to, HincII, HindIII, AvaI, Fnu4HI, TthIIII, NcII, BstXI, BamHI, etc. A chart depicting suitable enzymes, and their corresponding recognition sites and the modified dNTP to use is found in U.S. Pat. No. 5,455,166, hereby expressly incorporated by reference.

Once nicked, a polymerase (an "SDA polymerase") is used to extend the newly nicked strand, 5'-3', thereby creating another newly synthesized strand. The polymerase chosen should be able to initiate 5'-3' polymerization at a nick site, should also displace the polymerized strand downstream from the nick, and should lack 5'-3' exonuclease activity (this may be additionally accomplished by the addition of a blocking agent). Thus, suitable polymerases in SDA include, but are not limited to, the Klenow fragment of DNA polymerase I, SEQUENASE 1.0 and SEQUENASE 2.0 (U.S. Biochemical), T5 DNA polymerase and Phi29 DNA polymerase.

In one aspect, the invention provides methods of making a complex of copies of a polynucleotide molecule. In this aspect, a polynucleotide is amplified into a concatemer using RCR, resulting in a single stranded concatemer. Multiple copies of a second primer is then bound to the concatemer to initiate another round of DNA synthesis using a strand-displacing polymerase, which results in a complex of copies comprising partially displaced strands. In this embodiment, the original polynucleotide is generally a circular molecule comprising one or more adaptors. In a further embodiment, the primers used to initiate DNA synthesis are complementary or identical to a sequence of the one or more adaptors.

Cycling Probe Technology

Cycling probe technology (CPT) is a nucleic acid detection system based on signal or probe amplification rather than target nucleic acid amplification, such as is done in polymerase chain reactions (PCR). Cycling probe technology relies on a molar excess of labeled probe which contains a scissile linkage of RNA. Upon hybridization of the probe to the target, the resulting hybrid contains a portion of RNA:DNA. This area of RNA:DNA duplex is recognized by RNAseH and the RNA is excised, resulting in cleavage of the probe. The probe now consists of two smaller sequences which may be released, thus leaving the target intact for repeated rounds of the reaction. The unreacted probe is removed and the label is then detected. CPT is generally described in U.S. Pat. Nos. 5,011,769, 5,403,711, 5,660,988, and 4,876,187, and PCT published applications WO 95/05480, WO 95/1416, and WO 95/00667, all of which are specifically incorporated herein by reference.

Branched DNA Signal Amplification

"Branched DNA" signal amplification relies on the synthesis of branched nucleic acids, containing a multiplicity of nucleic acid "arms" that function to increase the amount of label that can be put onto one probe. This technology is generally described in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference.

Dendrimers

Similarity, dendrimers of nucleic acids serve to vastly increase the amount of label that can be added to a single molecule, using a similar idea but different compositions. This technology is as described in U.S. Pat. No. 5,175,270.

Polymerase Chain Reaction Amplification

In one embodiment, the amplification technique is PCR. The polymerase chain reaction (PCR) is widely used and described, and involves the use of primer extension combined with thermal cycling to amplify a target sequence; see U.S. Pat. No. 4,683,195 and, and PCR Essential Data, J. W. Wiley & sons, Ed. C. R. Newton, 1995, all of which are incorporated by reference. In addition, there are a number of variations of PCR which also find use in the invention, including "quantitative competitive PCR" or "QC-PCR", "arbitrarily primed PCR" or "AP-PCR", "immuno-PCR", "Alu-PCR", "PCR single strand conformational polymorphism" or "PCR-SSCP", "reverse transcriptase PCR" or "RT-PCR", "biotin capture PCR", "vectorette PCR", "panhandle PCR", and "PCR select cDNA subtraction", "allele-specific PCR", among others. In some embodiments, PCR is not preferred.

Nucleic Acid Sequence Based Amplification and Transcription Mediated Amplification Nucleic acid sequence based amplification (NASBA) is generally described in U.S. Pat. No. 5,409,818 and "Profiting from Gene-based Diagnostics", CTB International Publishing Inc., N.J., 1996, both of which are incorporated by reference. NASBA is very similar to both TMA and QBR. Transcription mediated amplification (TMA) is generally described in U.S. Pat. Nos. 5,399,491, 5,888,779, 5,705,365, 5,710,029, all of which are incorporated by reference. The main difference between NASBA and TMA is that NASBA utilizes the addition of RNAse H to effect RNA degradation, and TMA relies on inherent RNAse H activity of the reverse transcriptase.

In general, these techniques involve the use of three enzymes: reverse transcriptase, T7 RNA polymerase, and RNase H; and the final amplification product is single-stranded RNA with a polarity opposite that of the target. The amplified RNA product can be detected using methods known in the art, for example through the use of a target-specific capture probe bound to magnetic particles in conjunction with a ruthenium-labeled detector probe and an instrument (NucliSens Reader; bioMérieux) capable of measuring electrochemiluminescence (ECL). Alternatively, polynucleotides amplified by NASBA can specifically be detected in real time through the use of molecular beacon probes included in the amplification reaction. Molecular beacon probes possess a 5' fluorescent dye and a 3' quencher molecule (typically, 4-dimethylaminophenylazobenzoyl [DABCYL]) and are designed to form stem-loop structures that bring into close proximity the 5' and 3' ends of the probe, resulting in minimal fluorescence. In the presence of a complementary target sequence, the probe will hybridize to the target, separating the reporter dye from the quencher, resulting in a measurable increase in fluorescence. These techniques generally result in a single starting RNA template generating a single DNA duplex. This DNA duplex results in the creation of multiple RNA strands, which can then be used to initiate the reaction again, and amplification thus proceeds rapidly.

Single Base Extension (SBE)

In a preferred embodiment, single base extension (SBE; sometimes referred to as "minisequencing") is used for amplification. It should also be noted that SBE finds use in sequencing and genotyping applications, as is described below. Briefly, SBE is a technique that utilizes an extension primer that hybridizes to the target nucleic acid. A polymerase (generally a DNA polymerase) is used to extend the 3' end of the primer with a nucleotide analog labeled a detection label as described herein. Based on the fidelity of the enzyme, a nucleotide is only incorporated into the extension primer if it is complementary to the adjacent base in the target strand. Generally, the nucleotide is derivatized such that no further extensions can occur, so only a single nucleotide is added. However, for amplification reactions, this may not be necessary. Once the labeled nucleotide is added, detection of the label proceeds as described herein. See generally Sylvanen et al., Genomics 8:684-692 (1990); U.S. Pat. Nos. 5,846,710 and 5,888,819; Pastinen et al., Genomics Res. 7(6):606-614 (1997); all of which are expressly incorporated herein by reference.

Oligonucleotide Ligation Amplification (OLA)

In one embodiment, OLA is used to amplify polynucleotide molecules. OLA is referred to as the ligation chain reaction (LCR) when two-stranded substrates are used, involves the ligation of two smaller probes into a single long probe, using the target sequence as the template. In LCR, the ligated probe product becomes the predominant template as the reaction progresses. The method can be run in two different ways; in a first embodiment, only one strand of a target sequence is used as a template for ligation; alternatively, both strands may be used. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; WO 97/31256; and WO 89/09835, and U.S. Ser. Nos. 60/078,102 and 60/073,011, all of which are orated by reference.

In a preferred embodiment, the single-stranded target sequence comprises a first target domain and a second target domain, which are adjacent and contiguous. A first OLA primer and a second OLA primer nucleic acids are added, that are substantially complementary to their respective target domain and thus will hybridize to the target domains. These target domains may be directly adjacent, i.e. contiguous, or separated by a number of nucleotides. If they are non-contiguous, nucleotides are added along with means to join nucleotides, such as a polymerase, that will add the nucleotides to one of the primers. The two OLA primers are then covalently attached, for example using a ligase enzyme such as is known in the art, to form a modified primer. This forms a first hybridization complex comprising the ligated probe and the target sequence. This hybridization complex is then denatured (disassociated), and the process is repeated to generate a pool of ligated probes.

In a preferred embodiment, OLA is done for two strands of a double-stranded target sequence. The target sequence is denatured, and two sets of probes are added: one set as outlined above for one strand of the target, and a separate set (i.e. third and fourth primer probe nucleic acids) for the other strand of the target. In a preferred embodiment the first and third probes will hybridize, and the second and fourth probes will hybridize, such that amplification can occur. That is, when the first and second probes have been attached, the ligated probe can now be used as a template, in addition to the second target sequence, for the attachment of the third and fourth probes. Similarly, the ligated third and fourth probes will serve as a template for the attachment of the first and second probes, in addition to the first target strand. In this way, an exponential, rather than just a linear, amplification can occur.

Chemical Ligation Techniques

A variation of ligase chain reaction (LCR) utilizes a "chemical ligation" of sorts, as is generally outlined in U.S. Pat. Nos. 5,616,464 and 5,767,259, both of which are hereby incorporated by reference in their entirety. In this embodiment, similar to enzymatic ligation, a pair of primers are utilized, wherein the first primer is substantially complementary to a first domain of the target and the second primer is substantially complementary to an adjacent second domain of the target (although, as for enzymatic ligation, if a "gap" exists, a polymerase and dNTPs may be added to "fill in" the gap). Each primer has a portion that acts as a "side chain" that does not bind the target sequence and instead acts as one half of a stem structure that interacts non-covalently through hydrogen bonding, salt bridges, van der Waal's forces, etc. Preferred embodiments utilize substantially complementary nucleic acids as the side chains. Thus, upon hybridization of the primers to the target sequence, the side chains of the primers are brought into spatial proximity, and, if the side chains comprise nucleic acids as well, these can form side chain hybridization complexes.

At least one of the side chains of the primers comprises an activatable cross-linking agent, generally covalently attached to the side chain, which, upon activation, results in a chemical cross-link or chemical ligation. The activatable group may comprise any moiety that will allow cross-linking of the side chains, and include groups activated chemically, photonically and thermally, with photoactivatable groups being preferred. In some embodiments a single activatable group on one of the side chains is enough to result in cross-linking via interaction to a functional group on the other side chain; in alternate embodiments, activatable groups are required on each side chain.

Once the hybridization complex is formed, and the cross-linking agent has been activated such that the primers have been covalently attached, the reaction is subjected to conditions to allow for the disassociation of the hybridization complex, thus freeing the target to serve as a template for the next ligation or cross-linking. In this way, signal amplification occurs, and can be detected as described further herein.

Invasive Cleavage Techniques

In one embodiment, invasive cleavage technology is used to amplify polynucleotide molecules. This technology is described in a number of patents and patent applications, including U.S. Pat. Nos. 5,846,717; 5,614,402; 5,719,028; 5,541,311; and 5,843,669, all of which are hereby incorporated by reference in their entirety. Invasive cleavage technology is based on structure-specific nucleases that cleave nucleic acids in a site-specific manner. Two probes are used: an "invader" probe and a "signaling" probe. Both probes adjacently hybridize to a target sequence with overlap. For mismatch discrimination, the invader technology relies on complementarity at the overlap position where cleavage occurs. The enzyme cleaves at the overlap, and releases the "tail" which may or may not be labeled. This "tail" can then be detected. As described herein, many label probes known in the art can be used in accordance with this aspect of the invention.

Multiple Stage Amplification

In a preferred aspect of the invention, polynucleotide molecules undergo multiple stages of amplification prior to any further processing (e.g., disposition on a surface, circularization, sequencing, and the like).

As used herein, a "first stage amplification" refers to the creation of concatemers from a polynucleotide molecule, such as a fragment of source nucleic acid, a target polynucleotide, a fragment of a target polynucleotide, and the like. In a particularly preferred embodiment, a concatemer (also referred to herein as an "amplicon" or a "first stage amplicon") is created using a rolling circle replication technique.

In a particularly preferred aspect, the first stage amplification producing a concatemer is followed by a second amplification. This second stage amplification may occur in solution or in situ. By "in situ amplification" as used herein is meant amplification after disposition of a concatemer on a surface. A second stage amplification may be followed by further rounds of amplification (i.e., third stage amplification, fourth stage amplification, and so forth) to create a desired size of amplicon. For example, in one embodiment, a first stage amplification is followed by emulsion PCR (described further below) as a second stage amplification. The resultant second stage amplicon can then be disposed on a surface and then subjected to further rounds of amplification in situ.

In Situ Amplification

In a preferred embodiment of the invention, after disposition of a surface, concatemers are amplified in a second stage amplification, also referred to herein as "in situ amplification". In this embodiment, concatemers disposed on a surface are subjected to one or more rounds of amplification, resulting in multiple copies of the concatemer in a single, optically resolvable position on an array. Thus, amplification will result is an enhanced signal due to the increased number of the target polynucleotides to be analyzed, and allows for more accuracy in assays using the arrays of the invention.

Second stage amplification of target polynucleotides may be carried out using a variety of methods known in the art and described herein. The following provide some exemplary embodiments of in situ amplification, but methods of in situ amplification are in no way limited to the following embodiments.

Nicking Endonuclease

Figure 5:
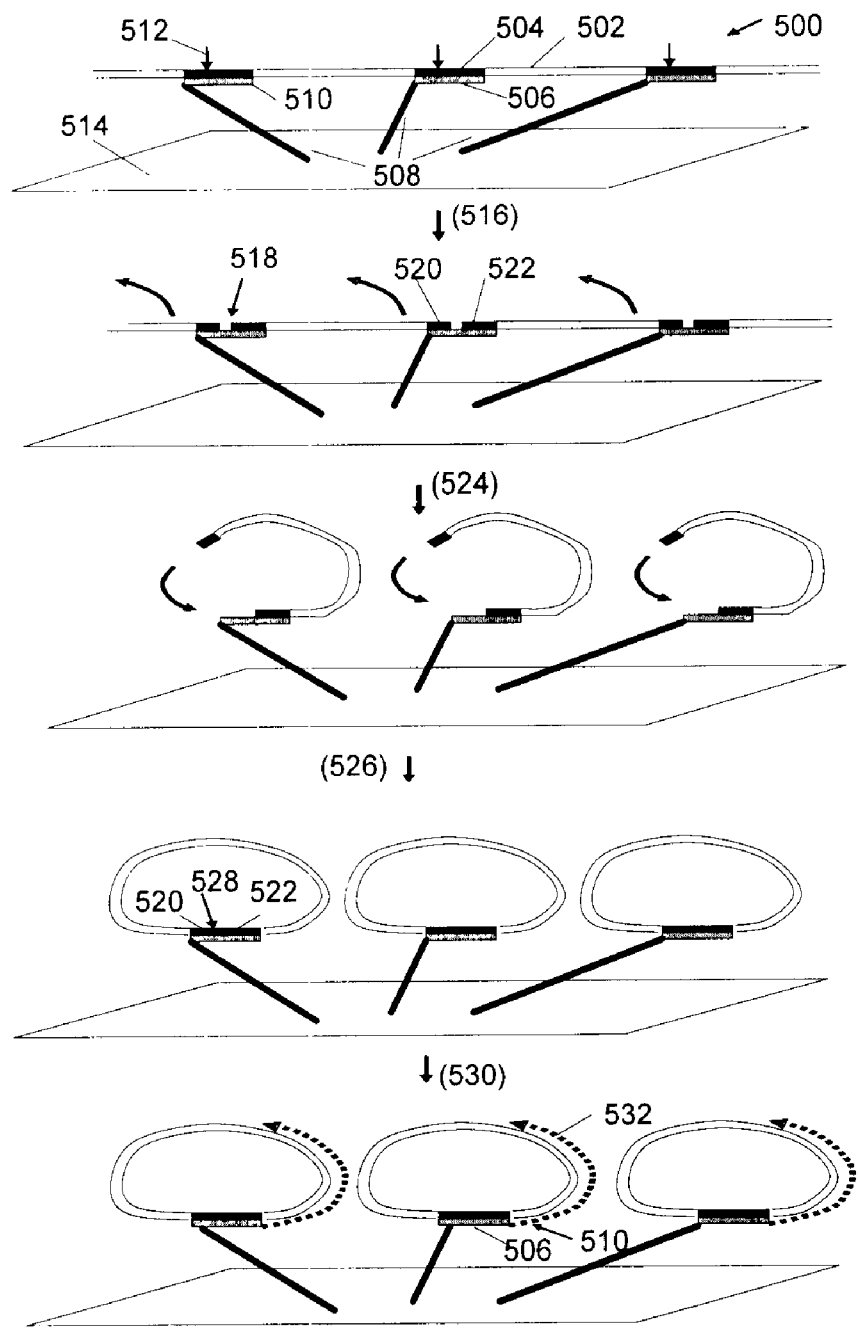
FIGS. 5-7 illustrate several embodiments of the invention for implementing second stage amplification (amplification of concatenated copies of a target polynucleotide) in situ or partially in situ. Each of these embodiments results in multiple copies of a concatemer present on an array in a single, optically resolvable position.

FIG. 5 illustrates one exemplary process for in situ amplification of a first stage amplicon (i.e., a concatemer) that has been deposited on a surface. A first stage amplicon (500) is attached to surface (514) by the formation of duplexes between adaptors (504) and capture probes (506), which are bound to surface (514) by linkages (508) that leave 3' ends (510) of capture probes (506) free, making the capture probe capable of being extended by a polymerase. In one aspect, the linkages are a separate molecule from the capture probes; in another aspect, the linkages are part of the capture probe molecule, with the condition that the 3' end of the capture probe is free to bind to/hybridize with an adaptor.

Adaptor oligonucleotides (504) and capture oligonucleotides (506) are designed to contain the recognition site of a nicking endonuclease, the site being oriented so that the nicking endonuclease cleaves the strand of a first stage amplicon (500) at an off-center location (512) along the capture oligonucleotide (506). This nicking results in a small duplex portion (520) and a large duplex portion (522), the relative size of each selected so that the large duplex portions (522) remain stable and in duplex form during subsequent steps of circle formation (described below), and the small duplex portions (520) are unstable and dissociate from the capture oligonucleotides to which they are originally bound. After nicking (516) by an appropriate nicking enzyme, nicks in the amplicon (518) are formed allowing small duplex portions (520) to dissociated and hybridize (albeit at low stability) with adjacent capture oligonucleotides so that in the presence of a ligase (526) DNA circles (519) are formed by ligation (528) of small duplex portion (520) with large duplex portion (522) of an adjacent capture oligonucleotide. Free 3' ends (510) of capture oligonucleotides (506) are then extended (530) to form second stage amplicons (532) using a strand displacement polymerase. An initial concatemer of 100-1000 units may generate about 10-500 concatemers each with about 30-300 or more units providing 3 to 150 fold or greater amplification.

In a similar aspect, following the binding of the concatemer to the capture probes on the surface, the primers can be extended without a displacement polymerase to form a set of copies that are individually attached to surface. This array may be used for target sequence analyses or other assays wherein multiple individually attached copies of the target polynucleotide are desirable. Such arrays may be used for further in situ amplification before they are used for target polynucleotide analysis or for other assays, such as protein-DNA binding. By adjusting the position of the primer binding site in the adapter, these individual copies may have a portion of the adapter copied at their free 3' end. On example of a use of these individual attached copies of the target polynucleotide would be the further amplification of such molecules in situ, e.g., by bridge PCR (Pemov et al., Nucleic Acids Research 2005 33(2):e11) or various other methods described in U.S. Ser. No. 10/547,214.

Strand Displacing Polymerase

In a preferred aspect, the invention provides a method for making a random array of concatemers in which a plurality of concatemers (also referred to herein as "first stage amplicons" or "RCR amplicons") are immobilized on a surface through duplexes formed between the concatemers and capture probes which are on the surface. The capture probes have free 3' ends and the capture probes are extended using a strand-displacing polymerase. The extension of the capture probes results in amplification of the concatemers attached to the probes through the duplexes.

Figure 6:
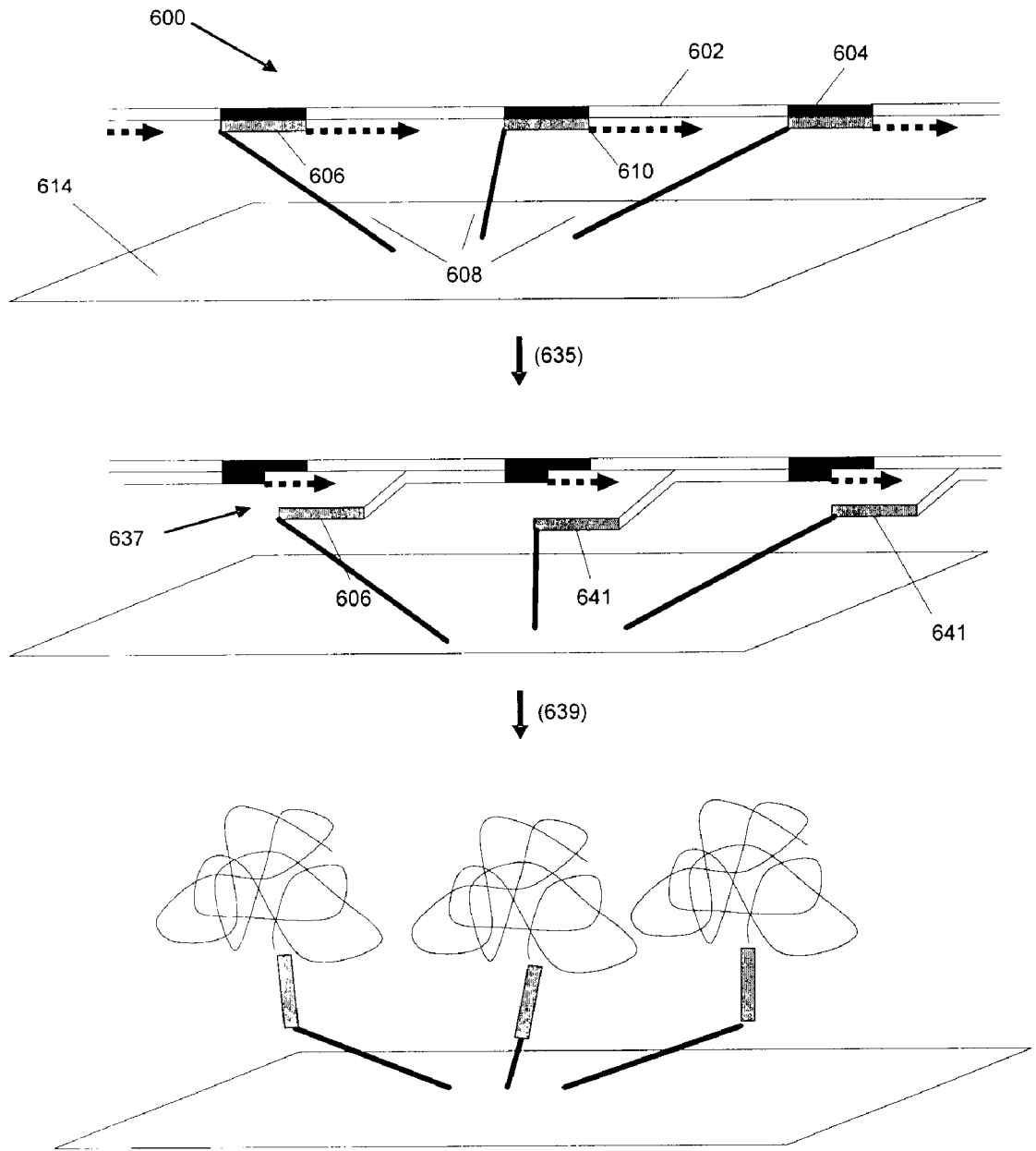

FIG. 6 illustrates an exemplary process for carrying out a second stage (in situ) amplification of an RCR amplicon (600) disposed on surface (614). As above, the amplicon (600), comprising multiple copies of a target polynucleotide (602) or its complement and an adaptor oligonucleotide (604), is captured by capture oligonucleotides (606), which themselves are anchored to surface (614) by linkages (608). Optionally, such complexes are to restricted to a specific locale on the surface (614), e.g., which can be determined by controlling the placement of the surface linkages region. Capture oligonucleotides (606) each have a free and extendable 3' end (610) that is extended (635) using a strand displacing DNA polymerase, such as Phi29. Thus, the extension product (637) of each capture oligonucleotide (606) displaces each successive capture oligonucleotide (e.g., 640 and 641) as it is synthesized on the first stage amplicon template. This results in a population of second stage amplicons having different lengths depending on the location at which their respective capture oligonucleotides annealed to the first stage amplicon. After extension of the capture oligonucleotides, surface (614) may be washed (639) under denaturing conditions to form separate single stranded second stage amplicons each comprising the same target polynucleotide in the same restricted region of surface (614).

In a specific aspect of certain embodiments, each of the concatemers are made up of multiple individual target polynucleotides, and these polynucleotides in turn include an adaptor and a target sequence. As described herein, target sequences are generally a portion of a target polynucleotide. In a particularly preferred embodiment, different concatemers contain target sequences which represent or are derived from a different portion of the target polynucleotide. In a particularly preferred embodiment, a plurality of concatemers will include enough target sequences such that together, the different target sequences cover (i.e., represent) at least a portion of the target polynucleotide from which they are derived. In one embodiment, the different target sequences cover at least a majority of the target polynucleotide. In a further embodiment, the target sequences cover at least about 95%, 90%, 80%, 70%, 60%, 50%, 40%, 30%, 20%, 10%, or 5% of the target polynucleotide.

Figure 7:
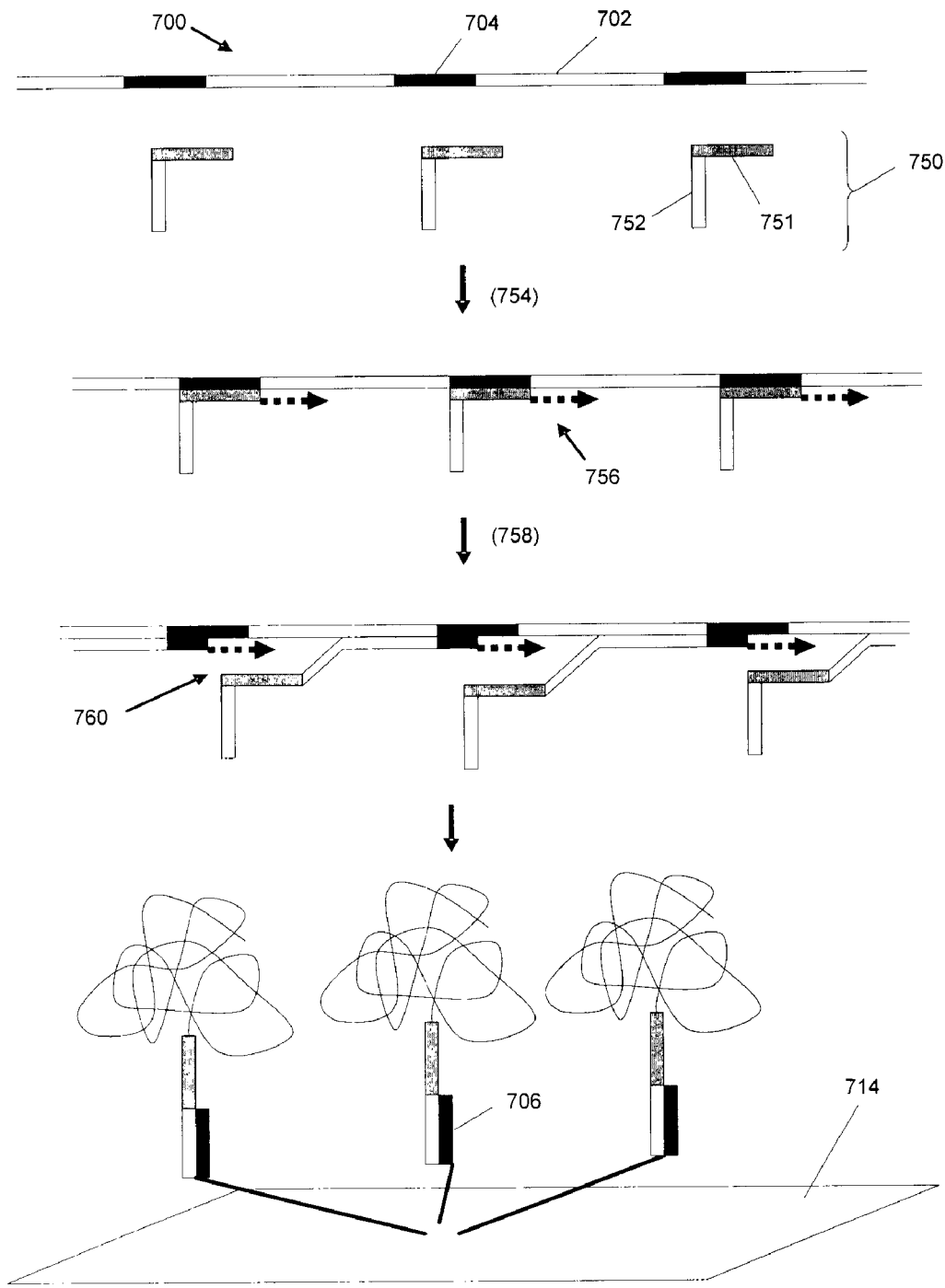

In one embodiment, the concatemers include adaptors which have recognition sites for nicking endonucleases. In a particularly preferred embodiment, the recognition is oriented in such a way that the cleavage site for the nicking endonuclease is located within the adaptor. FIG. 7 illustrates another alternative embodiment for carrying out a second stage amplification. In this case, the second stage amplification is performed completely or partially in solution, and the amplified constructs attached to the array surface following the amplification process. The amplified copies are attached to the array within a single, optically resolvable position on the array. Thus, amplification will result is an enhanced signal due to the increased number of the target polynucleotides to be analyzed.

In this case, the second stage amplification is performed completely or partially in solution. A first stage amplicon (700) comprising a concatemer of copies of a target polynucleotide (702) and adaptors (704) is combined (754) with tailed or standard primers (750) under conditions that allow a complementary portion (751) to hybridize to adaptors (704). Complementary portions are then extended (756) in a conventional polymerase extension reaction (760) using a DNA polymerase having strand displacement activity to create a complex, also referred to herein as a "concatemer-extension product complex". Extension time may be controlled to keep most of the extension product strands within the complex. A short extension in solution may be continued after forming an array of the generated complexes to create more copies of the concatemer. The resulting complex of final or partial extension products may then be disposed onto a surface (714) where it is captured by capture oligonucleotides (706) that bind to primer tails (752) or other portions of the original adaptor sequence. In an alternative embodiment, adaptor oligonucleotide sequences and tailed primer sequences may be selected so that complexes are directed to particular sites on surface (714). This embodiment allows capture oligonucleotides to be synthesized in situ using conventional chemistry that results in free 5' ends on the capture oligonucleotides. In another embodiment, the captured complex may be in situ amplified using any method known in the art and described herein, including using a strand-displacing polymerase as discussed above.

The complex may also be attached to a surface that includes reactive functionalities, and the complex binds chemically or physically to the surface through such reactive functionalities. In still another embodiment, the complex is simply disposed on a surface, such as a glass surface, and the complex is immobilized by being adsorbed on the surface through non-specific interactions between the complex and the surface.

In a preferred embodiment, the amplicons from any second stage amplification are positionally restricted to the immediate vicinity of the first stage amplicon; this positional restriction in a particularly preferred embodiment occurs when discrete regions on a surface are used.

Double Stranded First Stage Amplicons

Figure 8:
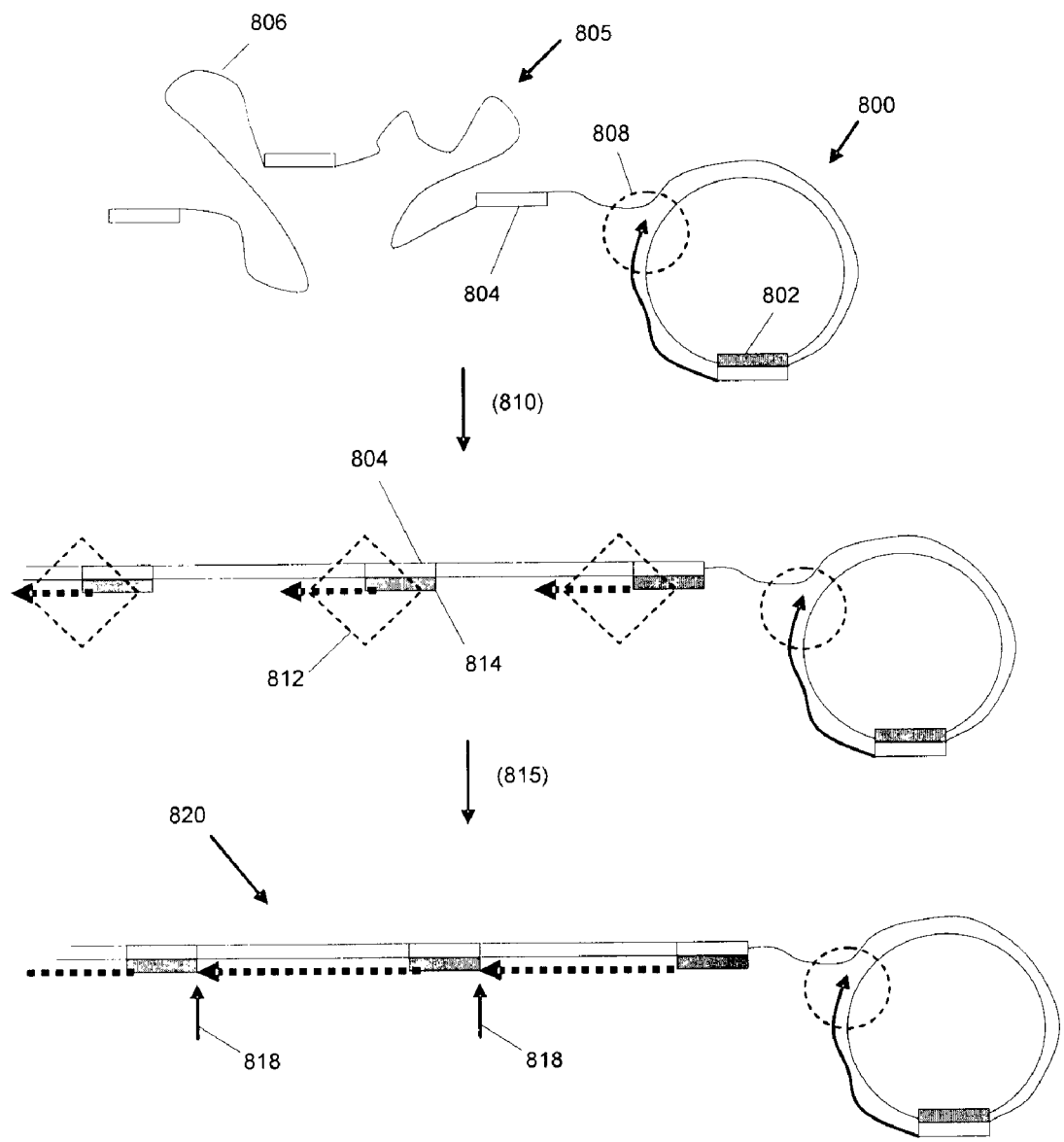
FIG. 8 illustrates a method of converting a single stranded RCR amplicon into a double stranded amplicon.

In some embodiments, it may be advantageous to generate double stranded first stage amplicons. In FIG. 8, a method is shown for converting a single stranded RCR amplicon into a double stranded amplicon. DNA circle (800) containing an adaptor complement (802) is replicated by RCR using strand-displacing polymerase (808) to produce single stranded amplicon (805) that comprises adaptor (804) and target polynucleotide (806). To this product is added (810) complements (814) of adaptor (804) and, in excess activity, polymerase (812) that lacks strand displacing activity (in other words, a non-strand displacing polymerase) and optionally a ligase. In the resulting reaction (815), complements (814) are extended to the next downstream complement leaving gaps (818), which are optionally ligated to complete the conversion to double stranded amplicon (820). Non-ligated products may be used for further extension with a strand displacement enzyme at a later step. For example, tailed or chemically modified primers such as described in FIG. 7 may be used to capture the double-stranded product on the surface followed by extension of all 3' ends from the reaction (815) to produce a secondary amplification.

Dendrimers

Figure 9:
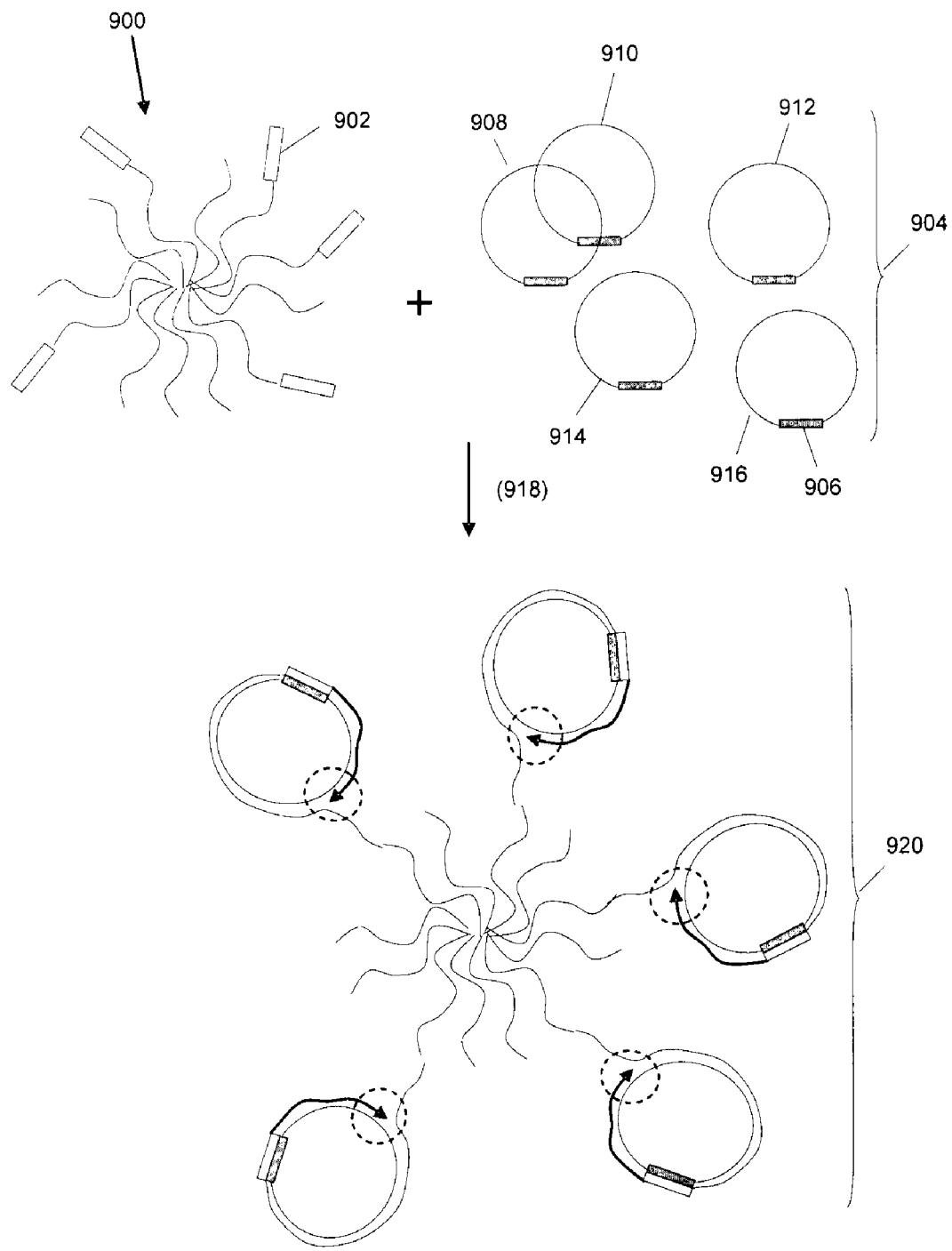
FIG. 9 illustrates preparation of an amplicon using a dendrimer and a cluster of concatemers.

Dendrimers or similar branched macromolecular structures may be employed to generate multiple-target polynucleotide comprising amplicons for attachment at a single site, to increase the compactness of a multi-sequence comprising amplicon, or to provide secondary amplification of an amplicon comprising a single sequence. As illustrated in FIG. 9, dendrimers (900) can be designed so that there are capture oligonucleotides (902) for each of a plurality of DNA circles (904) that may each contain a different adaptor oligonucleotide (906). In one aspect, such plurality is in the range of from 2 to 10, and more preferably, in the range of from 2-4. Target polynucleotides (908 through 916) may be the same or different, but usually are different from one another if multiple different target polynucleotides are amplified in the same dendrimer.

After combining dendrimer (900) with plurality (904) under suitable conditions for duplex formation between capture oligonucleotides (902) and adaptor oligonucleotides (906), capture oligonucleotides (902) are extended (918) in RCR reactions to produce multiplex amplicon (920) (also referred to herein as "dendrimer-extension product complexes"), which may be disposed on a surface for analysis.

Figure 10:
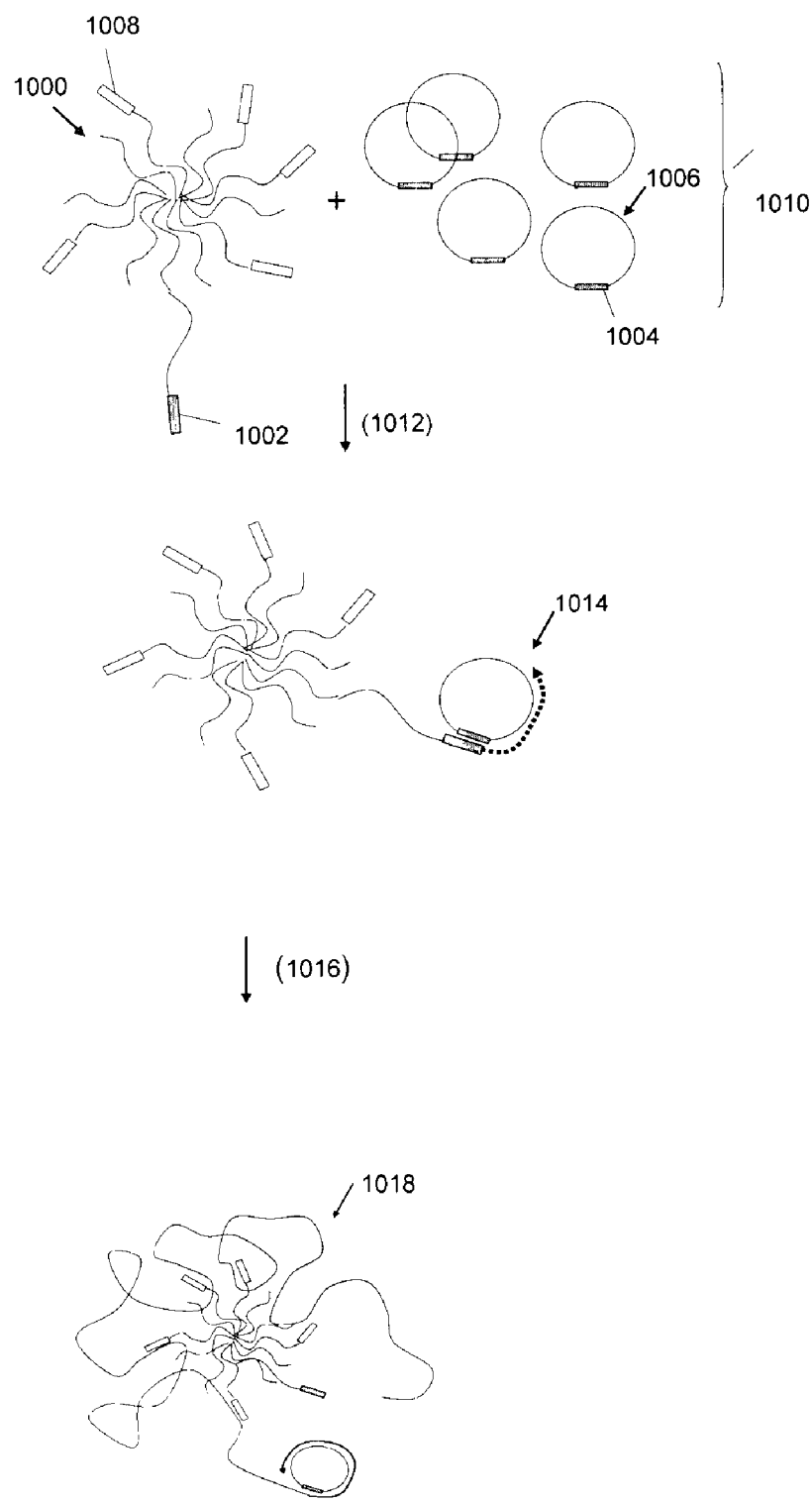
FIG. 10 illustrates preparation of an amplicon using a dendrimer having a capture probe for a single concatemer.

Dendrimers may also be used with a single kind of DNA circle to produce a first stage amplicon that is spatially more compact than an unconstrained random coil amplicon. As shown in FIG. 10, dendrimer (1000) may be designed to have a single primer oligonucleotide (1002) with a free 3' end that is capable of annealing to a complementary adaptor oligonucleotide (1004) in a DNA circle (e.g., 1006) and several capture sequences (1008) that are complementary to a sequence of a DNA circle, such as (1010). Such capture sequences (1008) may be the same or different than those of adaptor oligonucleotide (1004). When dendrimer (1000) is combined under appropriate reaction conditions with DNA circles (1010), primer oligonucleotide (1002) anneals (1012) to its complement among DNA circles (1010) and is extended by RCR (1014). As extension continues and a single stranded amplicon is formed, complementary sequences to capture sequence (1008) form duplexes (not shown, 1016) and constrain the amplicon to the vicinity of dendrimer (1000) producing complex (1018). The spatial compaction using dendrimers may also be performed after the concatemers are created. In this embodiment, the dendrimers may not have adaptors but will still comprise capture sequences. When the dendrimers are combined with the pre-formed concatemers, the concatemers will bind to the capture sequences and as a result, take on a more spatially compact form.

The above described approach can in turn also be used for secondary amplification by extending 3' end of adaptor complements by a strand displacement polymerases to create a cluster of concatemers with different sizes all containing the same nucleic acid unit. Producing a cluster of different concatemers in a single amplicon molecule (FIG. 9) can be combined with above described "compacting" approach or this approach of secondary amplification, e.g., the process can start with a dendrimer that has single primer for each of 2-10 different circles with their specific complementary adaptors and additional primers for secondary amplification of all first amplicons as illustrated in FIG. 10.

Emulsion PCR

Figure 11:
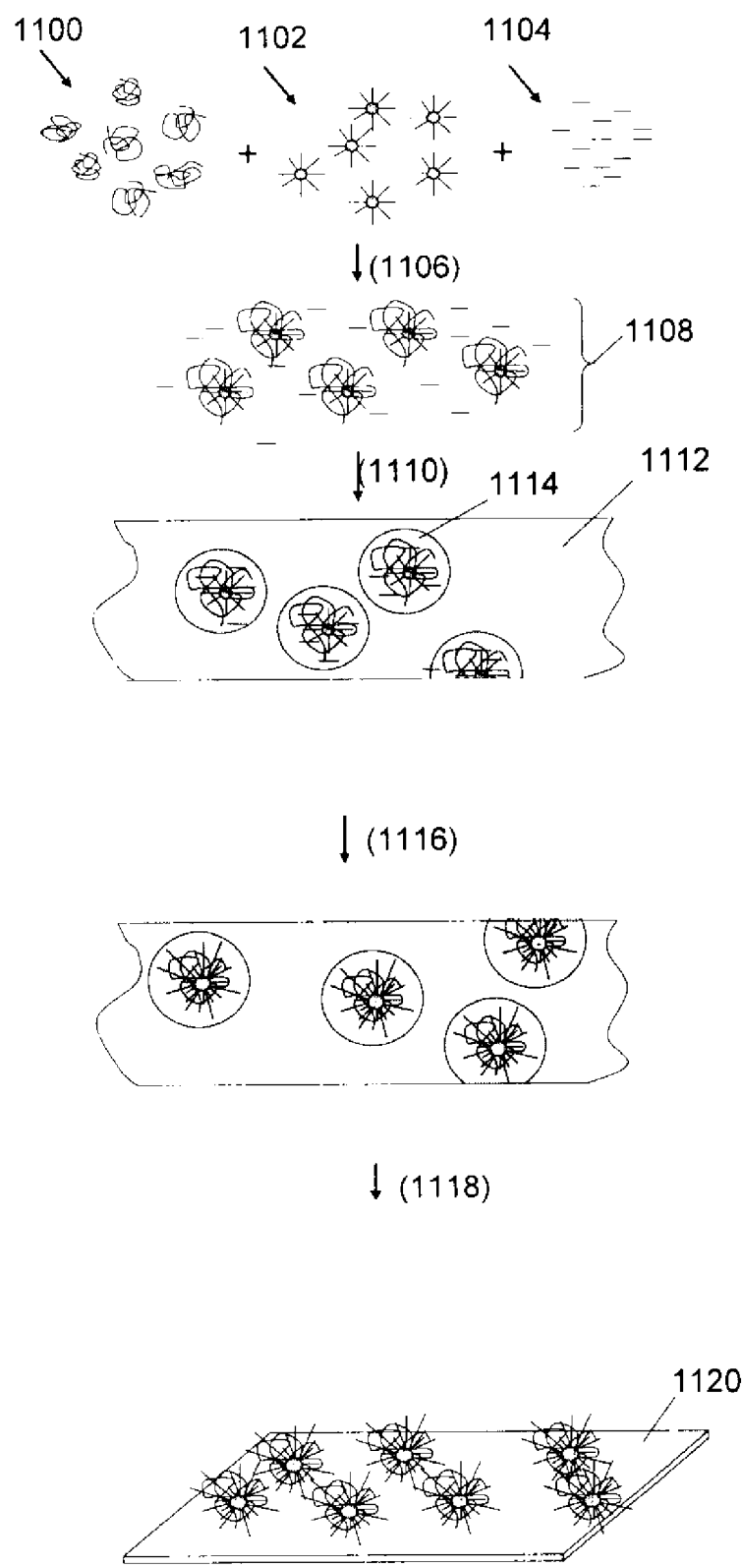
FIG. 11 illustrates an aspect of the invention for second stage amplification of target polynucleotides using emulsion polymerase chain reaction (PCR) on beads.

In one embodiment, emulsion PCR, as illustrated in FIG. 11, is used to amplify concatemers prior to disposition of the concatemers on a surface. In one embodiment, single stranded amplicons (1100), e.g., RCR products, are combined (1106) with first primer oligonucleotides (1104) and beads (1102) derivatized with both second primer oligonucleotides and optionally capture probes. In resulting reaction mixture (1108), beads and amplicons (100) aggregate, so that upon emulsification (1110) aqueous cells (1114) in oil (1112) contain mostly a single bead aggregated with a single amplicon. (The physical constraint or limited number of capture probes never or rarely allows two RCR products to bind to the same bead).

Use of water-in-oil emulsions to carry out enzymatic reactions is well known in the art, particularly carrying out PCRs, e.g., as disclosed by Margulies et al, Nature, 437: 376-380 (2005); Shendure et al (2005), Science, 309: 1728-1732; Berka et al, U.S. patent publication 2005/0079510; Church et al, PCT publication WO 2005/082098; Nobile et al, U.S. patent publication 2005/0227264; Griffiths et al, U.S. Pat. No. 6,489,103; Tillett et al, PCT publication WO 03/106678; Kojima et al, Nucleic Acids Research, 33 (17): e150 (2005); Dressman et al, Proc. Natl. Acad. Sci., 100: 8817-8822 (2003); Mitra et al, Anal. Biochem., 320: 55-65 (2003); Musyanovych et al, Biomacromolecules, 6: 1824-1828 (2005); Li et al, Nature Methods, 3: 95-97 (2006); and the like, which are incorporated herein by reference.

PCR is conducted (1116) with segments of the amplicon being amplified by the first and second primer oligonucleotides. Initiating emulsion PCR with about 30-300 copies of target DNA instead of one in standard emulsion PCR provides much higher success rate and reduces impact of PCR error rates. After the emulsion is broken, beads (1102) having a second stage amplicon attached may be disposed (1118) on a surface (1120) for analysis. A preferred substrate for arraying beads has a grid of active sites or small wells that allow attachment only of one bead per site or well and that may be driven to very high occupancy of available sites or wells. In one aspect beads may be attached to a surface by use of conventional binding pairs, such as streptavidin-biotin, or the like.

Disposition of Concatemers and Circularized DNA Molecules on a Surface

In a preferred aspect, polynucleotide molecules, including concatemers and circularized DNA molecules, are disposed on a surface to form a random array of single molecules. Polynucleotide molecules can be fixed to surface by a variety of techniques, including covalent attachment and non-covalent attachment. In one embodiment, a surface may include capture probes that form complexes, e.g., double stranded duplexes, with component of a polynucleotide molecule, such as an adaptor oligonucleotide. In other embodiments, capture probes may comprise oligonucleotide clamps, or like structures, that form triplexes with adaptors, as described in Gryaznov et al, U.S. Pat. No. 5,473,060, which is hereby incorporated in its entirety.

In another embodiment, a surface may have reactive functionalities that react with complementary functionalities on the polynucleotide molecules to form a covalent linkage, e.g., by way of the same techniques used to attach cDNAs to microarrays, e.g., Smirnov et al (2004), Genes, Chromosomes & Cancer, 40: 72-77; Beaucage (2001), Current Medicinal Chemistry, 8: 1213-1244, which are incorporated herein by reference. Long DNA molecules, e.g., several hundred nucleotides or larger, may also be efficiently attached to hydrophobic surfaces, such as a clean glass surface that has a low concentration of various reactive functionalities, such as —OH groups. Attachment through covalent bonds formed between the polynucleotide molecules and reactive functionalities on the surface is also referred to herein as "chemical attachment".

In still another embodiment, polynucleotide molecules can adsorb to a surface. In such an embodiment, the polynucleotide molecules are immobilized through non-specific interactions with the surface, or through non-covalent interactions such as hydrogen bonding, van der Waals forces, and the like.

Attachment may also include wash steps of varying stringencies to remove incompletely attached single molecules or other reagents present from earlier preparation steps whose presence is undesirable or that are nonspecifically bound to surface.

Upon attachment to a surface, single stranded polynucleotides generally fill a flattened spheroidal volume that on average is bounded by a region which is approximately equivalent to the diameter of a concatemer in random coil configuration. How compact a single stranded polynucleotide is once disposed on a surface can be affected by a number of factors, including the attachment chemistry used, the density of linkages between the polynucleotide and the surface, the nature of the surface, and the like. Preserving the compact form of the macromolecular structure of polynucleotides (including concatemers, target polynucleotides, and target sequences) on a surface can increase the signal to noise ratio, for example, a compact concatemer can result in a more intense signal from probes, (e.g., fluorescently labeled oligonucleotides) that are specifically directed to components of the concatemer.

One measure of the size of a random coil polymer, such as single stranded DNA, is a root mean square of the end-to-end distance, which is roughly a measure of the diameter of the randomly coiled structure. Such diameter, referred to herein as a "random coil diameter," can be measured by light scatter, using instruments, such as a Zetasizer Nano System (Malvern Instruments, UK), or like instrument. Additional size measures of macromolecular structures of the invention include molecular weight, e.g., in Daltons, and total polymer length, which in the case of a branched polymer is the sum of the lengths of all its branches.

Figure 12:
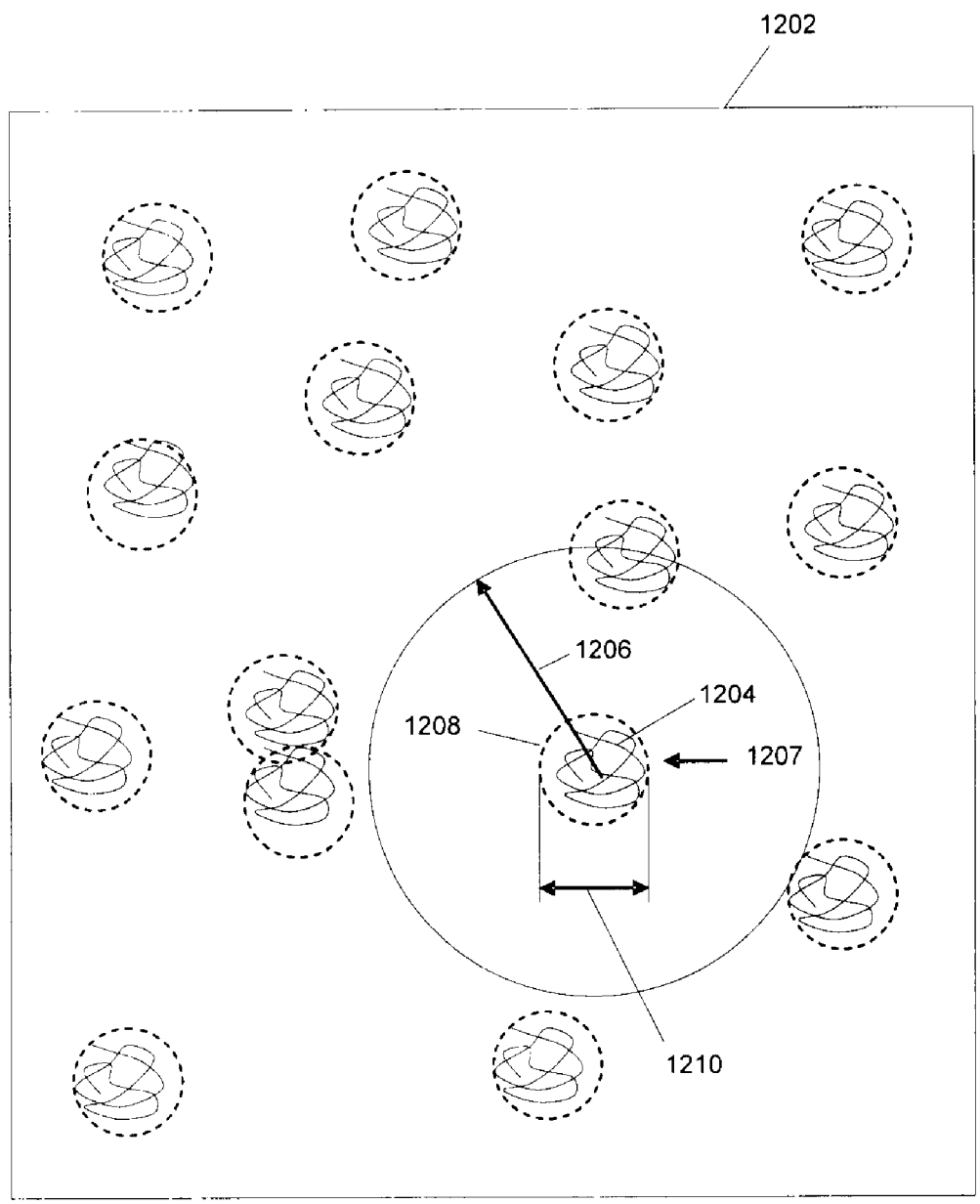
FIG. 12 illustrates a top view of placement of concatemers onto discrete regions on an array surface.

In one aspect, as illustrated in FIG. 12, macromolecular structures, e.g., concatemers, and the like, are attached to a surface (1202) within a region that is substantially equivalent to a projection of its random coil state onto surface (1202), for example, as illustrated by dashed circles (1208). An area occupied by a macromolecular structure can vary, so that in some embodiments, an expected area may be within the range of from 2-3 times the area of projection (1208) to some fraction of such area, e.g., 25-50 percent. As discussed herein, preserving the compact form of the macromolecular structure on the surface allows a more intense signal to be produced by probes, such as fluorescently labeled oligonucleotides, which are specifically directed to components of a macromolecular structure or concatemer. The size of diameter (1210) of regions (1207) and distance (1206) to the nearest neighbor region containing a single molecule are two quantities of interest in the fabrication of arrays.

A variety of distance metrics may be employed for measuring the closeness of single molecules on a surface, including center-to-center distance of regions, edge-to-edge distance of regions, and the like. Usually, center-to-center distances are employed herein. The selection of these parameters in fabricating arrays of the invention depends in part on the signal generation and detection systems used in the analytical processes. Generally, densities of single molecules are selected that permit at least thirty percent, or at least fifty percent, or at least a majority of the molecules to be resolved individually by the signal generation and detection systems used. In one aspect, a density is selected that permits at least seventy percent of the single molecules to be individually resolved. In one embodiment, scanning electron microscopy is employed, for example, with molecule-specific probes having gold nanoparticle labels, e.g., Nie et al (2006), Anal. Chem., 78: 1528-1534, which is incorporated by reference. In such an embodiment, a density is selected such that at least a majority of single molecules have a nearest neighbor distance of 50 nm or greater; and in another aspect, such density is selected to ensure that at least seventy percent of single molecules have a nearest neighbor distance of 100 nm or greater. In another embodiment, optical microscopy is employed, for example with molecule-specific probes having fluorescent labels, a density is selected such that at least a majority of single molecules have a nearest neighbor distance of 200 nm or greater. In still another embodiment, a density is selected to ensure that at least seventy percent of single molecules have a nearest neighbor distance of 200 nm or greater. In still another embodiment, optical microscopy is employed, for example with molecule-specific probes having fluorescent labels, and in this embodiment a density is selected such that at least a majority of single molecules have a nearest neighbor distance of 300 nm or greater; in a further embodiment, such density is selected to ensure that at least seventy percent of single molecules have a nearest neighbor distance of 300 nm or greater, or 400 nm or greater, or 500 nm or greater, or 600 nm or greater, or 700 nm or greater, or 800 nm or greater. In still another embodiment in which optical microscopy is used, a density is selected such that at least a majority of single molecules have a nearest neighbor distance of at least twice the minimal feature resolution power of the microscope. In another aspect, polymer molecules (including polynucleotides, concatemers, target polynucleotides, and other polynucleotide molecules discussed herein) of the invention are disposed on a surface so that the density of separately detectable polymer molecules is at least 1000 per $\mu m^2$, or at least 10,000 per $\mu m^2$, or at least 100,000 per $\mu m^2$.

In one aspect, polynucleotide molecules on a surface are confined to an area of a discrete region. Discrete regions may be incorporated into a surface using methods known in the art and described further herein. In a preferred embodiment, discrete regions contain reactive functionalities or capture probes which can be used to immobilize the polynucleotide molecules.

The discrete regions may have defined locations in a regular array, which may correspond to a rectilinear pattern, hexagonal pattern, or the like. A regular array of such regions is advantageous for detection and data analysis of signals collected from the arrays during an analysis. Also, first- and/or second-stage amplicons confined to the restricted area of a discrete region provide a more concentrated or intense signal, particularly when fluorescent probes are used in analytical operations, thereby providing higher signal-to-noise values. Amplicons of target polynucleotides are randomly distributed on the discrete regions so that a given region is equally likely to receive any of the different single molecules. In other words, the resulting arrays are not spatially addressable immediately upon fabrication, but may be made so by carrying out an identification, sequencing and/or decoding operation. As such, the identities of the polynucleotide molecules of the invention disposed on a surface are discernable, but not initially known upon their disposition on the surface.

Figure 13:
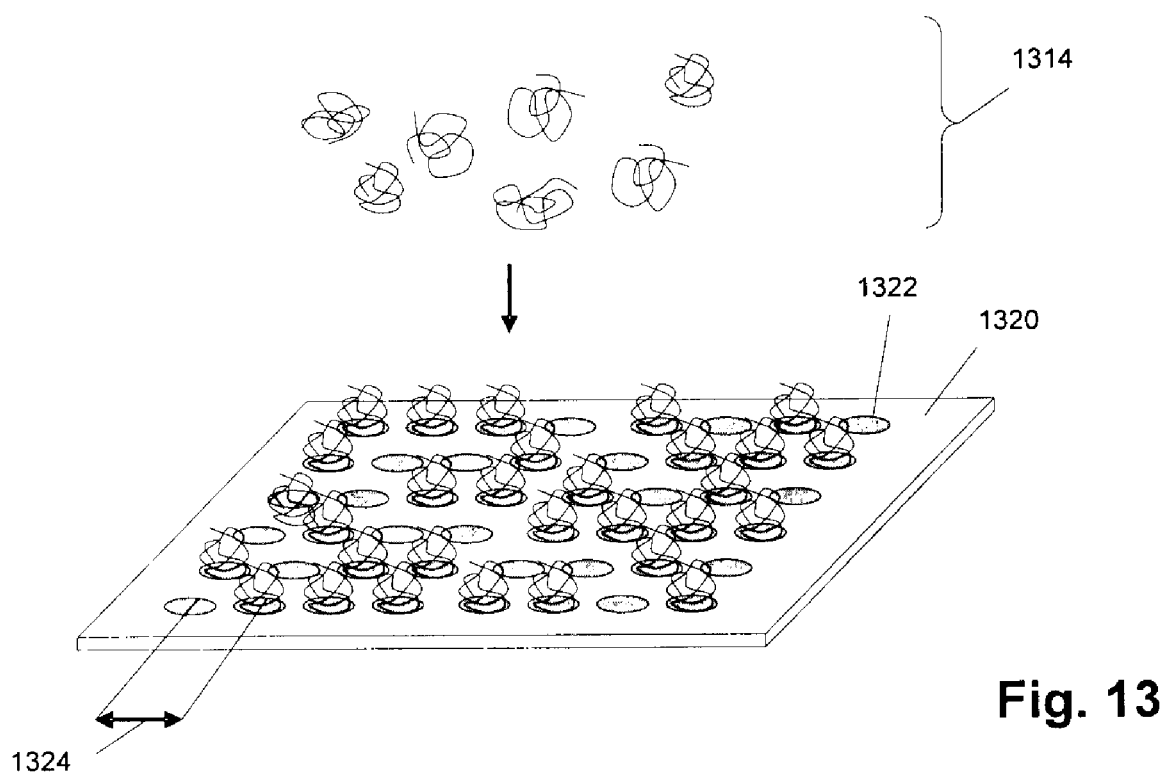
FIG. 13 illustrates the placement of concatemers in arrays with distinct regions for attachment.

One embodiment in which discrete regions are used in the disposition of polynucleotide molecules on a surface is illustrated in FIG. 13. In this embodiment, the requirement of selecting densities of randomly disposed single molecules to ensure desired nearest neighbor distances is obviated by providing discrete regions on a surface, and these discrete regions are substantially the only sites for attaching single molecules to a surface. In a preferred embodiment, molecules are directed to the discrete regions, because the areas between the discrete regions, referred to herein as "inter-regional areas," are inert, in the sense that concatemers, or other macromolecular structures, do not bind to such regions. In some embodiments, such inter-regional areas may be treated with blocking agents, e.g., DNAs unrelated to concatemer DNA, other polymers, and the like.

One embodiment of the invention in which discrete regions are utilized is illustrated in FIG. 13. Isolated concatemers or amplicons (1314) are then applied to surface (1320) that has a regular array of discrete regions (1322) that each have a nearest neighbor distance (1324) that is determined by the design and fabrication of surface (1320). Arrays of discrete regions (1322) having micron and submicron dimensions for derivatizing with capture oligonucleotides or reactive functionalities can be fabricated using conventional semiconductor fabrication techniques, including electron beam lithography, nano imprint technology, photolithography, and the like. Generally, the area of discrete regions (1322) is selected, along with attachment chemistries, macromolecular structures employed, and the like, to correspond to the size of single molecules of the invention so that when single molecules are applied to surface (1320) substantially every region (1322) is occupied by no more than one single molecule.

The likelihood of having only one single molecule per discrete region may be increased by selecting a density of reactive functionalities or capture oligonucleotides that results in fewer such moieties than their respective complements on single molecules. Thus, a single molecule will "occupy" all linkages to the surface at a particular discrete region, thereby reducing the chance that a second single molecule will also bind to the same region. In particular, in one embodiment, substantially all the capture oligonucleotides in a discrete region hybridize to adaptor oligonucleotides in a single macromolecular structure. In a further embodiment, a discrete region contains a number of reactive functionalities or capture oligonucleotides that is from about ten percent to about fifty percent of the number of complementary functionalities or adaptor oligonucleotides of a single molecule.

The length and sequence(s) of capture oligonucleotides may vary widely, and may be selected in accordance with well known principles, e.g., Wetmur, Critical Reviews in Biochemistry and Molecular Biology, 26: 227-259 (1991); Britten and Davidson, chapter 1 in Hames et al, editors, Nucleic Acid Hybridization: A Practical Approach (IRL Press, Oxford, 1985). In one embodiment, the lengths of capture oligonucleotides are in a range of from about 6 to about 50 nucleotides, in a further embodiment, the lengths of capture oligonucleotides are in a range of from about 8 to about 30 nucleotides; in a still further embodiment, the lengths are from about 10 to about 24 nucleotides. Lengths and sequences of capture oligonucleotides are selected (i) to provide effective binding of macromolecular structures to a surface, so that losses of macromolecular structures are minimized during steps of analytical operations, such as washing, etc., and (ii) to avoid interference with analytical operations on analyte molecules, particularly when analyte molecules are DNA fragments in a concatemer.

In regard to providing effective binding of macromolecular structures to a surface, in accordance with one aspect of the invention, sequences and lengths are selected to provide duplexes between capture oligonucleotides and their complements that are sufficiently stable so that they do not dissociate in a stringent wash.

In regard to avoiding interference with analytical molecules, if DNA fragments are from a particular species of organism, then databases, when available, may be used to screen potential capture sequences that may form spurious or undesired hybrids with DNA fragments.

Other factors in selecting sequences for capture oligonucleotides are similar to those considered in selecting primers, hybridization probes, oligonucleotide tags, and the like, for which there is ample guidance in the art.

In some embodiments, a discrete region may contain more than one kind of capture oligonucleotide, and each different capture oligonucleotide may have a different length and sequence.

In one aspect of the invention, regular arrays of discrete regions are employed, and sequences of capture oligonucleotides are selected so that the sequences of capture oligonucleotide at nearest neighbor regions have different sequences. In a rectilinear array, such configurations are achieved by establishing rows of alternating sequence types. In one embodiment, a surface may have a plurality of subarrays of discrete regions wherein each different subarray has capture oligonucleotides with distinct nucleotide sequences different from those of the other subarrays. A plurality of subarrays may include 2 subarrays, or 4 or fewer subarrays, or 8 or fewer subarrays, or 16 or fewer subarrays, or 32 or fewer subarrays, or 64 of fewer subarrays. In still another embodiment, a surface may include 5000 or fewer subarrays.

In one aspect, capture probes are attached to the surface of an array by a spacer molecule, e.g., polyethylene glycol, or like inert chain, as is done with microarrays, in order to minimize undesired affects of surface groups or interactions with the capture oligonucleotides or other reagents.

In another aspect, if enzymatic processing is not required, capture oligonucleotides may comprise non-natural nucleosidic units and/or linkages that confer favorable properties, such as increased duplex stability; such compounds include, but not limited to, peptide nucleic acids (PNAs), locked nucleic acids (LNA), oligonucleotide N3'→P5' phosphoramidates, oligo-2'-O-alkylribonucleotides, and the like.

In one aspect, the area of discrete regions (1122) is less than 1 $\mu m^2$; and in another aspect, the area of discrete regions (1122) is in the range of from 0.04 $\mu m^2$ to 1 $\mu m^2$; and in still another aspect, the area of discrete regions (1122) is in the range of from 0.2 $\mu m^2$ to 1 $\mu m^2$. In another aspect, when discrete regions are approximately circular or square in shape so that their sizes can be indicated by a single linear dimension, the size of such regions are in the range of from 125 nm to 250 nm, or in the range of from 200 nm to 500 nm. In one aspect, center-to-center distances of nearest neighbors of regions (1122) are in the range of from 0.25 µm to 20 µm; and in another aspect, such distances are in the range of from 1 µm to 10 µm, or in the range from 50 to 1000 nm. Generally, discrete regions are designed such that a majority of the discrete regions on a surface are optically resolvable. In one aspect, regions (1120) may be arranged on surface (1018) in virtually any pattern in which regions (1122) have defined locations, i.e. in any regular array, which makes signal collection and data analysis functions more efficient. Such patterns include, but are not limited to, concentric circles of regions (1122), spiral patterns, rectilinear patterns, hexagonal patterns, and the like. Preferably, regions (1122) are arranged in a rectilinear or hexagonal pattern.

Supports and Surfaces of the Invention

A wide variety of supports may be used with the compositions and methods of the invention to form random arrays. In one aspect, supports are rigid solids that have a surface, preferably a substantially planar surface so that single molecules to be interrogated are in the same plane. The latter feature permits efficient signal collection by detection optics, for example. In another aspect the support comprises beads, wherein the surface of the beads comprise reactive functionalities or capture probes that can be used to immobilize polynucleotide molecules.

In still another aspect, solid supports of the invention are nonporous, particularly when random arrays of single molecules are analyzed by hybridization reactions requiring small volumes. Suitable solid support materials include materials such as glass, polyacrylamide-coated glass, ceramics, silica, silicon, quartz, various plastics, and the like. In one aspect, the area of a planar surface may be in the range of from 0.5 to 4 $cm^2$. In one aspect, the solid support is glass or quartz, such as a microscope slide, having a surface that is uniformly silanized. This may be accomplished using conventional protocols, e.g., acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface. e.g., Beattie eta (1995), Molecular Biotechnology, 4: 213. Such a surface is readily treated to permit end-attachment of capture oligonucleotides, e.g., by providing capture oligonucleotides with a 3' or 5' triethylene glycol phosphoryl spacer (see Beattie et al, cited above) prior to application to the surface. Further embodiments for functionalizing and further preparing surfaces for use in the present invention are described in U.S. patent application Ser. No. 11/451,691.

In embodiments of the invention in which patterns of discrete regions are required, photolithography, electron beam lithography, nano imprint lithography, and nano printing may be used to generate such patterns on a wide variety of surfaces, e.g., Pirrung et al, U.S. Pat. No. 5,143,854; Fodor et al, U.S. Pat. No. 5,774,305; Guo, (2004) Journal of Physics D: Applied Physics, 37: R123-141; which are incorporated herein by reference.

In one aspect, surfaces containing a plurality of discrete regions are fabricated by photolithography. A commercially available, optically flat, quartz substrate is spin coated with a 100-500 nm thick layer of photo-resist. The photo-resist is then baked on to the quartz substrate. An image of a reticle with a pattern of regions to be activated is projected onto the surface of the photo-resist, using a stepper. After exposure, the photo-resist is developed, removing the areas of the projected pattern which were exposed to the UV source. This is accomplished by plasma etching, a dry developing technique capable of producing very fine detail. The substrate is then baked to strengthen the remaining photo-resist. After baking, the quartz wafer is ready for functionalization. The wafer is then subjected to vapor-deposition of 3-aminopropyldimethylethoxysilane. The density of the amino functionalized monomer can be tightly controlled by varying the concentration of the monomer and the time of exposure of the substrate. Only areas of quartz exposed by the plasma etching process may react with and capture the monomer. The substrate is then baked again to cure the monolayer of amino-functionalized monomer to the exposed quartz. After baking, the remaining photo-resist may be removed using acetone. Because of the difference in attachment chemistry between the resist and silane, aminosilane-functionalized areas on the substrate may remain intact through the acetone rinse. These areas can be further functionalized by reacting them with p-phenylenediisothiocyanate in a solution of pyridine and N-N-dimethylformamide. The substrate is then capable of reacting with amine-modified oligonucleotides. Alternatively, oligonucleotides can be prepared with a 5'-carboxy-modifier-c10 linker (Glen Research). This technique allows the oligonucleotide to be attached directly to the amine modified support, thereby avoiding additional functionalization steps.

In another aspect, surfaces containing a plurality of discrete regions are fabricated by nano-imprint lithography (NIL). For DNA array production, a quartz substrate is spin coated with a layer of resist, commonly called the transfer layer. A second type of resist is then applied over the transfer layer, commonly called the imprint layer. The master imprint tool then makes an impression on the imprint layer. The overall thickness of the imprint layer is then reduced by plasma etching until the low areas of the imprint reach the transfer layer. Because the transfer layer is harder to remove than the imprint layer, it remains largely untouched. The imprint and transfer layers are then hardened by heating. The substrate is then put into a plasma etcher until the low areas of the imprint reach the quartz. The substrate is then derivatized by vapor deposition as described above.

In another aspect, surfaces containing a plurality of discrete regions are fabricated by nano printing. This process uses photo, imprint, or e-beam lithography to create a master mold, which is a negative image of the features required on the print head. Print heads are usually made of a soft, flexible polymer such as polydimethylsiloxane (PDMS). This material, or layers of materials having different properties, are spin coated onto a quartz substrate. The mold is then used to emboss the features onto the top layer of resist material under controlled temperature and pressure conditions. The print head is then subjected to a plasma based etching process to improve the aspect ratio of the print head, and eliminate distortion of the print head due to relaxation over time of the embossed material. Random array substrates are manufactured using nano-printing by depositing a pattern of amine modified oligonucleotides onto a homogenously derivatized surface. These oligonucleotides would serve as capture probes for the RCR products. One potential advantage to nano-printing is the ability to print interleaved patterns of different capture probes onto the random array support. This would be accomplished by successive printing with multiple print heads, each head having a differing pattern, and all patterns fitting together to form the final structured support pattern. Such methods allow for some positional encoding of DNA elements within the random array. For example, control concatemers containing a specific sequence can be bound at regular intervals throughout a random array.

In still another aspect, a high density array of capture oligonucleotide spots of sub micron size is prepared using a printing head or imprint-master prepared from a bundle, or bundle of bundles, of about 10,000 to 100 million optical fibers with a core and cladding material. By pulling and fusing fibers a unique material is produced that has about 50-1000 nm cores separated by a similar or 2-5 fold smaller or larger size cladding material. By differential etching (dissolving) of cladding material a nano-printing head is obtained having a very large number of nano-sized posts. This printing head may be used for depositing oligonucleotides or other biological (proteins, oligopeptides, DNA, aptamers) or chemical compounds such as silane with various active groups. In one embodiment the glass fiber tool is used as a patterned support to deposit oligonucleotides or other biological or chemical compounds. In this case only posts created by etching may be contacted with material to be deposited. Also, a flat cut of the fused fiber bundle may be used to guide light through cores and allow light-induced chemistry to occur only at the tip surface of the cores, thus eliminating the need for etching. In both cases, the same support may then be used as a light guiding/collection device for imaging fluorescence labels used to tag oligonucleotides or other reactants. This device provides a large field of view with a large numerical aperture (potentially >1). Stamping or printing tools that perform active material or oligonucleotide deposition may be used to print 2 to 100 different oligonucleotides in an interleaved pattern. This process requires precise positioning of the print head to about 50-500 nm. This type of oligonucleotide array may be used for attaching 2 to 100 different DNA populations such as different source DNA. They also may be used for parallel reading from sub-light resolution spots by using DNA specific anchors or tags. Information can be accessed by DNA specific tags, e.g., 16 specific anchors for 16 DNAs and read 2 bases by a combination of 5-6 colors and using 16 ligation cycles or one ligation cycle and 16 decoding cycles. This way of making arrays is efficient if limited information (e.g., a small number of cycles) is required per fragment, thus providing more information per cycle or more cycles per surface.

In one embodiment "inert" concatemers are used to prepare a surface for attachment of test concatemers. The surface is first covered by capture oligonucleotides complementary to the binding site present on two types of synthetic concatemers; one is a capture concatemer, the other is a spacer concatemer. The spacer concatemers do not have DNA segments complementary to the adapter used in preparation of test concatemers and they are used in about 5-50, preferably 10× excess to capture concatemers. The surface with capture oligonucleotide is "saturated" with a mix of synthetic concatemers (prepared by chain ligation or by RCR) in which the spacer concatemers are used in about 10-fold (or 5 to 50-fold) excess to capture concatemers. Because of the ~10:1 ratio between spacer and capture concatemers, the capture concatemers are mostly individual islands in a sea of spacer concatemers. The 10:1 ratio provides that two capture concatemers are on average separated by two spacer concatemers. If concatemers are about 200 nm in diameter, then two capture concatemers are at about 600 nm center-to-center spacing. This surface is then used to attach test concatemers or other molecular structures that have a binding site complementary to a region of the capture concatemers but not present on the spacer concatemers. Capture concatemers may be prepared to have less copies than the number of binding sites in test concatemers to assure single test concatemer attachment per capture concatemer spot. Because the test DNA can bind only to capture concatemers, an array of test concatemers may be prepared that have high site occupancy without congregation. Due to random attachment, some areas on the surface may not have any concatemers attached, but these areas with free capture oligonucleotide may not be able to bind test concatemers since they are designed not to have binding sites for the capture oligonucleotide. An array of individual test concatemers as described would not be arranged in a grid pattern. An ordered grid pattern should simplify data collection because less pixels are needed and less sophisticated image analysis systems are needed also.

In one aspect, multiple arrays of the invention may be placed on a single surface. For example, patterned array substrates may be produced to match the standard 96 or 384 well plate format. A production format can be an 8×12 pattern of 6 mm×6 mm arrays at 9 mm pitch or 16×24 of 3.33 mm×3.33 mm array at 4.5 mm pitch, on a single piece of glass or plastic and other optically compatible material. In one example each 6 mm×6 mm array consists of 36 million 250-500 nm square regions at 1 micrometer pitch. Hydrophobic or other surface or physical barriers may be used to prevent mixing different reactions between unit arrays.

In a preferred aspect, sites on a surface in which polynucleotide molecules of the invention are disposed are surrounded by inter-regional areas which are inert. In such an aspect, non-specific binding in the inter-regional areas is minimized by controlling the physical and chemical features of these inter-regional areas. Methods for establishing such inert inter-regional areas are well known in the art. For example, the inter-regional areas may be prepared with hexamethyldisilazane (HMDS), or a similar agent covalently bonded to the surface, to be hydrophobic and hence unsuitable to hydrophilic bonding of the DNA samples. Similarly, the inter-regional areas may be coated with a chemical agent such as a fluorine-based carbon compound that renders the areas unreactive to DNA samples.

In another aspect of the invention, random arrays are prepared using nanometer-sized beads. Sub-micron glass or other types of beads (e.g., in the 20-50 nm range) are used which are derivatized with a short oligonucleotide, e.g., 6-30 nucleotides, complementary to an adaptor oligonucleotide in the circles used to generate concatemers. The number of oligonucleotides on the bead and the length of the sequence can be controlled to weakly bind the concatemers in solution. In one embodiment, the density of capture probes can be controlled through the use of shorter oligonucleotides that have the same attachment chemistry with the capture probe. Also, much smaller nano-beads (20-50 nm) can be used in accordance with this aspect of the invention. After binding concatemers, the beads can be allowed to settle on the surface of an array substrate. Array conditions may be selected to permit preferential binding to the surface, thereby forming a spaced array of concatemers. If the beads are magnetic, a magnetic field can be used to pull the beads to the surface and may also be used to move them around the surface. Alternatively, a centrifuge may be used to concentrate the beads on the surface. In still another embodiment, horizontal or tilting movements of the surface can be used to move beads from the inter-regional areas to settle in discrete regions manufactured into the surface as described herein.

Methods of Identifying Nucleotide Sequence

In a preferred aspect, random arrays of the invention are used to identify a nucleotide sequence of one or more target polynucleotides. As discussed herein target polynucleotides may be in the form of concatemers, may be linear or circular, and will generally contain one or more target sequences, where the target sequences in a preferred embodiment comprise one or more fragments of the target polynucleotide and are generally shorter in length than the target polynucleotide.

Target sequences can in turn comprise different target domains; for example, a first target domain of the sample target sequence may hybridize to a capture probe and a second target domain may hybridize to a label probe, etc. The target domains may be adjacent to to each other or separated (such as by an adaptor) as indicated. Unless specified, the terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

In a particularly preferred aspect, techniques for identifying polynucleotide sequences are used on polynucleotide molecules that have undergone one or more rounds of amplification, including amplification in solution and in situ.

Techniques for identifying polynucleotide sequences fall into five general categories: (1) techniques that rely on traditional hybridization methods that utilize the variation of stringency conditions (temperature, buffer conditions, etc.) to distinguish nucleotides at the detection position; (2) extension techniques that add a base ("the base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques, that also rely on enzymatic or chemical specificity such that cleavage occurs preferentially if perfect complementarity exists; and (5) techniques that combine these methods. Each of these techniques may be used in a solution based assay, wherein the reaction is done in solution and a reaction product is bound to the array for subsequent detection, or in solid phase assays, where the reaction occurs on the surface and is detected.

Sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, 6,864,052; 6,309,824; 6,401,267 and U.S. Patent Pub. No. 2005/0191656, among others).

Sequencing by synthesis is an alternative to gel-based sequencing. These methods add and read only one base (or at most a few bases, typically of the same type) prior to polymerization of the next base. This can be referred to as "time resolved" sequencing, to contrast from "gel-resolved" sequencing. Sequencing by synthesis has been described in U.S. Pat. Nos. 4,971,903; 6,828,100; 6,833,256; 6,911,345, as well as in Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al (1998), Science, 281: 363-365; Nyren et al., Anal. Biochem. 151:504

(1985); and Li et al, Proc. Natl. Acad. Sci., 100: 414-419 (2003). One promising sequencing by synthesis method is based on the detection of the pyrophosphate (PPi) released during the DNA polymerase reaction. As nucleotriphosphates are added to a growing nucleic acid chain, they release PPi. This release can be quantitatively measured by the conversion of PPi to ATP by the enzyme sulfurylase, and the subsequent production of visible light by firefly luciferase.

Detection of ATP sulfurylase activity is described in Karamohamed and Nyren, Anal. Biochem. 271:81 (1999). Sequencing using reversible chain terminating nucleotides is described in U.S. Pat. Nos. 5,902,723 and 5,547,839, and Canard and Arzumanov, Gene 11:1 (1994), and Dyatkina and Arzumanov, Nucleic Acids Symp Ser 18:117 (1987). Reversible chain termination with DNA ligase is described in U.S. Pat. No. 5,403,708. Time resolved sequencing is described in Johnson et al., Anal. Biochem. 136:192 (1984). Single molecule analysis is described in U.S. Pat. No. 5,795,782 and Elgen and Rigler, Proc. Natl. Acad Sci USA 91(13):5740 (1994), all of which are hereby expressly incorporated by reference in their entirety. Several assay systems have been described that capitalize on this mechanism. See for example WO93/23564, WO 98/28440 and WO98/13523, all of which are expressly incorporated by reference. A preferred method is described in Ronaghi et al., Science 281:363 (1998). In this method, the four deoxynucleotides (dATP, dGTP, dCTP and dTTP; collectively dNTPs) are added stepwise to a partial duplex comprising a sequencing primer hybridized to a single stranded DNA template and incubated with DNA polymerase, ATP sulfurylase, luciferase, and optionally a nucleotide-degrading enzyme such as apyrase. A. dNTP is only incorporated into the growing DNA strand if complimentary to the base in the template strand. The synthesis of DNA is accompanied by the release of PPi equal in molarity to the incorporated dNTP. The PPi is converted to ATP and the light generated by the luciferase is directly proportional to the amount of ATP. In some cases the unincorporated dNTPs and the produced ATP are degraded between each cycle by the nucleotide degrading enzyme.

Ligation-based methods of sequencing are also known in the art, see e.g., Shendure et al (2005), Science, 309: 1728-1739.

The oligonucleotide ligation assay (OLA; sometimes referred to as the ligation chain reaction (LCR)) involves the ligation of at least two smaller probes into a single long probe, using the target sequence as the template for the ligase. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference.

Sequencing using mass spectrometry techniques have also been described; see Koster et al., Nature Biotechnology 14:1123 (1996).

Many of the above described methods require a primer nucleic acid (including nucleic acid analogs) that is hybridized to a target sequence to form a hybridization complex, and an enzyme is added that in some way modifies the primer to form a modified primer. For example, PCR generally requires two primers, dNTPs and a DNA polymerase; LCR requires two primers that adjacently hybridize to the target sequence and a ligase; CPT requires one cleavable primer and a cleaving enzyme; invasive cleavage requires two primers and a cleavage enzyme; etc. Thus, in general, a target nucleic acid is added to a reaction mixture that comprises the necessary amplification components, and a modified primer is formed. In general, the modified primer comprises a detectable label, such as a fluorescent label, which is either incorporated by the enzyme or present on the original primer. As required, the unreacted primers are removed, in a variety of ways, as will be appreciated by those in the art and outlined herein. The modified primer can be detected and/or quantified using methods known in the art, and its presence can be used to identify and quantify the associated target sequence(s). In some cases, the newly modified primer serves as a target sequence for a secondary reaction, which then produces a number of amplified strands, which can also be detected as described herein.

In a preferred aspect, sequencing techniques known in the art and described herein are employed on concatemers comprising target sequences. As discussed herein, target sequences can be prepared using known techniques. Once prepared, the target sequence can be used in a variety of reactions for a variety of reasons. For example, in a specific aspect of the invention, genotyping reactions are done. Similarly, these reactions can also be used to detect the presence or absence of a target sequence. In addition, in any reaction, quantitation of the amount of a target sequence may be done. While the discussion below focuses on genotyping reactions, the discussion applies equally to detecting the presence of target sequences and/or their quantification. Furthermore, in accordance with the invention, any sequencing techniques described using random arrays are also applicable to random arrays which have undergone one or more rounds of in situ amplification.

In a preferred aspect of specific embodiments, a target sequence comprises a position for which sequence information is desired, generally referred to herein as the "detection position" or "detection locus". In a particularly preferred aspect of specific embodiments, the detection position is a single nucleotide, although in some aspects, it may comprise a plurality of nucleotides, either contiguous with each other or separated by one or more nucleotides. By "plurality" as used herein is meant at least two. As used herein, the base which basepairs with a detection position base in a hybrid is termed a "readout position" or an "interrogation position". "Readout" means a parameter, or parameters, which are measured and/or detected that can be converted to a number or value. In some contexts, readout may refer to an actual numerical representation of such collected or recorded data. For example, a readout of fluorescent intensity signals from a microarray is the position and fluorescence intensity of a signal being generated at each hybridization site of the microarray; thus, such a readout may be registered or stored in various ways, for example, as an image of the microarray, as a table of numbers, or the like.

In some aspects, as is discussed herein, the target sequence may not be the sample target sequence but instead is a product of a reaction herein, sometimes referred to herein as a "secondary" or "derivative" target sequence. Thus, for example, in a single base extension (SBE) method, the extended primer may serve as the target sequence; similarly, in invasive cleavage variations, the cleaved detection sequence may serve as the target sequence.

In one aspect, a method of determining a nucleotide sequence of a target polynucleotide in accordance with the invention comprises the following steps: (a) generating a plurality of target concatemers from the target polynucleotide, each target concatemer comprising multiple copies of a fragment of the target polynucleotide and the plurality of target concatemers including a number of fragments that substantially covers the target polynucleotide; (b) forming a random array of target concatemers fixed to a surface at a density such that at least a majority of the target concatemers are optically resolvable; (c) identifying a sequence of at least a portion of each fragment in each target concatemer; and (d)

reconstructing the nucleotide sequence of the target polynucleotide from the identities of the sequences of the portions of fragments the concatemers.

As used herein, "substantially covers" means that the amount of nucleotides (i.e., target sequences) analyzed contains an equivalent of at least two copies of the target polynucleotide, or in another aspect, at least ten copies, or in another aspect, at least twenty copies, or in another aspect, at least 100 copies. Target polynucleotides may include DNA fragments, including genomic DNA fragments and cDNA fragments, and RNA fragments. Guidance for the step of reconstructing target polynucleotide sequences can be found in the following references, which are incorporated by reference: Lander et al, Genomics, 2: 231-239 (1988); Vingron et al, J. Mol. Biol., 235: 1-12 (1994); and like references.

In one aspect, a sequencing method for use with the invention for determining sequences in a plurality of DNA or RNA fragments comprises the following steps: (a) generating a plurality of polynucleotide molecules each comprising a concatemer of a DNA or RNA fragment; (b) forming a random array of polynucleotide molecules fixed to a surface at a density such that at least a majority of the target concatemers are optically resolvable; and (c) identifying a sequence of at least a portion of each DNA or RNA fragment in resolvable polynucleotides using at least one chemical reaction of an optically detectable reactant. In a preferred aspect of specific embodiments, the array of polynucleotide molecules has undergone at least one round of in situ amplification.

In a further aspect of specific embodiments, the optically detectable reactant used in identifying the sequence is an oligonucleotide. In another aspect, the optically detectable reactant is a nucleoside triphosphate, e.g., a fluorescently labeled nucleoside triphosphate that may be used to extend an oligonucleotide hybridized to a concatemer. In another aspect, the optically detectable reagent is an oligonucleotide formed by ligating a first and second oligonucleotides that form adjacent duplexes on a concatemer. In another aspect, the chemical reaction of an optically detectable reactant is synthesis of DNA or RNA, e.g., by extending a primer hybridized to a concatemer. In yet another aspect, the optically detectable reactant is a nucleic acid binding oligopeptide or polypeptide or protein.

In one aspect, parallel sequencing of polynucleotide analytes of concatemers on a random array is accomplished by combinatorial SBH (cSBH). In a preferred aspect, a first and second sets of oligonucleotide probes (also referred to herein as "label probes") are provided, wherein each sets has member probes that comprise oligonucleotides having every possible sequence for the defined length of probes in the set. For example, if a set contains probes of length six, then it contains 4096 (=$4^6$) probes. In another aspect, first and second sets of oligonucleotide probes comprise probes having selected nucleotide sequences designed to detect selected sets of target polynucleotides. Sequences are determined by hybridizing one probe or pool of probe, hybridizing a second probe or a second pool of probes, ligating probes that form perfectly matched duplexes on their target sequences, identifying those probes that are ligated to obtain sequence information about the target sequence, repeating the steps until all the probes or pools of probes have been hybridized, and determining the nucleotide sequence of the target from the sequence information accumulated during the hybridization and identification steps.

In one aspect of specific embodiments, the sets may be divided into subsets that are used together in pools, as disclosed in U.S. Pat. No. 6,864,052. Probes from the first and second sets may be hybridized to target sequences either together or in sequence, either as entire sets or as subsets, or pools. In one aspect, lengths of the probes in the first or second sets are in the range of from 5 to 10 nucleotides, and in another aspect, in the range of from 5 to 7 nucleotides, so that when ligated they form ligation products with a length in the range of from 10 to 20, and from 10 to 14, respectively.

In another aspect, the sequence identity of each attached DNA concatemer may be determined by a "signature" approach. About 50 to 100 or possibly 200 probes are used such that about 25-50% or in some applications 10-30% of attached concatemers will have a full match sequence for each probe. This type of data allows each amplified DNA fragment within a concatemer to be mapped to the reference sequence. For example, by such a process one can score 64 4-mers (i.e. 25% of all possible 256 4-mers) using 16 hybridization/stripoff cycles in a 4 colors labeling schema. On a 60-70 base fragment amplified in a concatemer about 16 of 64 probes will be positive since there are 64 possible 4mers present in a 64 base long sequence (i.e. one quarter of all possible 4mers). Unrelated 60-70 base fragments will have a very different set of about 16 positive decoding probes. A combination of 16 probes out of 64 probes has a random chance of occurrence in 1 of every one billion fragments which practically provides a unique signature for that concatemer. Scoring 80 probes in 20 cycles and generating 20 positive probes create a signature even more likely to be unique: occurrence by chance is 1 in a billion billions. Previously, a "signature" approach was used to select novel genes from cDNA libraries. An implementation of a signature approach is to sort obtained intensities of all tested probes and select up to a predefined (expected) number of probes that satisfy the positive probe threshold. These probes will be mapped to sequences of all DNA fragments (sliding window of a longer reference sequence may be used) expected to be present in the array. The sequence that has all or a statistically sufficient number of the selected positive probes is assigned as the sequence of the DNA fragment in the given concatemer. In another approach an expected signal can be defined for all used probes using their pre measured full match and mismatch hybridization/ligation efficiency. In this case a measure similar to the correlation factor can be calculated.

In an exemplary aspect, 4-mers (probes 4 bases in length) are scored through ligation of pairs of probes, for example: $N_{(5-7)}$BBB with BN$_{(7-9)}$, where B is the defined base and N is a degenerate base. For generating signatures on longer DNA concatemer probes, more unique bases will be used. For example, a 25% positive rate in a fragment 1000 bases in length would be achieved by $N_{(4-6)}$BBBB and BBN$_{(6-8)}$. Note that longer fragments need the same number of about 60-80 probes (15-20 ligation cycles using 4 colors). In one aspect all probes of a given length (e.g., 4096 $N_{2-4}$BBBBBBN$_{2-4}$) or all ligation pairs may be used to determine complete sequence of the DNA in a concatemer. For example, 1024 combinations of $N_{(5-7)}B_3$ and BBN$_{(6-8)}$ may be scored (256 cycles if 4 colors are used) to determine sequence of DNA fragments of up to about 250 bases, preferably up to about 100 bases.

The decoding of sequencing probes with large numbers of Ns may be prepared from multiple syntheses of subsets of sequences at degenerated bases to minimize difference in the efficiency. Each subset is added to the mix at a proper concentration. Also, some subsets may have more degenerated positions than others. For example, each of 64 probes from the set $N_{(5-7)}$BBB may be prepared in 4 different synthesis. One is regular all 5-7 bases to be fully degenerated; second is N0-3(A,T)5BBB; third is N0-2(A,T)(G,C)(A,T)(G,C)(A,T) BBB, and the fourth is N0-2(G,C)(A,T)(G,C)(A,T)(G,C) BBB.

Oligonucleotide preparation from the three specific syntheses is added in to regular synthesis in experimentally determined amounts to increase hybrid generation with target sequences that have in front of the BBB sequence an AT rich (e.g., AATAT) or (A or T) and (G or C) alternating sequence (e.g., ACAGT or GAGAC). These sequences are expected to be less efficient in forming a hybrid. All 1024 target sequences can be tested for the efficiency to form hybrid with $N_{0-3}$NNNNNBBB probes and those types that give the weakest binding may be prepared in about 1-10 additional synthesis and added to the basic probe preparation.

In another exemplary aspect of specific embodiments, 12 bases of a target concatemer are decoded using a combination of hybridization and ligation based assays. In this aspect, one half of the sequence is determined by utilizing the hybridization specificity of short probes and the ligation specificity of fully matched hybrids. Six to ten bases adjacent to the 12 mer are predefined and act as a support for a 6mer to 10-mer oligonucleotide. This short 6mer will ligate at its 3-prime end to one of 4 labeled 6-mers to 10-mers. These decoding probes consist of a pool of 4 oligonucleotides in which each oligonucleotide consists of 4-9 degenerate bases and 1 defined base. This oligonucleotide will also be labeled with one of four fluorescent labels. Each of the 4 possible bases A, C, G, or T will therefore be represented by a fluorescent dye. For example these 5 groups of 4 oligonucleotides and one universal oligonucleotide (Us) can be used in the ligation assays to sequence first 5 bases of 12-mers: B=each of 4 bases associated with a specific dye or tag at the end:

UUUUUUUU.BNNNNNNN
UUUUUUUU.NBNNNNNN
UUUUUUUU.NNBNNNNN
UUUUUUUU.NNNBNNNN
UUUUUUUU.NNNNBNNN

Six or more bases can be sequenced with additional probe pools. To improve discrimination at positions near the center of the 12mer (the 12 bases of the concatemer being sequenced) the 6mer oligonucleotide can be positioned further into the 12mer sequence. This will necessitate the incorporation of degenerate bases into the 3-prime end of the non-labeled oligonucleotide to accommodate the shift. This is an example of decoding probes for position 6 and 7 in the 12-mer.

UUUUUUNN.NNNBNNNN
UUUUUUNN.NNNNBNNN

In a similar way the 6 bases from the right side of the 12mer can be decoded by using a fixed oligonucleotide and 5-prime labeled probes. In the above described system 6 cycles are required to define 6 bases of one side of the 12mer. With redundant cycle analysis of bases distant to the ligation site this may increase to 7 or 8 cycles. In total then, complete sequencing of the 12mer could be accomplished with 12-16 cycles of ligation.

In another exemplary aspect, polynucleotide molecules on a random array can be sequenced combining two distinct types of libraries of detector probes. In this approach one library has probes of the general type $N_{3-8}B_{4-6}$ (anchors) that are ligated with the first 2 or 3 or 4 probes/probe pools from the other set $BN_{6-8}$, $NBN_{5-7}$, $N_2BN_{4-6}$, and $N_3BN_{3-5}$. In this aspect, a few cycles are used to test a probe from the first library with 2-4 or even more probes from the second library in order to read longer continuous sequences (such as 5–6+ 3–4=8–10) in just 3-4 cycles. One or more of the probes in one or both libraries can be tagged using physical and chemical design (such as by adding a specific number of bases to provide a distinct hybrid stability, or altering GC content to affect stability), and through labels such as fluorescent labels.

Using multiple colors or other labels allows for parallel and multiplex sequencing of a random array. In one exemplary aspect probes are tagged with different oligonucleotide sequences made of natural bases or new synthetic bases (such as isoG and isoC). Tags can be designed to have very precise binding efficiency with their anti-tags using different oligonucleotide lengths (about 6-24 bases) and/or sequence including GC content. For example 4 different tags may be designed that can be recognized with specific anti-tags in 4 consecutive cycles or in one hybridization cycle followed by a discriminative wash. In the discriminative wash initial signal is reduced to 95-99%, 30-40%, 10-20% and 0-5% for each tag, respectively. In this case by obtaining two images 4 measurements are obtained assuming that probes with different tags will rarely hybridize to the same dot. Another benefit of having many different tags even if they are consecutively decoded (or 2-16 at a time labeled with 2-16 distinct colors) is the ability to use a large number of individually recognizable probes in one assay reaction. This way a 4-64 times longer assay time (that may provide more specific or stronger signal) may be affordable if the probes are decoded in short incubation and removal reactions.

In some aspects, the decoding process requires the use of 48-96 or more decoding probes. These pools will be further combined into 12-24 or more pools by encoding them with four fluorophores, each having different emission spectra. Each array requires about 12-24 cycles to decode. Each cycle consists of a hybridization, wash, array imaging, and strip-off step. These steps, in their respective orders, may take for the above example 5, 2, 12, and 5 minutes each, for a total of 24 minutes each cycle, or roughly 5-10 hours for each array, if the operations were performed linearly. The time to decode each array can be reduced by a factor of two by allowing the system to image constantly. To accomplish this, the imaging of two separate substrates on each microscope is staggered. While one substrate is being reacted, the other substrate is imaged.

In another exemplary aspect of specific embodiments, a decoding cycle using combinatorial sequencing by hybridization (cSBH) includes the following steps: (i) set temperature of array to hybridization temperature (usually in the range 5-25° C.); (ii) use robot pipetter to pre mix a small amount of decoding probe with the appropriate amount of hybridization buffer; (iii) pipette mixed reagents into hybridization chamber; (iv) hybridize for predetermined time; (v) drain reagents from chamber using pump (syringe or other); (vi) add a buffer to wash mismatches of non-hybrids; (vii) adjust chamber temperature to appropriate wash temp (about 10-40° C.); (viii) drain chamber; (ix) add more wash buffer if needed to improve imaging; (x) image each array, (xii) remove buffer; and (xiii) start the next hybridization cycle with the next decoding probe pool in set.

In one aspect, polynucleotide molecules amplified using NASBA and TMA methods can be directly detected when the newly synthesized strands comprise detectable labels, either by incorporation into the primers or by incorporation of modified labeled nucleotides into the growing strand. Alternatively, indirect detection of unlabelled strands (which now serve as "targets" in the detection mode) can occur using a variety of sandwich assay configurations. As will be appreciated by those in the art, any of the newly synthesized strands can serve as the "target" for form an assay complex on a surface with a capture probe. In NASBA and TMA, it is preferable to utilize the newly formed RNA strands as the target, as this is where significant amplification occurs.

In another aspect, Invader™ technology is used to detect and identify nucleotide sequence. This technology is based on structure-specific polymerases that cleave nucleic acids in a site-specific manner. Two probes are used: an "invader" probe and a "signaling" probe that adjacently hybridize to a target sequence with a non-complementary overlap. The enzyme cleaves at the overlap due to its recognition of the "tail", and releases the "tail" with a label. This can then be detected. The Invader™ technology is described in U.S. Pat. Nos. 5,846, 717; 5,614,402; 5,719,028; 5,541,311; and 5,843,669, all of which are hereby incorporated by reference.

In another aspect, products from an oligonucleotide ligation amplification (OLA) technique are detected in order to identify a nucleotide sequence of a polynucleotide molecule. As will be appreciated by those in the art, the ligation product can be detected in a variety of ways. In a preferred aspect of specific embodiments, the ligation reaction is run in solution. In this aspect, only one of the primers carries a detectable label, e.g., the first ligation probe, and the capture probe on the bead is substantially complementary to the other probe, e.g., the second ligation probe. In this way, unextended labeled ligation primers will not interfere with the assay. That is, in a preferred aspect of specific embodiments, the ligation product is detected by solid-phase oligonucleotide probes. The solid-phase probes are preferably complementary to at least a portion of the ligation product. In a preferred aspect, the solid-phase probe is complementary to the 5' detection oligonucleotide portion of the ligation product. This substantially reduces or eliminates false signal generated by the optically-labeled 3' primers. Preferably, detection is accomplished by removing the unligated 5' detection oligonucleotide from the reaction before application to a capture probe. In one aspect, the unligated 5' detection oligonucleotides are removed by digesting 3' non-protected oligonucleotides with a 3' exonuclease, such as, exonuclease I. The ligation products are protected from exo I digestion by including, for example, 4-phosphorothioate residues at their 3' terminus, thereby, rendering them resistant to exonuclease digestion. The unligated detection oligonucleotides are not protected and are digested. Alternatively, the target nucleic acid is immobilized on a solid-phase surface and a ligation assay is performed and unligated oligonucleotides are removed by washing under appropriate stringency to remove unligated oligonucleotides. The ligated oligonucleotides are eluted from the target nucleic acid using denaturing conditions, such as, 0.1 N NaOH, and detected as described herein.

The detection of products from an LCR reaction can also occur directly, in the case where one or both of the primers comprises at least one detectable label, or indirectly, using sandwich assays, through the use of additional probes; that is, the ligated probes can serve as target sequences, and detection may utilize amplification probes, capture probes, capture extender probes, label probes, and label extender probes, etc.

In one aspect, if an invasive cleavage reaction is used to amplify polynucleotide molecules, the products of the reaction can be detected by designing the probes to utilize a fluorophore-quencher reaction. A signaling probe comprising both a fluorophore and a quencher is used, with the fluorophore and the quencher on opposite sides of the cleavage site. As will be appreciated by those in the art, these will be positioned closely together. Thus, in the absence of cleavage, very little signal is seen due to the quenching reaction. After cleavage, however, the distance between the two is large, and thus fluorescence can be detected. Upon assembly of an assay complex, comprising the target sequence, an invader probe, and a signaling probe, and the introduction of the cleavage enzyme, the cleavage of the complex results in the disassociation of the quencher from the complex, resulting in an increase in fluorescence. In this aspect, suitable fluorophore-quencher pairs are as known in the art. For example, suitable quencher molecules comprise DABCYL.

In a preferred aspect of specific embodiments, straight hybridization methods are used to elucidate the identity of the base at the detection position. Generally speaking, these techniques break down into two basic types of reactions: those that rely on competitive hybridization techniques, and those that discriminate using stringency parameters and combinations thereof.

In one aspect of specific embodiments, the use of competitive hybridization probes is done to elucidate either the identity of the nucleotide(s) at the detection position or the presence of a mismatch. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

In one aspect of specific embodiments, a plurality of probes (sometimes referred to herein as "readout probes") are used to identify the base at the detection position. In this aspect, each different readout probe comprises a different detection label (which, as outlined below, can be either a primary label or a secondary label) and a different base at the position that will hybridize to the detection position of the target sequence (herein referred to as the readout position) such that differential hybridization will occur. That is, all other parameters being equal, a perfectly complementary readout probe (a "match probe") will in general be more stable and have a slower to disassociate than a probe comprising a mismatch (a "mismatch probe") at any particular temperature. Accordingly, by using different readout probes, each with a different base at the readout position and each with a different label, the identification of the base at the detection position is elucidated. In a preferred aspect of specific embodiments, a set of readout probes are used, each comprising a different base at the readout position. In some aspects, each readout probe comprises a different label that is distinguishable from the others. In one aspect, the length and sequence of each readout probe is identical except for the readout position, although this need not be true in all embodiments.

Label Probes

As described above, in one aspect, an adaptor can comprise one or more binding sequences for a detectable tag, such as a label probe. In some aspects, label probes can be added to the concatemers to detect particular sequences. Label probes will hybridize to the label probe binding sequence and comprise at least one detectable label. Such labels include without limitation the direct or indirect attachment of radioactive moieties, fluorescent moieties, colorimetric moieties, chemiluminescent moieties, and the like.

In one aspect, one or more fluorescent dyes are used as labels for the label probes (also referred to herein as "oligonucleotide probes"), e.g., as disclosed by Menchen et al, U.S. Pat. No. 5,188,934 (4,7-dichlorofluorscein dyes); Begot et al, U.S. Pat. No. 5,366,860 (spectrally resolvable rhodamine dyes); Lee et al, U.S. Pat. No. 5,847,162 (4,7-dichlororhodamine dyes); Khanna et al, U.S. Pat. No. 4,318,846 (ether-substituted fluorescein dyes); Lee et al, U.S. Pat. No. 5,800, 996 (energy transfer dyes); Lee et al, U.S. Pat. No. 5,066,580 (xanthene dyes): Mathies et al, U.S. Pat. No. 5,688,648 (energy transfer dyes); and the like. Labeling can also be carried out with quantum dots, as disclosed in the following patents and patent publications, incorporated herein by reference: U.S. Pat. Nos. 6,322,901; 6,576,291; 6,423,551; 6,251,303; 6,319,426; 6,426,513; 6,444,143; 5,990,479; 6,207,392; 2002/0045045; 2003/0017264; and the like. As used herein, the term "fluorescent signal generating moiety" means a signaling means which conveys information through the fluorescent absorption and/or emission properties of one or more molecules. Such fluorescent properties include fluorescence intensity, fluorescence life time, emission spectrum characteristics, energy transfer, and the like.

Commercially available fluorescent nucleotide analogues readily incorporated into label probes include, for example, Cy3-dCTP, Cy3-dUTP, Cy5-dCTP, Cy5-dUTP (Amersham Biosciences, Piscataway, N.J., USA), fluorescein-12-dUTP, tetramethylrhodamine-6-dUTP, Texas Red®-5-dUTP, Cascade Blue®-7-dUTP, BODIPY® FL-14-dUTP, BODIPY®R-14-dUTP, BODIPY® TR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, Cascade Blue®-7-UTP, BODIPY® FL-14-UTP, BODIPY® TMR-14-UTP, BODIPY® TR-14-UTP, Rhodamine Green™-5-UTP, Alexa Fluor® 488-5-UTP, Alexa Fluor® 546-14-UTP (Molecular Probes, Inc. Eugene, Oreg., USA). Other fluorophores available for post-synthetic attachment include, inter alia, Alexa Fluor® 350, Alexa Fluor® 532, Alexa Fluor® 546, Alexa Fluor® 568, Alexa Fluor® 594, Alexa Fluor® 647, BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3.5, Cy5.5, and Cy7 (Amersham Biosciences, Piscataway, N.J. USA, and others). FRET tandem fluorophores may also be used, such as PerCP-Cy5.5, PE-Cy5, PE-Cy5.5, PE-Cy7, PE-Texas Red, and APC-Cy7; also, PE-Alexa dyes (610, 647, 680) and APC-Alexa dyes. Biotin, or a derivative thereof, may also be used as a label on a detection oligonucleotide, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a detection oligonucleotide and subsequently coupled to an N-hydroxy succinimide (NHS) derivitized fluorescent dye, such as those listed supra. In general, any member of a conjugate pair may be incorporated into a detection oligonucleotide provided that a detectably labeled conjugate partner can be bound to permit detection. As used herein, the term antibody refers to an antibody molecule of any class, or any subfragment thereof, such as an Fab. Other suitable labels for detection oligonucleotides may include fluorescein (FAM), digoxigenin, dinitrophenol (DNP), dansyl, biotin, bromodeoxyuridine (BrdU), hexahistidine (6×His), phosphor-amino acids (e.g., P-tyr, P-ser, P-thr), or any other suitable label. In one aspect the following hapten/antibody pairs are used for detection, in which each of the antibodies is derivatized with a detectable label: biotin/α-biotin, digoxigenin/α-digoxigenin, dinitrophenol (DNP)/α-DNP, 5-Carboxyfluorescein (FAM)/α-FAM. As described in schemes below, probes may also be indirectly labeled, especially with a hapten that is then bound by a capture agent, e.g., as disclosed in Holtke et al, U.S. Pat. Nos. 5,344,757; 5,702,888; and 5,354,657; Huber et al, U.S. Pat. No. 5,198,537; Miyoshi, U.S. Pat. No. 4,849,336; Misiura and Gait, PCT publication WO 91/17160; and the like. Many different hapten-capture agent pairs are available for use with the invention. Exemplary, haptens include, biotin, des-biotin and other derivatives, dinitrophenol, dansyl, fluorescein, CY5, and other dyes, digoxigenin, and the like. For biotin, a capture agent may be avidin, streptavidin, or antibodies. Antibodies may be used as capture agents for the other haptens (many dye-antibody pairs being commercially available, e.g., Molecular Probes).

In one aspect, pools of label probes are provided which preferably have from about 1 to about 3 bases, allowing for an even and optimized signal for different sequences at degenerate positions. In another aspect, a concentration adjusted mix of 3-mer building blocks is used in the probe synthesis.

Label probes may be prepared with nucleic acid tag tails instead of being directly labeled. Tails preferably do not interact with target polynucleotides. These tails may be prepared from natural bases or modified bases such as isoC and isoG that pair only between themselves. If isoC and isoG nucleotides are used, the sequences may be separately synthesized with a 5' amino-linker, which allows conjugation to a 5' carboxy modified linker that is synthesized on to each tagged probe. This allows separately synthesized tag sequences to be combined with known probes while they are still attached to the column. In one aspect, 21 tagged sequences are used in combination with 1024 known probes.

The tails may be separated from probes by 1-3 or more degenerated bases, abasic sites or other linkers. One approach to minimize interaction of tails and target DNA is to use sequences that are very infrequent in the target DNA. For example, CGCGATATCGCGATAT—(SEQ ID NO: 10)—or CGATCGATCGAT—(SEQ ID NO: 11)—is expected to be infrequent in mammalian genomes. One option is to use probe with tails pre-hybridized with unlabeled tags that would be denatured and maybe washed away after ligation and before hybridization with labeled tags. Uracil may be used to generate degradable tails/tags and to remove them before running a new cycle instead of using temperature removal;

In one aspect high-plex multiplex ligation assays of probes are used which are not labeled with fluorescent dyes, thus reducing background and assay costs. For example for 8 colors 4×8=32 different encoding tails may be prepared and 32 probes as a pool may be used in hybridization/ligation. In the decoding process, four cycles each with 8 tags are used. Thus, each color is used for 4 tags used in 4 decoding cycles. After each cycle, tags may be removed or dyes photo bleached. The process requires that the last set of probes to be decoded has to stay hybridized through 4 decoding cycles.

In one aspect, additional properties are included to provide the ability to distinguish different probes using the same color, for example Tm/stability, degradability by incorporated uracil bases and UDG enzyme, and chemically or photochemically cleavable bonds. A combination of two properties, such as temperature stability directly or after cutting or removing a stabilizer to provide 8 distinct tags for the same color; more than one cut type may be used to create 3 or more groups; to execute this 4-8 or 6-12 exposures of the same color may be required, demanding low photo-bleaching conditions such as low intensity light illumination that may be detected by intensified CCDs (ICCDs). For example if one property is melting temperature (Tm) and there are 4 tag-oligos or anchors or primers with distinct Tm, another set of 4 oligos can be prepared that has the first 4 probes connected to or intractable with a stabilizer that shifts the Tm of these 4 oligos above the most stable oligo in the first group without stabilizer. After resolving 4 oligos from the first group by consecutive melting off, the temperature may be reduced to the initial low level, the stabilizer may be cut or removed, and 4 tagged-oligos or anchors or primers can then be differentially melted using the same temperature points as for the first group.

In one aspect, probe-probe hybrids are stabilized through ligation to another unlabeled oligonucleotide, such as an anchor probe.

As mentioned above, random arrays of biomolecules, such as genomic DNA fragments or cDNA fragments, provides a platform for large scale sequence determination and for genome-wide measurements based on counting sequence tags, in a manner similar to measurements made by serial analysis of gene expression (SAGE) or massively parallel signature sequencing, e.g., Velculescu, et al, (1995), Science 270, 484-487; and Brenner et al (2000), Nature Biotechnology, 18: 630-634. Such genome-wide measurements include, but are not limited to, determination of polymorphisms, including nucleotide substitutions, deletions, and insertions, inversions, and the like, determination of methylation patterns, copy number patterns, and the like, such as could be carried out by a wide range of assays known to those with ordinary skill in the art, e.g., Syvanen (2005), Nature Genetics Supplement, 37: S5-S10; Gunderson et al (2005), Nature Genetics, 37: 549-554; Fan et al (2003), Cold Spring Harbor Symposia on Quantitative Biology, LXVIII: 69-78; and U.S. Pat. Nos. 4,883,750; 6,858,412; 5,871,921; 6,355,431; and the like, which are incorporated herein by reference.

Detection Instrumentation

As mentioned above, signals from single molecules on random arrays made in accordance with the invention are generated and detected by a number of detection systems, including, but not limited to, scanning electron microscopy, near field scanning optical microscopy (NSOM), total internal reflection fluorescence microscopy (TIRFM), and the like. Abundant guidance is found in the literature for applying such techniques for analyzing and detecting nanoscale structures on surfaces, as evidenced by the following references that are incorporated by reference: Reimer et al, editors, Scanning Electron Microscopy: Physics of Image Formation and Microanalysis, 2$^{nd}$ Edition (Springer, 1998); Nie et al, Anal. Chem., 78: 1528-1534 (2006); Hecht et al, Journal Chemical Physics, 112: 7761-7774 (2000); Zhu et al, editors, Near-Field Optics: Principles and Applications (World Scientific Publishing, Singapore, 1999); Drmanac, International patent publication WO 2004/076683; Lehr et al, Anal. Chem., 75: 2414-2420 (2003); Neuschafer et al, Biosensors & Bioelectronics, 18: 489-497 (2003); Neuschafer et al, U.S. Pat. No. 6,289,144; and the like. Of particular interest is TIRFM, for example, as disclosed by Neuschafer et al, U.S. Pat. No. 6,289,144; Lehr et al (cited above); and Drmanac, International patent publication WO 2004/076683.

In one aspect, instruments for use with arrays of the invention comprise three basic components: (i) a fluidics system for storing and transferring detection and processing reagents, e.g., probes, wash solutions, and the like, to an array; (ii) a reaction chamber, or flow cell, holding or comprising an array and having flow-through and temperature control capability; and (iii) an illumination and detection system. In one aspect, a flow cell has a temperature control subsystem with ability to maintain temperature in the range from about 5-95° C., or more specifically 10-85° C., and can change temperature with a rate of about 0.5-2° C. per second.

In an exemplary aspect of specific embodiments, a 20× objective is used, and a 6 mm×6 mm array may require roughly 30 images for full coverage by using a 10 mega pixel camera. Each of 1 micrometer array areas is read by about 8 pixels. Each image is acquired in 250 ms, 150 ms for exposure and 100 ms to move the stage. Using this fast acquisition it will take ~7.5 seconds to image each array, or 12 minutes to image the complete set of 96 arrays on each substrate. In one aspect of an imaging system, this high image acquisition rate is achieved by using four ten-megapixel cameras, each imaging the emission spectra of a different fluorophore. The cameras are coupled to the microscope through a series of dichroic beam splitters. The autofocus routine, which takes extra time, runs only if an acquired image is out of focus. It will then store the Z axis position information to be used upon return to that section of that array during the next imaging cycle. By mapping the autofocus position for each location on the substrate, it is possible to reduce the time required for image acquisition. Imaging speed may be improved by decreasing the objective magnification power, using grid patterned arrays and increasing the number of pixels of data collected in each image.

For example, up to four or more cameras may be used, preferably in the 10-16 megapixel range. Multiple band pass filters and dichroic mirrors may also be used to collect pixel data across up to four or more emission spectra. To compensate for the lower light collecting power of the decreased magnification objective, the power of the excitation light source can be increased. Throughput can be increased by using one or more flow chambers with each camera, so that the imaging system is not idle while the samples are being hybridized/reacted. Because the probing of arrays can be non-sequential, more than one imaging system can be used to collect data from a set of arrays, further decreasing assay time.

During the imaging process, the substrate must remain in focus. Some key factors in maintaining focus are the flatness of the substrate, orthogonality of the substrate to the focus plane, and mechanical forces on the substrate that may deform it. Substrate flatness can be well controlled, glass plates which have better than ¼ wave flatness are readily obtained. Uneven mechanical forces on the substrate can be minimized through proper design of the hybridization chamber. Orthogonality to the focus plane can be achieved by a well adjusted, high precision stage. Auto focus routines generally take additional time to run, so it is desirable to run them only if necessary. After each image is acquired, it will be analyzed using a fast algorithm to determine if the image is in focus. If the image is out of focus, the auto focus routine will run. It will then store the objectives Z position information to be used upon return to that section of that array during the next imaging cycle. By mapping the objectives Z position at various locations on the substrate, we will reduce the time required for substrate image acquisition.

A suitable illumination and detection system for fluorescence-based signal is a Zeiss Axiovert 200 equipped with a TIRF slider coupled to a 80 milliwatt 532 nm solid state laser. The slider illuminates the substrate through the objective at the correct TIRF illumination angle. TIRF can also be accomplished without the use of the objective by illuminating the substrate though a prism optically coupled to the substrate. Planar wave guides can also be used to implement TIRF on the substrate. Epi illumination can also be employed. The light source can be rastered, spread beam, coherent, incoherent, and originate from a single or multi-spectrum source.

One aspect for the imaging system contains a 20× lens with a 1.25 mm field of view, with detection being accomplished with a 10 megapixel camera. Such a system images approx 1.5 million concatemers attached to the patterned array at 1 micron pitch. Under this configuration there are approximately 6.4 pixels per concatemer. The number of pixels per concatemer can be adjusted by increasing or decreasing the field of view of the objective. For example a 1 mm field of view would yield a value of 10 pixels per concatemer and a 2 mm field of view would yield a value of 2.5 pixels per concatemer. The field of view may be adjusted relative to the magnification and NA of the objective to yield the lowest pixel count per concatemer that is still capable of being resolved by the optics, and image analysis software.

Both TIRF and EPI illumination allow for almost any light source to be used. One illumination schema is to share a common set of monochromatic illumination sources (about 4 lasers for 6-8 colors) amongst imagers. Each imager collects data at a different wavelength at any given time and the light sources would be switched to the imagers via an optical switching system. In such an aspect, the illumination source preferably produces at least 6, but more preferably 8 different wavelengths. Such sources include gas lasers, multiple diode pumped solid state lasers combined through a fiber coupler, filtered Xenon Arc lamps, tunable lasers, or the more novel Spectralum Light Engine, soon to be offered by Tidal Photonics. The Spectralum Light Engine uses prism to spectrally separate light. The spectrum is projected onto a Texas Instruments Digital Light Processor, which can selectively reflect any portion of the spectrum into a fiber or optical connector. This system is capable of monitoring and calibrating the power output across individual wavelengths to keep them constant so as to automatically compensate for intensity differences as bulbs age or between bulb changes.

Successfully scoring 6 billion concatemers through ~350 (~60 per color) images per region over 24 hours may require a combination of parallel image acquisition, increased image acquisition speed, and increased field of view for each imager. Additionally, the imager may support between six to eight colors. Commercially available microscopes commonly image a ~1 mm field of view at 20× magnification with an NA of 0.8. At the proposed concatemer pitch of 0.5 micron, this translates into roughly 4 million concatemers per image. This yields approximately 1,500 images for 6 billion spots per hybridization cycle, or 0.5 million images for 350 imaging cycles. In a large scale sequencing operation, each imager preferably acquires ~200,000 images per day, based on a 300 millisecond exposure time to a 16 mega pixel CCD. Thus, a preferred instrument design is 4 imager modules each serving 4 flow cells (16 flow cells total). The above described imaging schema assumes that each imager has a CCD detector with 10 million pixels and be used with an exposure time of roughly 300 milliseconds. This should be an acceptable method for collecting data for 6 fluorophore labels. One possible drawback to this imaging technique is that certain fluorophores may be unintentionally photo bleached by the light source while other fluorophores are being imaged. Keeping the illumination power low and exposure times to a minimum would greatly reduce photo bleaching. By using intensified CCDs (ICCDs) data could be collected of roughly the same quality with illumination intensities and exposure times that are orders of magnitude lower than standard CCDs. ICCDs are generally available in the 1-1.4 megapixel range. Because they require much shorter exposure times, a one megapixel ICCD can acquire ten or more images in the time a standard CCD acquires a single image. Used in conjunction with fast filter wheels, and a high speed flow cell stage, a one mega pixel ICCD should be able to collect the same amount of data as a 10 megapixel standard CCD.

Kits of the Invention

In the commercialization of the methods described herein, certain kits for construction of random arrays of the invention and for using the same for various applications are particularly useful. In general, kits of the invention can include any random array as described herein as well as reagents and molecules for creating such random arrays.

In one aspect, kits for constructing random arrays of the invention include, but are not limited to, a support having a surface with capture oligonucleotides attached, the capture oligonucleotides having a recognition sequence for a nicking endonuclease upon formation of a duplex with an adaptor oligonucleotide of a concatemer. Such kits may further include reagents for circularizing polynucleotide molecules to form circularized products and for conducting a RCR reaction with such circularized products. Such reagents include ligases, polymerases, dNTPs, buffers, and the like.

In another aspect, kits for constructing random arrays of the invention include tailed primers specific for complements of an adaptor oligonucleotides, wherein tails of the tailed primers are complementary to capture oligonucleotides. In another aspect, kits of the invention include dendrimers having attached to distal branches thereof oligonucleotides. In one aspect, at least one of such oligonucleotides has a free 3' end and is complementary to an adaptor oligonucleotide of a DNA circle, and at least another one of such oligonucleotides has a sequence identical to a portion of the DNA circle so that stable duplexes are formed between such oligonucleotides and a concatemer produced from such DNA circle in an RCR reaction.

Kits for applications of random arrays of the invention include, but are not limited to, kits for determining the nucleotide sequence of a target polynucleotide, kits for large-scale identification of differences between reference DNA sequences and test DNA sequences, kits for profiling exons, and the like. A kit typically comprises at least one support having a surface and one or more reagents necessary or useful for constructing a random array of the invention or for carrying out an application therewith. Such reagents include, without limitation, nucleic acid primers, probes, adaptors, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

In one aspect, the invention provides a kit for making a random array of concatemers of DNA fragments from a source nucleic acid comprising the following components: (i) a support having a surface; and (ii) at least one adaptor for ligating to each DNA fragment and forming a DNA circle therewith, each DNA circle capable of being replicated by a rolling circle replication reaction to form a concatemer that is capable of being randomly disposed on the surface. In such kits, the surface may be a planar surface having an array of discrete regions, wherein each discrete region has a size equivalent to that of said concatemers. The discrete regions may form a regular array with a nearest neighbor distance in the range of from 0.1 to 20 µm. The concatemers on the discrete regions may have a nearest neighbor distance such that they are optically resolvable. The discrete regions may have capture probes attached and the adaptors may each have a region complementary to the capture oligonucleotides such that the concatemers are capable of being attached to the discrete regions by formation of complexes between the capture oligonucleotides and the complementary regions of the adaptor oligonucleotides. In some aspects, the concatemers are randomly distributed on said discrete regions and the nearest neighbor distance is in the range of from 0.3 to 3 µm.

Such kits may further comprise (a) a terminal transferase for attaching a homopolymer tail to said DNA fragments to provide a binding site for a first end of said adaptors, (b) a ligase for ligating a strand of said adaptor oligonucleotide to ends of said DNA fragment to form said DNA circle, (c) a primer for annealing to a region of the strand of said adaptors, and (d) a DNA polymerase for extending the primer annealed to the strand in a rolling circle replication reaction. The above adaptor oligonucleotide may have a second end having a number of degenerate bases in the range of from 4 to 12.

In still another aspect, the invention provides kits for constructing a single molecule array comprising the following components: (i) a support having a surface having reactive functionalities; and (ii) a plurality of macromolecular structures each having a unique functionality and multiple complementary functionalities, the macromolecular structures being capable of being attached randomly on the surface wherein the attachment is formed by one or more linkages formed by reaction of one or more reactive functionalities with one or more complementary functionalities; and wherein the unique functionality is capable of selectively reacting with a functionality on an analyte molecule to form the single molecule array. In some aspects of such kits, the surface is a planar surface having an array of discrete regions containing said reactive functionalities and wherein each discrete region has an area less than 1 µm². In further aspects, the discrete regions form a regular array with a nearest neighbor distance in the range of from 0.1 to 20 µm. In further aspects, the concatemers on the discrete regions have a nearest neighbor distance such that they are optically resolvable. In still further aspects, the macromolecular structures may be concatemers of one or more DNA fragments and wherein the unique functionalities are at a 3' end or a 5' end of the concatemers.

While this invention has been disclosed with reference to specific aspects and embodiments, it is apparent that other embodiments and variations of this invention may be devised by others skilled in the art without departing from the true spirit and scope of the invention.

All patents, patent applications, and other publications cited in this application are incorporated by reference in the entirety.

EXAMPLES

Example 1

Circularization Using Adaptor Segments

In one exemplary protocol, a target sequence is a synthetic oligo T1N (sequence: 5'-NNNNNNNNGCATANCAC-GANGTCATNATCGTNCAAACGTCAGTCCANGAATC-NAGATCCACTTAGANTGNCGNNNNNNNN-3') (SEQ ID NO:1). The target sequence includes an adaptor which actually comprises 2 separate oligonucleotides, or adaptor "segments". The adaptor segment that joins to the 5' end of T1N is BR2-ad (sequence: 5'-TATCATCTGGATGTTAG-GAAGACAAAAGGAAGCTGAGGACATTAACGGAC-3') (SEQ ID NO: 2) and the adaptor segment that joins to the 3' end of T1N is UR3-ext (sequence: 5'-ACCTTCAGACCA-GAT-3') (SEQ ID NO: 3). In this aspect, UR3-ext contains a type IIs restriction enzyme site (Acu I: CTTCAG).

As a first step, BR2-ad is annealed to BR2-temp (sequence 5'-NNNNNNNGTCCGTTAATGTCCTCAG-3') (SEQ ID NO: 4) to form a double-stranded adaptor BR2 adaptor. UR3-ext is annealed to biotinylated UR3-temp (sequence 5'-[BIOTIN]ATCTGGTCTGAAGGTNNNNNNNN-3') (SEQ ID NO: 5) to form a double-stranded adaptor UR3 adaptor. In a preferred aspect, 1 pmol of target T1N is ligated to 25 pmol of BR2 adaptor and 10 pmol of UR3 adaptor in a single ligation reaction containing 50 mM Tris-Cl, pH 7.8, 10% PEG, 1 mM ATP, 50 mg/L BSA, 10 mM MgCl$_2$, 0.3 unit/µl T4 DNA ligase (Epicentre Biotechnologies, WI) and 10 mM DTT) in a final volume of 10 µl. The ligation reaction is incubated in a temperature cycling program of 15° C. for 11 min, 37° C. for 1 min repeated 18 times. The reaction is terminated by heating at 70° C. for 10 min. Excess BR2 adaptors are removed by capturing the ligated products with streptavidin magnetic beads (New England Biolabs, MA). 3.3 µl of 4× binding buffer (2M NaCl, 80 mM Tris HCl pH 7.5) is added to the ligation reaction which is then combined with 15 µg of streptavidin magnetic beads in 1× binding buffer (0.5M NaCl, 20 mM Tris HCl pH 7.5). After 15 min incubation in room temperature, the beads are washed twice with 4 volumes of low salt buffer (0.15M NaCl, 20 mM Tris HCl pH 7.5). Elution buffer (10 mM Tris HCl pH 7.5) is pre-warmed to 70 deg, 10 µl of which is added to the beads at 70° C. for 5 min. After magnetic separation, the supernatant is retained as primary purified sample. This sample is further purified by removing the excess UR3 adaptors with magnetic beads pre-bound with a biotinylated oligo BR-rc-bio (sequence: 5'-[BIOTIN]CTTTTGTCTTCCTAACATCC-3') (SEQ ID NO: 6) that is reverse complementary to BR2-ad similarly as described above. The concentration of the adaptor-target ligated product in the final purified sample is estimated by urea polyacrylamide gel electrophoresis analysis. The circularization is carried out by phosphorylating the ligation products using 0.2 unit/µl T4 polynucleotide kinase (Epicentre Biotechnologies) in 1 mM ATP and standard buffer provided by the supplier, and circularized with ten-fold molar excess of a splint oligo UR3-closing-88 (sequence 5'-AGAT-GATAATCTGGTC-3') (SEQ ID NO: 7) using 0.3 unit/µl of T4 DNA ligase (Epicentre Biotechnologies) and 1 mM ATP. The circularized product is validated by performing RCR reactions as described herein.

Example 2

RCR Reaction

An exemplary RCR reaction protocol is as follows: In a 50 µL reaction mixture, the following ingredients are assembled: 2-50 pmol circular DNA, 0.5 units/µL phage φ29 DNA polymerase, 0.2 µg/µL BSA, 3 mM dNTP, 1×φ29 DNA polymerase reaction buffer (Amersham). The RCR reaction is carried out at 30° C. for 12 hours. In some embodiments, the concentration of circular DNA in the polymerase reaction may be selected to be low (approximately 10-100 billion circles per ml, or 10-100 circles per picoliter) to avoid entanglement and other intermolecular interactions.

Example 3

Preparation of Surface for Constructing Random Arrays

A random array can be constructed on a glass surface. For example, a suitable glass surface may be constructed from microscope cover slips. In one exemplary protocol, microscope cover slips (22 mm sq ~170 μm thick) are placed in Teflon racks. They are soaked in 3 molar KOH in 95% ethanol/water for 2 minutes. They are then rinsed in water, followed by an acetone rinse. This removes surface contamination and prepares the glass for silanization. Plasma cleaning is an alternative to KOH cleaning. Fused silica or quartz may also be substituted for glass. The clean, dry cover slips are immersed in 0.3% 3-aminopropyldimethylethoxysilane, 0.3% water, in acetone. They are left to react for 45 minutes. They are then rinsed in acetone and cured at 100° C. for 1 hour. 3-aminopropyldimethylethoxysilane may be used as a replacement for 3-aminopropyltriethoxysilane because it forms a mono-layer on the glass surface. The monolayer surface provides a lower background. The silanization agent may also be applied using vapor deposition.

3-aminopropyltriethoxysilane tends to form more of a polymeric surface when deposited in solution phase. The amino modified silane is then terminated with a thiocyanate group. This is done in a solution of 10% pyridine and 90% N,N-Dimethylformamide (DMF) using 2.25 mg p-phenylenediisothiocyanate (PDC) per ml of solution. The reaction is run for 2 hours, then the slide is washed in methanol, followed by acetone, and water rinses. The cover slips are then dried and ready to bind probe. There are additional chemistries that can be used to modify the amino group at the end of the silanization agent. For example, glutaraldehyde can be used to modify the amino group at the end of the silanization agent to an aldehyde group which can be coupled to an amino modified oligonucleotide. Capture oligonucleotides are bound to the surface of the cover slide by applying a solution of 10-50 μM capture oligonucleotide in 100 mM sodium bicarbonate in water to the surface. The solution is allowed to dry, and is then washed in water.

It some cases, it can be beneficial to avoid terminating the 3-amino group with PDC and perform a direct conjugation (of the 3-amino end) to the capture oligonucleotide which has been modified with either a carboxyl group or an aldehyde group at the 5' end. In the case of the carboxyl group, the oligonucleotide is applied in a solution that contains EDC (1-Ethyl-3-(3-dimethylaminopropyl)-carbodiimide). In the case of the aldehyde group, the oligonucleotide is kept wet for 5-10 minutes, and then the surface is treated with a 1% solution of sodium borohydride.

What is claimed is:

1. A random array of polynucleotides, wherein said random array comprises:
   a) a substrate having a surface; and
   b) a plurality of concatemer extension products disposed on said surface, wherein:
      i) said plurality of concatemer extension products is formed from in situ amplification of immobilized concatemers, and
      ii) each of said immobilized concatemers comprises multiple copies of a monomer, and said monomer comprises a first interspersed adaptor that is located between a first and second target sequence of a target polynucleotide, wherein said first and second target sequences are contiguous segments of said target polynucleotide.

2. The random array of claim 1, wherein:
   a) said surface comprises capture probes, and
   b) said plurality of concatemer extension products are immobilized to said surface through duplexes formed between said concatemer extension products and said capture probes.

3. The random array of claim 2, wherein said capture probes are distributed in discrete regions on said surface, and wherein areas surrounding said discrete regions do not bind said immobilized concatemers or said concatemer extension products.

4. A random array of target polynucleotides of unknown sequence, wherein said random array comprises a substrate having a surface and a plurality of concatemer extension products disposed on said surface, wherein:
   (a) said plurality of concatemer extension products is formed from in situ amplification of immobilized concatemers, and
   (b) said immobilized concatemers are formed from rolling circle replication of a circular template that comprises:
      (i) a first target sequence of a target polynucleotide;
      (ii) a first interspersed adaptor;
      (iii) a second target sequence of said target polynucleotide, wherein said first and second target sequences are contiguous segments of said target polynucleotide and said first interspersed adaptor is located between said first and second target sequence.

5. The random array of claim 4, wherein:
   a) said surface comprises capture probes, and
   b) said plurality of concatemer extension products are immobilized to said surface through duplexes formed between said concatemer extension products and said capture probes.

6. The random array of claim 4, wherein said capture probes are distributed in discrete regions on said surface, and wherein areas surrounding said discrete regions do not bind said concatemers or said concatemer extension products.

7. The random array of claim 4, wherein at least a portion of said first or second target sequences have been identified in a sequencing reaction.

8. The random array of claim 1 or 4, wherein for a number of said immobilized concatemers, different concatemers comprise first and second target sequences from different target polynucleotides.

* * * * *

SEQUENCE LISTING

```
<160> NUMBER OF SEQ ID NOS: 11

<210> SEQ ID NO 1
<211> LENGTH: 80
<212> TYPE: DNA
<213> ORGANISM: Artificial Sequence
<220> FEATURE:
<223> OTHER INFORMATION: Synthetic oligo T1N
<220> FEATURE:
<221> NAME/KEY: misc_feature
<222> LOCATION: (1)...(8)
<223> OTHER INFORMATION: n may be any one of four possible bases A,
      C, T or G
<220> FEATURE:
<221> NAME/KEY: misc_feature
<222> LOCATION: 14, 20, 26, 32, 47, 53, 67, 70
<223> OTHER INFORMATION: n may be any one of four possible bases A,
      C, T or G
<220> FEATURE:
<221> NAME/KEY: misc_feature
<222> LOCATION: (73)...(80)
<223> OTHER INFORMATION: n may be any one of four possible bases A,
      C, T or G

<400> SEQUENCE: 1
nnnnnnnngc atancacgan gtcatnatcg tncaaacgtc agtccangaa tcnagatcca      60
cttagantgn cgnnnnnnnn                                                  80

<210> SEQ ID NO 2
<211> LENGTH: 50
<212> TYPE: DNA
<213> ORGANISM: Artificial Sequence
<220> FEATURE:
<223> OTHER INFORMATION: BR2-ad

<400> SEQUENCE: 2
tatcatctgg atgttaggaa gacaaaagga agctgaggac attaacggac                 50

<210> SEQ ID NO 3
<211> LENGTH: 15
<212> TYPE: DNA
<213> ORGANISM: Artificial Sequence
<220> FEATURE:
<223> OTHER INFORMATION: UR3-ext
```

-continued

```
<400> SEQUENCE: 3
accttcagac cagat                                                          15

<210> SEQ ID NO 4
<211> LENGTH: 25
<212> TYPE: DNA
<213> ORGANISM: Artificial Sequence
<220> FEATURE:
<223> OTHER INFORMATION: BR2-temp
<220> FEATURE:
<221> NAME/KEY: misc_feature
<222> LOCATION: (1)...(7)
<223> OTHER INFORMATION: n may be any one of four possible bases A,
      C, T or G

<400> SEQUENCE: 4
nnnnnnngtc cgttaatgtc ctcag                                               25

<210> SEQ ID NO 5
<211> LENGTH: 22
<212> TYPE: DNA
<213> ORGANISM: Artificial Sequence
<220> FEATURE:
<223> OTHER INFORMATION: UR3-temp
<220> FEATURE:
<221> NAME/KEY: misc_feature
<222> LOCATION: (16)...(22)
<223> OTHER INFORMATION: n may be any one of four possible bases A,
      C, T or G

<400> SEQUENCE: 5
atctggtctg aaggtnnnnn nn                                                  22

<210> SEQ ID NO 6
<211> LENGTH: 20
<212> TYPE: DNA
<213> ORGANISM: Artificial Sequence
<220> FEATURE:
<223> OTHER INFORMATION: Biotin labeled probe BR-rc-bio

<400> SEQUENCE: 6
cttttgtctt cctaacatcc                                                     20

<210> SEQ ID NO 7
<211> LENGTH: 16
<212> TYPE: DNA
<213> ORGANISM: Artificial Sequence
<220> FEATURE:
<223> OTHER INFORMATION: Aplint oligo UR3-closing-88

<400> SEQUENCE: 7
agatgataat ctggtc                                                         16

<210> SEQ ID NO 8
<211> LENGTH: 14
<212> TYPE: DNA
<213> ORGANISM: Artificial Sequence
<220> FEATURE:
<223> OTHER INFORMATION: Palindrome example

<400> SEQUENCE: 8
aaaaaaattt tttt                                                           14

<210> SEQ ID NO 9
<211> LENGTH: 14
<212> TYPE: DNA
<213> ORGANISM: Artificial Sequence
```

-continued

```
<220> FEATURE:
<223> OTHER INFORMATION: Palindrome example

<400> SEQUENCE: 9
tttttttaaa aaaa                                                     14

<210> SEQ ID NO 10
<211> LENGTH: 16
<212> TYPE: DNA
<213> ORGANISM: Artificial Sequence
<220> FEATURE:
<223> OTHER INFORMATION: Exemplary tail sequence for label probes

<400> SEQUENCE: 10
cgcgatatcg cgatat                                                   16

<210> SEQ ID NO 11
<211> LENGTH: 12
<212> TYPE: DNA
<213> ORGANISM: Artificial Sequence
<220> FEATURE:
<223> OTHER INFORMATION: Exemplary tail sequence for label probes

<400> SEQUENCE: 11
cgatcgatcg at                                                       12
```